US007488753B2

(12) United States Patent
Chan et al.

(10) Patent No.: US 7,488,753 B2
(45) Date of Patent: Feb. 10, 2009

(54) COMPOSITION COMPRISING TRITERPENE SAPONINS AND COMPOUNDS WITH ANGELOYL FUNCTIONAL GROUP, METHODS FOR PREPARING SAME AND USES THEREOF

(75) Inventors: Pui-Kwong Chan, Sugarland, TX (US); May Sung Mak, Kowloon (HK); Yun Wang, Dunedin (NZ)

(73) Assignee: Pacific Arrow Limited, North Point, Hong Kong (CN)

( * ) Notice: Subject to any disclaimer, the term of this patent is extended or adjusted under 35 U.S.C. 154(b) by 86 days.

(21) Appl. No.: 11/289,142

(22) Filed: Nov. 28, 2005

(65) Prior Publication Data

US 2006/0122129 A1 Jun. 8, 2006

Related U.S. Application Data

(63) Continuation-in-part of application No. 11/267,523, filed on Nov. 4, 2005, now abandoned, and a continuation-in-part of application No. PCT/US2005/031900, filed on Sep. 7, 2005, and a continuation-in-part of application No. 11/131,551, filed on May 17, 2005, now Pat. No. 7,262,285, and a continuation-in-part of application No. 11/117,760, filed on Apr. 27, 2005, and a continuation-in-part of application No. 10/906,303, filed on Feb. 14, 2005, and a continuation-in-part of application No. PCT/US2004/043465, filed on Dec. 23, 2004, which is a continuation-in-part of application No. PCT/US2004/033359, filed on Oct. 8, 2004, said application No. PCT/US2005/031900.

(60) Provisional application No. 60/675,284, filed on Apr. 27, 2005, provisional application No. 60/675,282, filed on Apr. 27, 2005, provisional application No. 60/617,379, filed on Oct. 8, 2004, provisional application No. 60/613,811, filed on Sep. 27, 2004, provisional application No. 60/607,858, filed on Sep. 7, 2004, provisional application No. 60/532,101, filed on Dec. 23, 2003, provisional application No. 60/509,851, filed on Oct. 9, 2003.

(51) Int. Cl.
*A61K 31/22* (2006.01)
*C07C 69/533* (2006.01)
(52) U.S. Cl. ........................ 514/510; 514/529; 560/116
(58) Field of Classification Search ........................ None
See application file for complete search history.

(56) References Cited

U.S. PATENT DOCUMENTS

| 6,616,943 | B2 | 9/2003 | Wang et al. | |
|---|---|---|---|---|
| 7,189,420 | B2 | 3/2007 | Wang | |
| 7,262,285 | B2 * | 8/2007 | Chan et al. | 536/18.1 |
| 2003/0082293 | A | 5/1993 | Wang et al. | |
| 2003/0096030 | A1 | 5/2003 | Wang et al. | |
| 2005/0220910 | A1 * | 10/2005 | Chan et al. | 424/769 |
| 2005/0245470 | A1 * | 11/2005 | Chan et al. | 514/33 |
| 2005/0276872 | A1 | 12/2005 | Chan et al. | |
| 2006/0111310 | A1 | 5/2006 | Chan et al. | |
| 2006/0122129 | A1 * | 6/2006 | Chan et al. | 514/33 |
| 2006/0263458 | A1 | 11/2006 | Chan et al. | |
| 2007/0161580 | A1 * | 7/2007 | Chan et al. | 514/33 |

FOREIGN PATENT DOCUMENTS

| AU | 2002348988 | 1/2004 |
|---|---|---|
| AU | 2002348988 | 11/2007 |
| CA | 2451740 | 12/2003 |
| CN | 93111010.6 | 5/1994 |
| CN | 1092992 A | 10/1994 |
| CN | 1236792 C | 1/2006 |
| EP | 02781502.6 | 2/2004 |
| HK | 05102536.2 | 3/2005 |
| JP | 2003-522442 | 2/2004 |
| KR | 10-2004-7002889 | 2/2004 |
| NZ | 530449 | 1/2004 |
| NZ | 530449 | 10/2007 |
| SG | 200400403-2 | 3/2006 |
| TW | 93140030 | 12/2004 |
| TW | 94130519 | 9/2005 |
| WO | WO 03/017919 | 3/2003 |
| WO | WO/2003/017919 | 3/2003 |
| WO | WO/2005/037200 | 4/2005 |
| WO | WO/2005/063273 | 7/2005 |
| WO | WO/2006/029221 | 3/2006 |
| WO | WO/2006/116656 | 11/2006 |
| WO | PCT/US2007/077273 | 8/2007 |

OTHER PUBLICATIONS

The Merck Manual of Diagnosis and Therapy, seventeenth edition, 1999, Published by Merck Research Laboratories, pp. 397-398, 948-949, 1916, and 1979-1981.*
The Oxford Textbook of Oncology, 1995, published by Oxford University Press, pp. 447-453.*
Konoshima et al., "Antitumor Agents, 82. Cytotoxic sapogenols from aesculus hippocastanum" Journal of Natural Products (1986) vol. 49 No. 4, pp. 650-656.*
U.S. Appl. No. 60/617,379, filed Oct. 8, 2004, Mak, May Sung.
U.S. Appl. No. 60/613,811, filed Sep. 27, 2004, Mak et al.
U.S. Appl. No. 60/607,858, filed Sep. 7, 2004, Mak et al.
U.S. Appl. No. 60/532,101, filed Dec. 23, 2003, Wang et al.
U.S. Appl. No. 60/509,851, filed Oct. 9, 2003, Wang et al.

(Continued)

*Primary Examiner*—Shaojia Anna Jiang
*Assistant Examiner*—Eric S Olson
(74) *Attorney, Agent, or Firm*—Law Offices of Albert Wai-Kit Chan, PLLC

(57) ABSTRACT

This invention provides composition comprising a triterpenoidal saponin, comprising two side groups attached to carbon 21, and 22 of triterpenoidal saponin backbone. This invention provides a composition for inhibiting skin or ovarian tumor cell growth, comprising an appropriate amount of said compound.

1 Claim, 34 Drawing Sheets

OTHER PUBLICATIONS

U.S. Appl. No. 60/675,807, filed Apr. 27, 2005, Chan et al.
U.S. Appl. No. 60/841,727, filed Sep. 1, 2006, Mak, May Sung.
U.S. Appl. No. 60/675,282, filed Apr. 27, 2005, Chan et al.
U.S. Appl. No. 11/683,198, filed Mar. 7, 2007, Chan et al.
PCT International Search Report for Pacific Arrow Limited, International App'l No. PCT/US2005/031900, filed Sep. 7, 2005, Dated Feb. 6, 2007.
PCT Written Opinion of the International Searching Authority for Pacific Arrow Limited, International App'l No. PCT/US2005/031900, filed Sep. 7, 2005, Dated Feb. 6, 2007.
PCT International Preliminary Report on Patentability for Pacific Arrow Limited, International App'l No. PCT/US2005/031900, filed Sep. 7, 2005, Dated Mar. 22, 2007.
PCT International Preliminary Report on Patentability, for Pacific Arrow Limited, International App'l No. PCT/US2004/043465, filed Dec. 23, 2004.
PCT International Search Report for Pacific Arrow Limited, International App'l No. PCT/US2006/016158, filed Apr. 27, 2006, Dated Nov. 13, 2006.
PCT Written Opinion of the International Searching Authority for Pacific Arrow Limited, International App'l No. PCT/US2006/016158, filed Apr. 27, 2006, Dated Nov. 13, 2006.
PCT International Preliminary Report on Patentability for Pacific Arrow Limited, International App'l No. PCT/US2006/016158, filed Apr. 27, 2006, Dated Oct. 30, 2007.
Notice of Acceptance for Wang, Yun, Australia Patent App'l No. 2002348988, filed Jan. 21, 2004, Dated Jul. 13, 2007.
Notice of Acceptance for Wang, Yun, New Zealand Patent No. App'l No. 530449, filed Jan. 6, 2004, Dated Jun. 12, 2007.
Supplemental European Search Report for Fountain Silver Limited, European Application No. 02781502.6, filed Feb. 25, 2004, Dated Jul. 6, 2005.
European Office Communication for Wang, Yun, European Application No. EP 02781502.6, filed Feb. 25, 2004, Dated Jul. 20, 2007.
European Office Communication for Wang, Yun, European Application No. EP 02781502.6, filed Feb. 25, 2004, Dated Oct. 12, 2005.
New Zealand Examination Report for Wang, Yun, New Zealand Patent No. App'l No. 530449, filed Jan. 6, 2004, Dated Feb. 15, 2006.
New Zealand Examination Report for Wang, Yun, New Zealand Patent No. App'l No. 530449, filed Jan. 6, 2004, Dated Apr. 10, 2007.
U.S. Office Action for Chan, et al., U.S. Appl. No. 11/117,745, filed Apr. 27, 2005, Dated Mar. 12, 2007.
U.S. Office Action for Chan, et al., U.S. Appl. No. 11/117,745, filed Apr. 27, 2005, Dated Aug. 22, 2007.
U.S. Office Action for Chan, et al., U.S. Appl. No. 11/117,760, filed Apr. 27, 2005, Dated Jun. 29, 2007.
U.S. Office Action for Chan, et al., U.S. Appl. No. 11/117,760, filed Apr. 27, 2005, Dated Aug. 20, 2007.
U.S. Final Office Action for Mak, et al., U.S. Appl. No. 11/412,659, filed Apr. 27, 2006, Dated Sep. 5, 2007.
U.S. Office Action for Chan, et al., U.S. Appl. No. 11/131,551, filed May 17, 2005, Dated Jan. 22, 2007.
U.S. Notice of Allowability for Chan, et al., U.S. Appl. No. 11/131,551, filed May 17, 2005, Dated May 11, 2007.
U.S. Office Action for Chan, et al., U.S. Appl. No. 11/289,142, filed Nov. 28, 2005, Dated Sep. 27, 2007.
U.S. Office Action for Chan, et al., U.S. Appl. No. 11/267,523, filed Nov. 4, 2005, Dated Sep. 27, 2007.
U.S. Office Action for Chan, et al., U.S. Appl. No. 10/906,303, filed Feb. 14, 2005, Dated Jan. 4, 2008.
U.S. Office Action for Chan, et al., U.S. Appl. No. 11/117,745, filed Apr. 27, 2005, Dated Jan. 25, 2008.
Chan, Pui-Kwong, 2007, "Acylation with diangeloyl groups at C21-22 positions in triterpenoid saponins is essential for cytotoxcity towards tumor cells", Biochemical Pharmacology 73(2007): 341-350.
D'Acquarica, I., 2002, "Isolation and structure elucidation of four new triterpenoid estersaponins from fruits of *Pittosporum tobira* AIT." Tetrahedron, vol. 58: 10127-10136.
Lavaud, et al., 1992, "Saponins from *Steganotaenia araliacea*", Phycochemistry, vol. 31(9):3177-3181.

Li, et al., 2005, "Two New Triterpenes from the Husks of *Xanthoceras sorbifolia*", Planta Medica, vol. 71:1068-1070.
Ma, et al, 2000, Inhibitory Effects on HIV-1 Protease of Constituents from the Wood of *Xanthoceras sorbifolia*, Journal Natural Products, vol. 63:238-242.
The Merck Manual of Diagnosis and Therapy, 17th Edition, 1999, Published by Merck Research Lanoratories, pp. 397-398, 948-949, 1916, and 1979-1981.
Nethaji, et al., 1993, "Molecular Structure of lantadene-B&C, Triterpenoids of Lantana Camara, Red Variety; lantadene-B, 22β-angeloyloxy-3-oxoolean-12-en-28-oic acid; Lantadene-C, 22 β-(S)-2'-methyl butanoyloxy-3-oxoolean-12-en-28-oic acid." Journal of Crystallographic and Spectroscopic Research. vol. 23(6):469-472.
The Oxford Textbook of Oncology, 1995, published by Oxford University Press, pp. 447-453.
Voutquenne, et al., 2005, "Haemolytic Acylated Triterpenoid saponins from *Harpullia austro-caledonica*". Phytochemistry, vol. 66: 825-826.
Zhang, et al., 2007, "Cytotoxic triterpenoid saponins from the fruits of *Aesculus pavia* L", Phytochemistry 68: 2075-2086.
Arda, et al. "Saniculoside N from *Sanicula europaea* L." Journal of Natural Products (1997), 60(11), 1170-1173.
Azam, et al. "A triterpenoldal sapogenin from the seeds of *Dodonaea viscosa* Linn." Indian Journal of Chemistry, Section B: Organic Chemistry Including Medicinal Chemistry (1993). 32B(4), 513-14.
Barre, et al. "A bioactive triterpene from Lantana camara." Phytochemistry (1997), 45(2), 321-324.
Barua, et al. "Triterpenoids. XXIX. Structure of barringtogenol B-a new triterpenoid sapogenin from *Barringtonia acutangula*." Tetrahedron (1968), 24(3), 1113-17.
Beeby, et al. "Angeloyl chloride: synthesis and utilization in the partial synthesis of lantadene A (rehmannic acid)." Tetrahedron Letters (1977), (38), 3379-82.
Brown, et al. "The relation of chemical structure to the Icterogenic and photosensitizing action of some naturally occuring and synthetic triterpene acids," South African Journal of Laboratory and Clinical Medicine (1963), 9 262-72.
Brown, et al. "Biliary excretion In the rabbit. II. The relation between the chemical structure of certain natural or synthetic pentacyclic triterpenes and their Icterogenic activity. 2. The substituents on carbon atoms 17, 29, 20, and 22." Proc. Roy. Soc. (London) Ser. B (1964), 160(979), 246-57.
Chen, et al. "Studies on the constituents of *Xanthoceras sorbifolia* Bunge. (I)." Shoyakugaku Zasshi (1984), 38(2), 203-6.
Chen, et al. "Studies on the constituents of *Xanthoceras sorbifolia* Bunge. II." Chemical & pharmaceutical bulletin (Sep. 1984), 32(9), 3378-83.
Chen, et al. "Studies on the constituents of *Xanthoceras sorbifolia* Bunge. III." Chemical & Pharmaceutical Bulletin (1985), 33(1), 127-34.
Chen, et al. "Studies on the constituents of *Xanthoceras sorbifolia* Bunge. IV. Structures of the minor prosapogenins." Chemical & Pharmaceutical Bulletin (1985), 33(3), 1043-8.
Chen, et al. "Studies on the constituents of *Xanthoceras sorbifolia* Bunge. V. Major saponins from the fruits of *Xanthoceras sorbifolia* Bunge." Chemical & Pharmaceutical Bulletin (1985), 33(4), 1387-94.
Cheng, et al. "Two new sterols in husk of *Xanthoceras sorbifolia*." Zhongcaoyao (2001), 32(3), 199-201.
Chakravarty, et al. "Triterpenoid prosaponins from leaves of *Maesa chisia var. angustifolia*." Phytochemistry (1987), 26(8), 2345-9.
Cui, et al. "2D NMR structure determination of five flavonoids from the wood of *Xanthoceras sorbifolia* Bunge." Shenyang Yaoxueyuan Xuebao (1991), 8(1), 36-8, 57.
Cui, et al. "Blood-activating constituents of Wenguanmu (*Xanthoceras sorbifolia*)," Zhongcaoyao (1987), 18(7), 297-8, 296.
Cui, et al. "The application of the microcomputer in the study of Chinese herb and natural drugs. 1. The Basic program used for the design of liquid-liquid extraction and forecasting the results of extraction and separation." Shenyang Yeoxueyuan Xuebao (1986), 3(2), 79-84.

Eakins, et al. "The effect of three triterpene acids and sporidesmin on the enzyme activities of rat liver plasma membranes." Chemico-Biological Interactions (1978), 21(1), 117-24.

Eakins, et al. "Studies on blle secretion with the aid of the Isolated perfused rat liver. II, The effect of two further pentacyclic triterpenes, asiatic acid and 22-engeloyloxyolaanolicacid," Chemico-Biological Interactions (1978), 21(1), 79-87.

Hart, et al. "New triterpenes of Lantana camara. A comparative study of the constituents of several taxa." Australian Journal of Chemistry (1976), 29(3), 655-71.

Hopkins, et al. "Eicosenoic acid and other fatty acids of Sapindaceae seed oils," Lipids (1967), 2(3), 258-60.

Hu, et al. "Preparation of high-heating value synthetic liquid fuels." Faming Zhuanli Shenqing Gongkai Shuomingshu (1999), 4 pp.

Hu, et al. "Preparation of liquid fuels having high caloric value." Faming Zhuanli Shenqing Gongkai Shuominghsu (1994), 5 pp.

Huang, et al. "Chemical constitutents of Wenguanmu (*Xanthoceras sorbifolia*) (I)." Zhongcaoyao (1987), 18(5), 199-202.

Huang, et al. "Preliminary studies on absorption and accumulation of atmospheric lead and cadmium by woody plants." Linye Kexue (1982), 18(1), 93-7.

Kim, et al. "Fatty-acid composition of vegetable oils." Choson Minjujuui Inmin Konghwaguk Kwahagwon Tongbo (1985), (3), 43-6.

Koike, et al. "New triterpenoid saponins from *Maesa japonica*." Journal of Natural Products (1999), 62(2), 228-232.

Kuang, et al. "Anti-inflammatory effects of n-butanol extract of *Xanthoceras sorbifolia* Bunge." Shenyang Yaoke Daxue Xuebao (2001), 18(1), 53-56.

Li, et al. "Medicine for enhancing mental activity." Faming Zhuanli Shenqing Gongkai Shuomingshu (1994), 7 pp.

Li, et al. "*Xanthoceras sorbiofolia* fruit extracts for enhancing mental activity," Faming Zhuanli Shenqing Gongkai Shuomingshu (1994), 6 pp.

Li, et al. "Identification of fatty acids in the kernel oil of *Xanthoceras sorbifolla* Bge. with GC-MS." Zhiwu Ziyuan Yu Huanjing (1993), 2(2), 28-32.

Li, et al. "Isolation and structural determination of triterpene alcohols and 4-methylsterols in unsaponifiable fraction of the oil from *Xanthoceras sorbifolia* Bge," Linye Kexue (1984), 20(4), 397-402.

Li, et al. "Eremophilenolides and other constituents from the roots of *Ligularia sagitta*." Planta Medica (2003), 69(4), 356-360.

Li, et al. "New gualanolides and xanthine oxidase inhibitory flavonols from *Ajania fruticulosa*." Journal of Natural Products (1999), 62(7), 1053-1055.

Liu, et al. "The components of *Cacalia tangutica*." Bulletin of the Korean Chemical Society (2004), 25(7), 1078-1080.

Ma, et al. "A novel protoilludane sesquiterpene from the wood of *Xanthoceras sorbifolia*." Chinese Chemical Letters (2004), 15(1), 65-67.

Ma, et al. "Screening of Chinese and Mongolian herbal drugs for anti-human immunodeficiency virus type 1 (HIV-1) activity." Phytotherapy Research (2002), 16(S1), 186-189.

Ma, et al. "Inhibitory effects on HIV-1 protease of constituents from the wood of *Xanthoceras sorbifolia*." Journal of natural products (Feb. 2000), 63(2), 238-42.

Mahato, et al. "New triterpenoids from *Lantana camara*: Isomerisation of the angeloyl moiety of lantedene a during catalytic hydrogenation." Journal of the Indian Chemical Society (1999), 76(11-12), 723-726.

Meng, et al. "Antifungal highly oxygenated guaianolides and other constituents from *Ajania fruticulosa*." Phytochemistry (2001), 58(7), 1141-1145.

Nakamura, et al. "Inhibitory effects of some traditional medicines on proliferation of HIV-1 and its protease." Yakugaku Zasshi (2004), 124(8), 519-529.

42. Nothaji, et al. "Molecular structure of lantadene-B&C, triterpenoids of *Lantana camara*, red variety: lantadene-B, 22β-angeloyloxy-3-oxoolean-12-en-28-oic acid; lantadene-C, 22 β-(S)-2'-methyl butanoyloxy-3-oxoolean-12-en-2B-oic acid." Journal of Crystallographic and Spectroscopic Research (1993), 23(6), 469-72.

Plouvier, et al. "Fraxoside and coumarin heterosides occurring in various botanical groups." Comptes Rendus des Seances de l'Academie des Sciences, Serie D: Sciences Naturelles (1968), 267 (22), 1883-5.

Plouvier, et al. "Flavone heterosides: kaempferol 3-rhamnoglucoside, myricitrin, llnarin, and saponarin." Comptes Rendue des Seences de l'Academie des Sciences, Serie D: Sciences Naturelles (1966), 262(12), 1368-71.

Plouvier, et al."Oil of the seeds of *Xanthoceras sorbifolia* Bunge and of *Koelreuteria paniculata* Laxm." Compt. rend. (1946), 222 916-17.

Sakurai, et al. "Assamicin I and II, novel triterpenoid saponins with insulin-like activity from *Aesculus assamica* Griff." Bioorganic & Medicinal Chemistry Letters (2002), 12(5), 807-810.

Semikhov, et al. "Comparative study of the amino acid composition of the embryo in grasses (Poaceae) and other flowering plants," Botanicheskii Zhurnal (Sankt-Peterburg. Russian Federation) (1994), 79(3). 83-92.

Sharma, et al. "Molecular structure, polymorphism, and toxicity of lantadene A, the pentacyclic triterpenoid from the hepatotoxic plant *Lantana camar*." Journal of biochemical toxicology (1991 Spring), 6(1), 57-63.

Shang-Jiang, et al. "Constituents of Shashen (*Adenophora axillifiora*)." Planta Medica (1986), (4), 317-20.

Sindambiwe, et al. "Triterpenoid saponins from *Maesa lanceolata*." Phytochemistry (1996), 41(1), 269-77.

Singh, et al. "Biotransformation of lantadene A (22β-angeloyloxy-3-oxooclean-12-an-28-oic acid), the pentacyclic triterpenoid, by *Alcaligenes faecalis*." Biodegradation (1999), 10(5), 373-381.

Tian, et al. "Study on the vegetative storage proteins in temperate hardwoods of fifteen familes." Xibei Zhiwu Xuebao (2000), 20(5), 835-841.

"Triterpenoids. XVI. The constitution of rehmannic acid." Journal of the Chemical Society, Abstracts (1954), 900-3.

Tuntiwachwuttikul, et al. "A triterpenoid saponin from *Maesa ramentacea*." Phytochemistry (1997), 44(3), 491-495.

Voutquenne, et al. "Triterpenoid saponins and acylated prosapogenins from *Harpullia austro*-caledonica." Phytochemistry (2002), 59(8), 825-832.

Wang, et al. "Chemical constituents of the oil and kernels of *Xanthoceras sorbifolia* Bunge." Zhiwu Xuebao (1981), 23(4), 331-3.

Waechter, et al. "Antitubercular Activity of Triterpenoids from *Lippia turbinata*." Journal of Natural Products (2001), 64(1), 37-41.

Yan, et al. "Separation, identification and determination of the unsaponifiable matters in vegetable oils." Beijing Shifan Daxue Xuebao, Ziran Kexueban (1985), (1), 53-8.

Yan, et al. "Isolation, content analysis and structural determination of sterols in unsaponifiable fraction of the oil from *Xanthoceras sorbifolia* Bge." Linye Kexue (1984), 20(4), 389-96.

Yang, et al. "Extraction of total saponin, fat, protein, and saccharide from *Xanthoceras sorbifolia*." Faming Zhuanli Shenqing Gongkai Shuomingshu (2002), 4 pp.

Yang, et al. "Application of the extract of *Xanthoceras sorbifolia* shell in preparing the food and medicine for improving brain functions." Faming Zhuanli Shenqing Gongkai Shuomingshu (2002), 6 pp.

Yang, et al. "Two new triterpenoid saponins from the seeds of *Aesculus chinensis*." Chinese Chemical Letters (2000), 11(2), 139-142.

Zhang, et al. "Quantitative determination of myricetin and quercetin in *Xanthoceras sorbifolia* Bunge by HPLC." Shenyang Yaoke Daxue Xuebao (2000), 17(3), 194-196.

Zhang, et al. "Studies on chemical constituents of *Xanthoceras sorbifolia* Bunge." Yaoxue Xuebao (2000), 35(2), 124-127.

Zhao, et al. "Four new triterpene saponins from the seeds of *Aesculus chinensis*." Journal of Asian Natural Products Research (2003), 5(3), 197-203.

Zhao, et al. "Three new triterpene saponins from the seeds of *Aesculus chinensis*." Chemical & Pharmaceutical Bulletin (2001), 49(5), 626-628.

Zheng, et al. "Triterpenoids from *Mosla chinensis*." Indian Journal of Chemistry, Section B: Organic Chemistry Including Medicinal Chemistry (2000), 39B(11), 875-878.

Apers, et al. "New acylated triterpenoid saponins from *Maesa lanceolata*." Phytochemistry 52 (1999) 1121-1131.

D'Acquarica, et al. "Isolation and structure elucidation of four new triterpenoid estersaponins from fruits of Pittosporum tobira AIT." Tetrahedron 58 (2002) 10127-10136.

Jiang, et al. "Six Triterpenoid Saponins from *Maesa laxiflora*." J. Nat. Prod. 1999, 62, 873-876.

Lu, et al. "Triterpenoid saponins from the roots of tea plants (*Camellia sinensis* var. *assamica*)." Phytochemistry 53 (2000) 941-946.

Seo, et al. "A New Triterpene Saponin from Pittosporum viridiflorum from the Madagascar Rainforest." J. Nat. Prod. 2002, 65, 65-68.

Yang, et al. "Anti-HIV-1 Protease Triterpenoid Saponins from the Seeds of *Aesculus chinensis*." J. Nat. Prod. 1999, 62, 1510-1513.

Written Opinion of the International Searching Authority for PCT/US04/33359, filed Oct. 8, 2004 for Pacific Arrow Limited et al., dated Apr. 12, 2005.

International Search Report for PCT/US04/33359, filed Oct. 8, 2004 for Pacific Arrow Limited et al., dated Apr. 12, 2005.

Written Opinion of the International Searching Authority for PCT/US04/43465, filed Dec. 23, 2004 for Pacific Arrow Limited et al., dated May 17, 2005.

International Search Report for PCT/US04/43465, filed Dec. 23, 2004 for Pacific Arrow Limited et al., dated May 17, 2005.

Supplementary European Search Report issued on Jul. 6, 2005 for Fountain Silver Limited et al., European Patent Application No. 02781502.6.

* cited by examiner

Structure of saponin

Figure 2
Structure of saponin
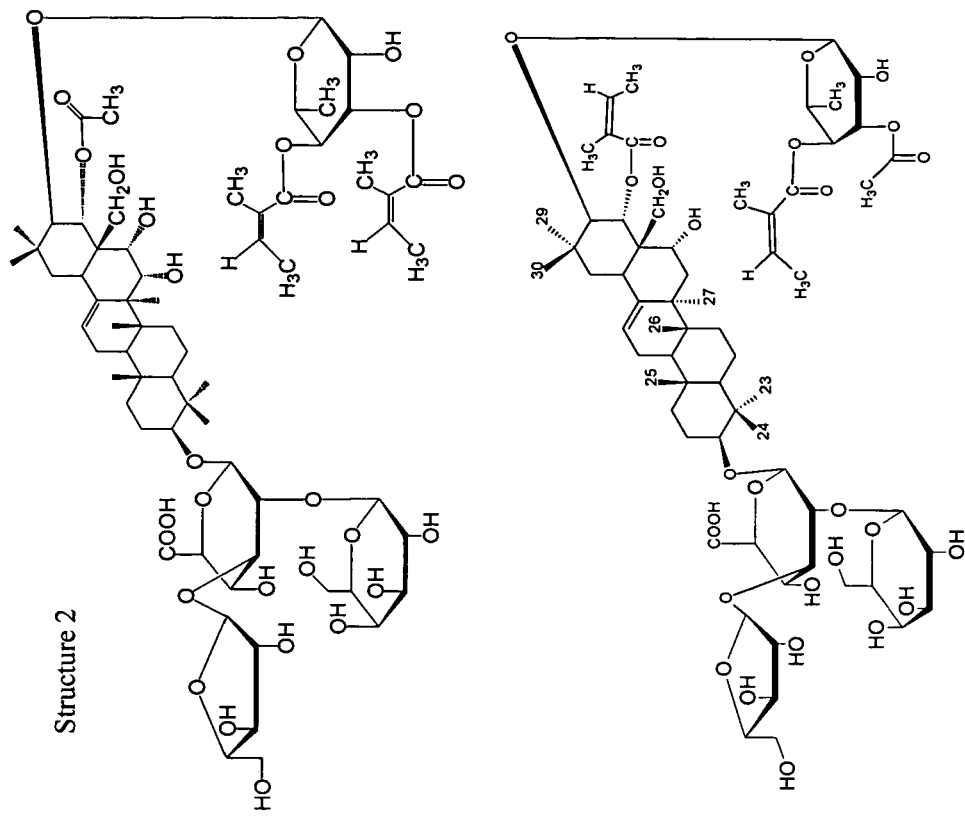
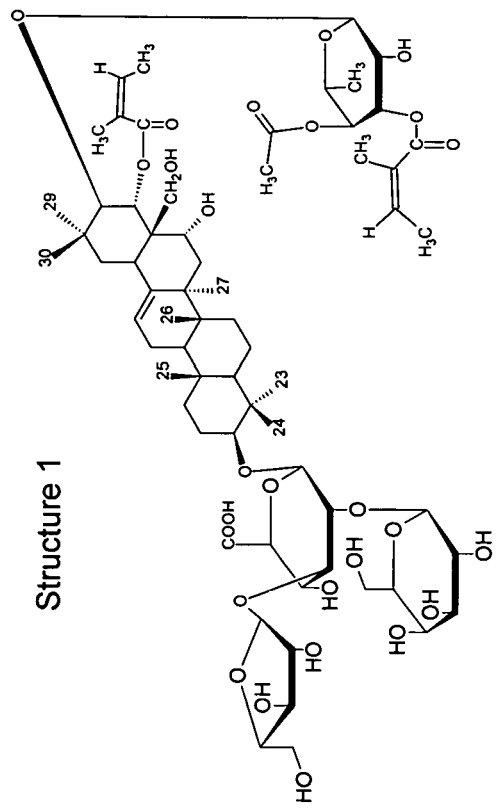

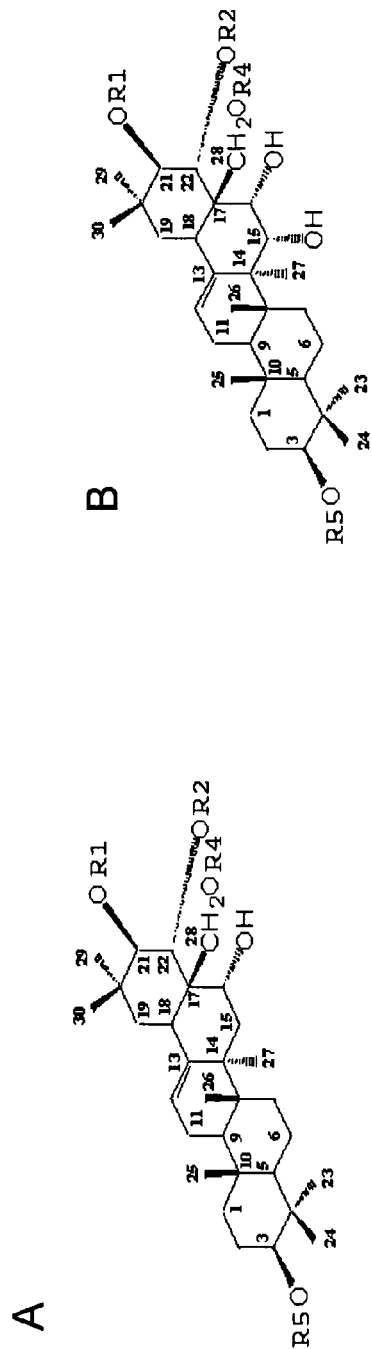

Figure 3
Structure of saponin

R5 = B or C or S1 (see note 1)
R1 = A or B or C
R2 = A or B or C
R4 = A or B or C Note 1:
A = angeloyl or Tigloyl or Senecioyl
B = acetyl
C = H
S1 = sugar moiety comprising one or more sugar, D- glucose, D- galactose, L-rhamnose, L-arabinose, D-xylose, alduronic acid, D-glucuronic acid, D-galacturonic acid, or their derivatives.
Positions 23-27, 29-30 are attached with $CH_3$ or $CH_2OH$ or $COOH$ or acetyl group Structure of saponin

Figure 5
Structure of saponin

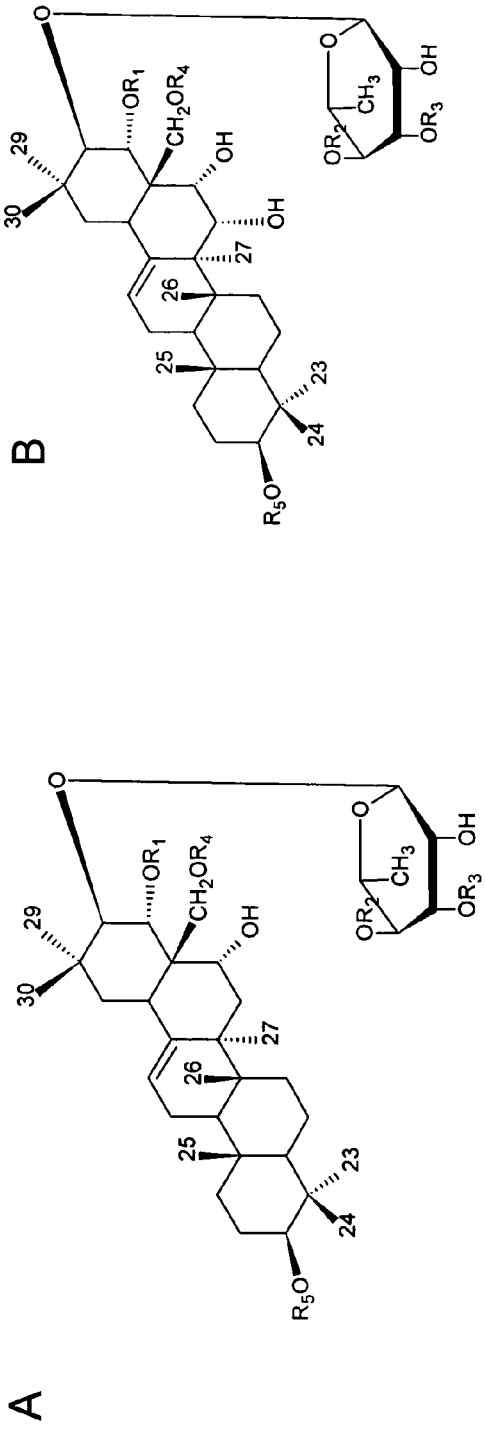

R5 = B or C or S1 (see note 1)
R1 = A or B or C
R2 = A or B or C
R3 = A or B or C
R4 = A or B or C Note 1:
A = angeloyl or Tigloyl or Senecioyl
B = acetyl
C = H
S1= sugar moiety comprising one or more sugar, D- glucose, D- galactose, L-rhamnose, L-arabinose, D-xylose, alduronic acid , D-glucuronic acid, D-galacturonic acid, or their derivatives. positions 23-27, 29-30 are attached with CH3 or CH2OH or COOH or acetyl group

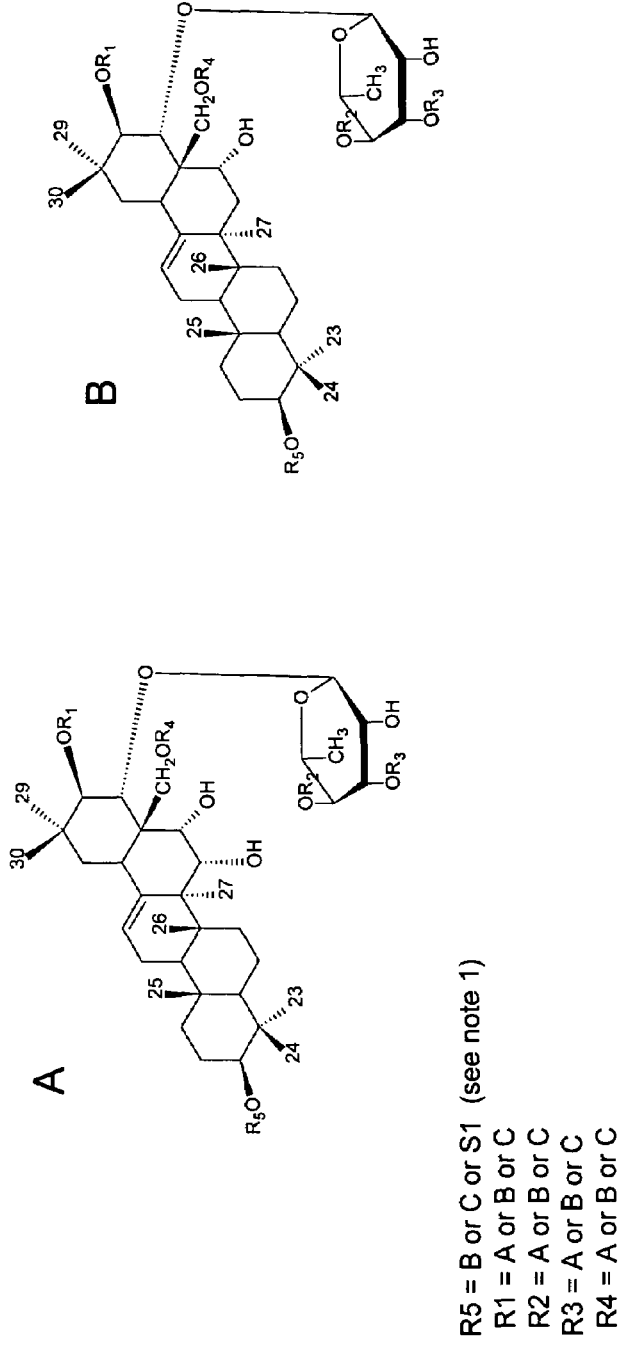

Figure 6
Structure of saponin

R5 = B or C or S1 (see note 1)
R1 = A or B or C
R2 = A or B or C
R3 = A or B or C
R4 = A or B or C Note 1:
A = angeloyl or Tigloyl or Senecioyl
B = acetyl
C = H
S1= sugar moiety comprising one or more sugar, D- glucose, D-galactose, L-rhamnose, L-arabinose, D-xylose, alduronic acid , D- glucuronic acid, D-galacturonic acid, or their derivatives.
positions 23-27, 28-30 are attached with CH3 or CH2OH or COOH or acetyl group Figure 12
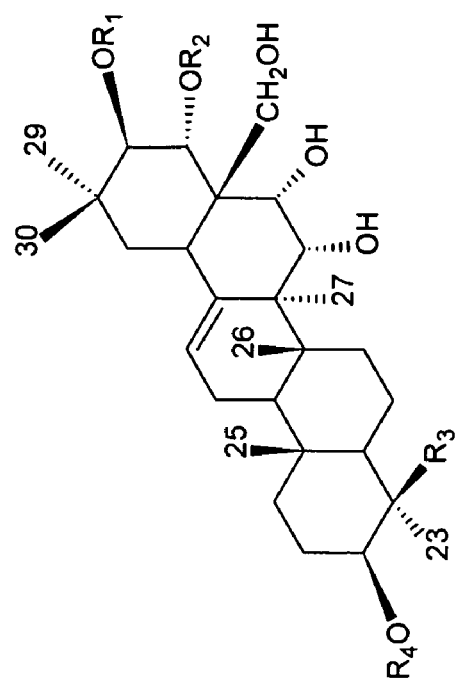
B
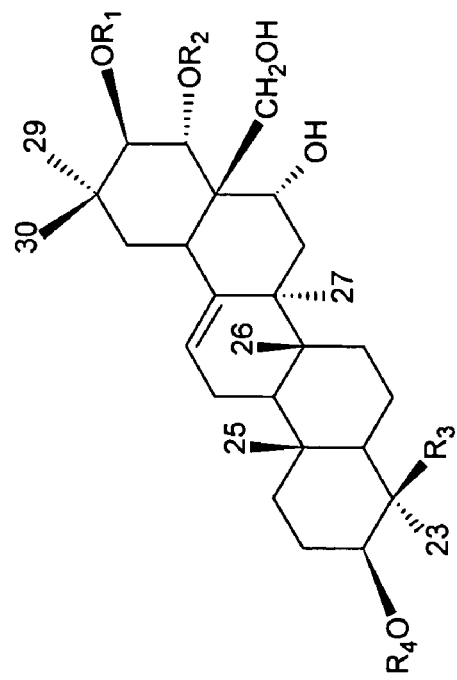
A

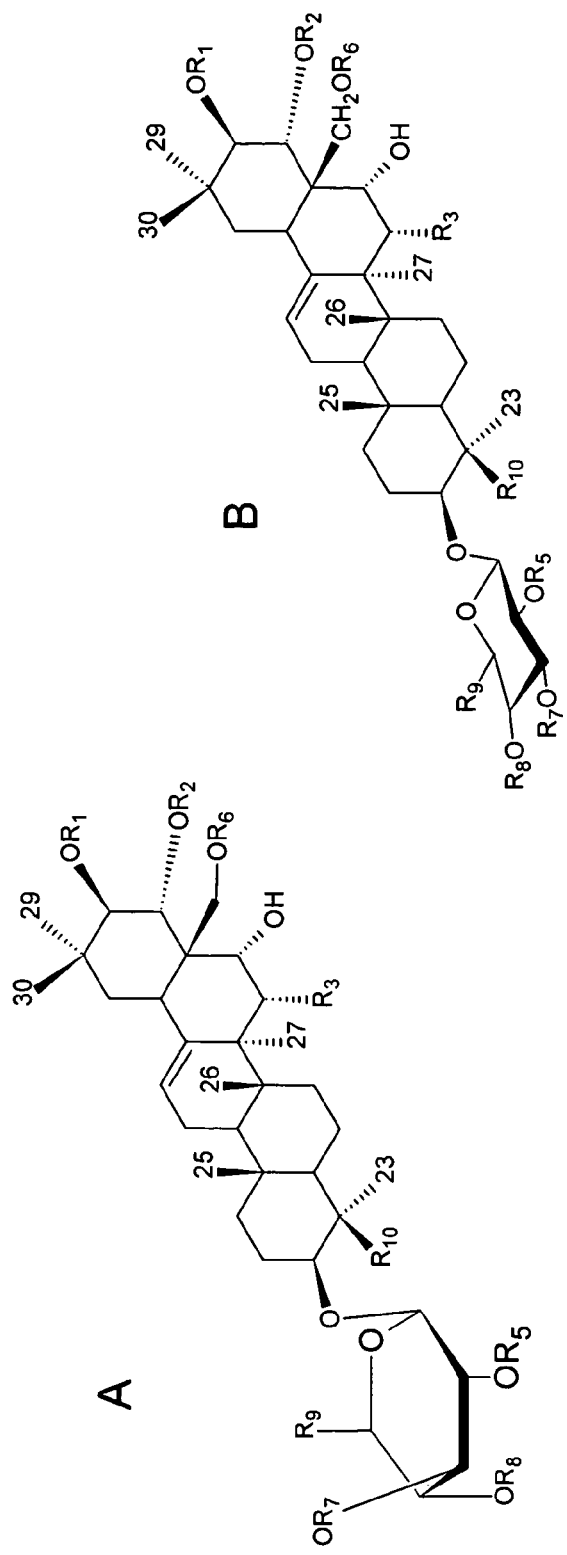

Figure 16

R1= angeloyl or Tigloyl or Senecioyl or acetyl or H
R2= angeloyl or Tigloyl or Senecioyl or acetyl or H
R6= angeloyl or Tigloyl or Senecioyl or acetyl or H
R3=H or OH
R10=CH3 or CH2OH or CHO
R5= D- glucose or D-galactose or L-rhamnose or L-arabinose or, D-xylose or alduronic acid or, D- glucuronic acid or D-galacturonic acid or H
R7=D- glucose or D-galactose or L-rhamnose or L-arabinose or, D-xylose or alduronic acid or D- glucuronic acid or D-galacturonic acid or H
R8=D- glucose or D-galactose or L-rhamnose or L-arabinose or, D-xylose or alduronic acid or D- glucuronic acid or D-galacturonic acid or H
R9= COOH or CH2OH R1 = acetyl group or H
R2 = angeloyl
R3 = angeloyl
R6 = H
R4 = CH3 or CH2OH or COOH R1 = acetyl group or H
R2 = angeloyl
R3 = angeloyl
R6 = H
R4 = CH3 or CH2OH or COOH Figure 21
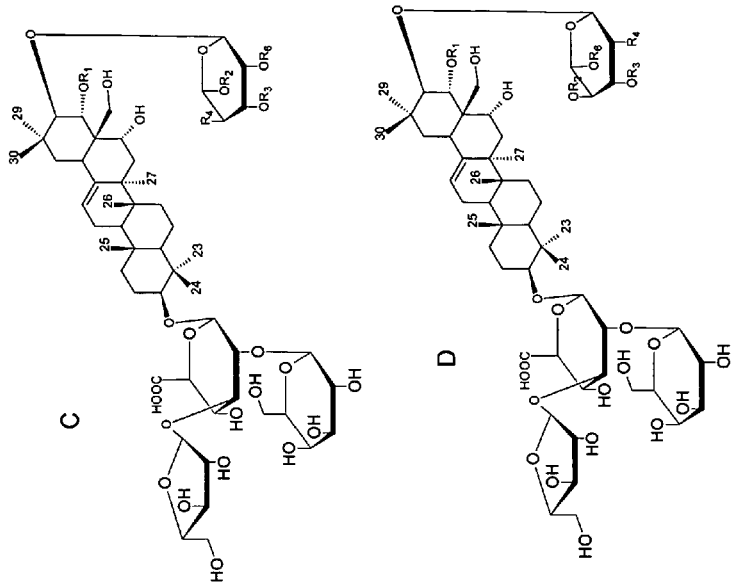
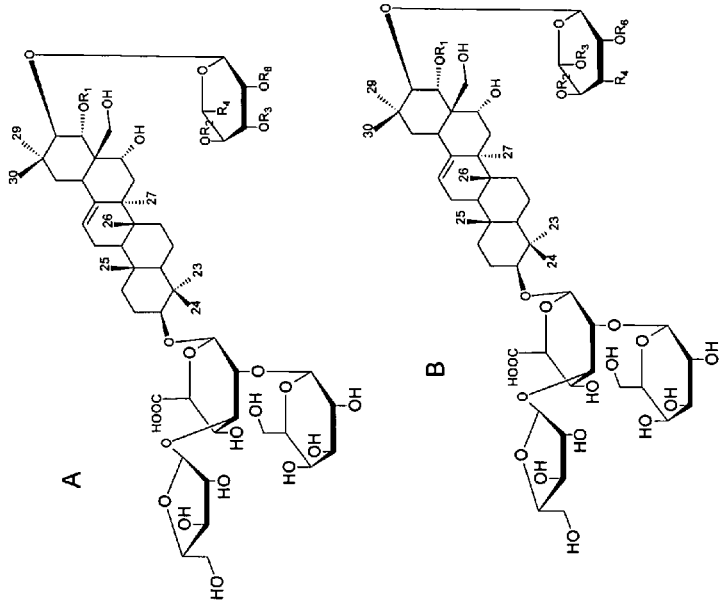
R1 = angeloyl or tigloyl or senecioly or acetyl group or H
R2 = angeloyl or tigloyl or senecioly or acetyl group or H
R3 = angeloyl or tigloyl or senecioly or acetyl group or H
R6 = H
R4 = CH3 or CH2OH or COOH
Position 23-27, 29, 30 are attached a CH3 or CH2OH or COOH or acetyl group
Positions 28 =CH3 or CH2OH or COOH or acetyl group or angeloyl or tigloyl or senecioly or sugar chains

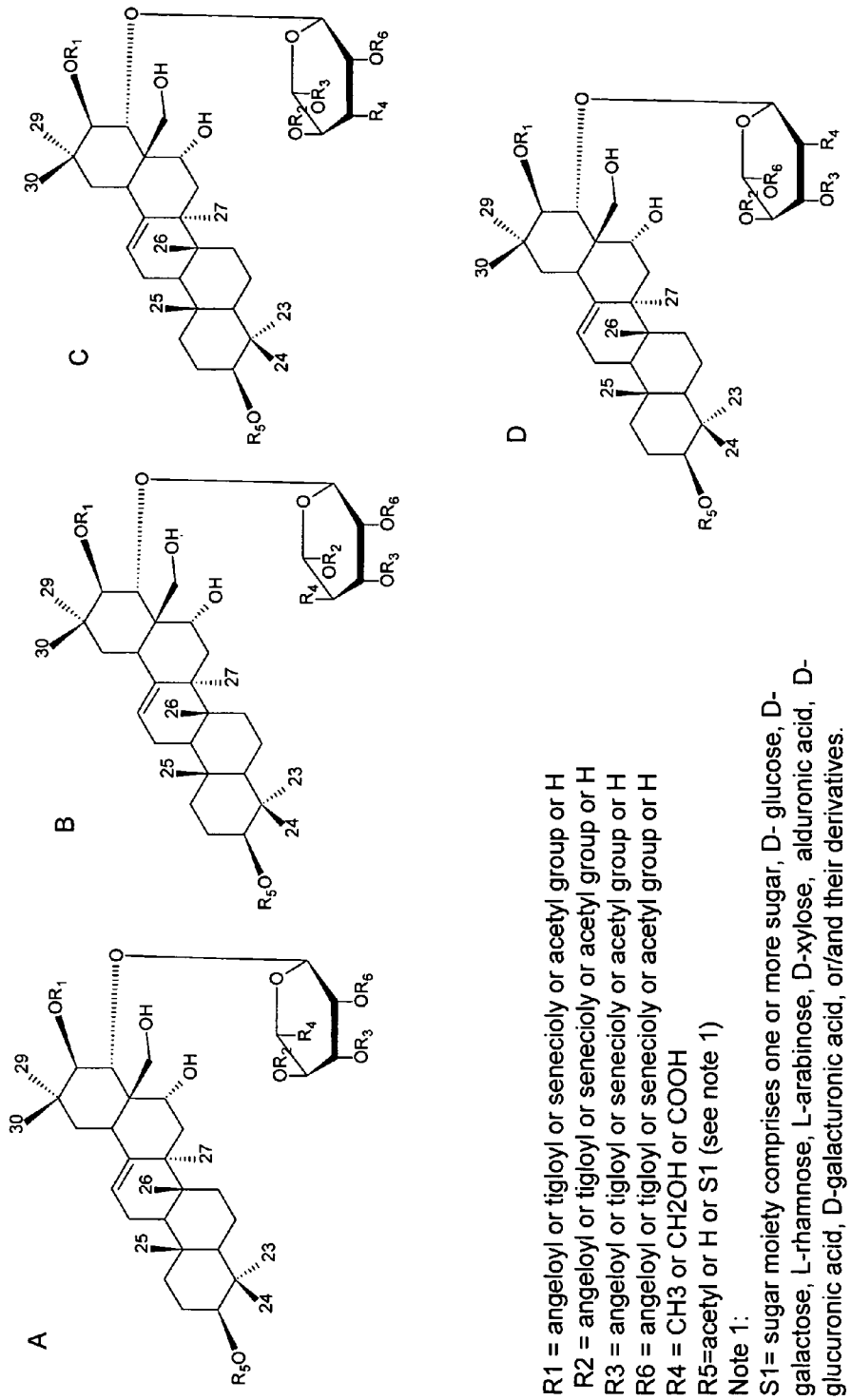

Figure 23

R1 = angeloyl or tigloyl or senecioly or acetyl group or H
R2 = angeloyl or tigloyl or senecioly or acetyl group or H
R3 = angeloyl or tigloyl or senecioly or acetyl group or H
R6 = angeloyl or tigloyl or senecioly or acetyl group or H
R4 = CH3 or CH2OH or COOH
R5=acetyl or H or S1 (see note 1)
Note 1:
S1= sugar moiety comprises one or more sugar, D- glucose, D-galactose, L-rhamnose, L-arabinose, D-xylose, alduronic acid, D-glucuronic acid, D-galacturonic acid, or/and their derivatives.
Positions 23-27, 29, 30 are attached a CH3 or CH2OH or COOH or acetyl group
Position 28 =CH3 or CH2OH or COOH or acetyl group or angeloyl or tigloyl or senecioly or sugar chains

Figure 24

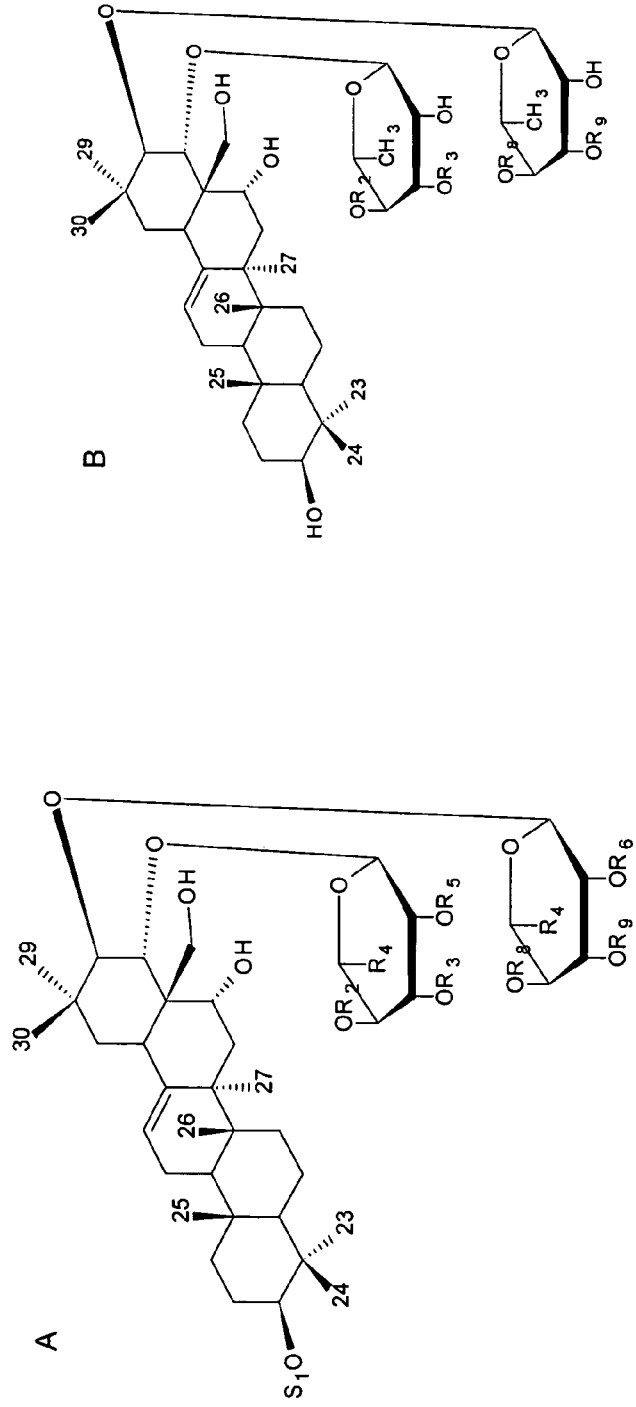

R2, R3, R5, R6, R8, R9 = angeloyl or tigloyl or senecioly or acetyl or H
R4 = CH3 or CH2OH or COOH
S1= Sugar moiety comprises one or more sugar, D- glucose, D-galactose, L-rhamnose, L-arabinose, D-xylose, alduronic acid, D- glucuronic acid, D-galacturonic acid, or/and their derivatives.
Positions 23-27, 29, 30 are attached a CH3 or CH2OH or COOH or acetyl group
Position 28 =CH3 or CH2OH or COOH or acetyl group or angeloyl or tigloyl or senecioly or sugar chains or sugar chain with angeloyl group R2, R3, R5, R6, R8, R9 = angeloyl or tigloyl or senecioly or acetyl or H
R4, R7 = CH3 or CH2OH or COOH
Positions 23-27, 29, 30 are attached a CH3 or CH2OH or COOH
Position 28 =CH3 or CH2OH or COOH or acetyl group or angeloyl or tigloyl or senecioly or sugar chains or sugar chain with angeloyl group.

Y1 and Y2 activity on Ovarian caner cells

Anticancer activity of Compounds Y, Y8, Y9 and Y10.

Haemolytic and Mtt activities of Compound Y

Structures of Y, X, ACH-Y and AKOH-Y

COMPOSITION COMPRISING TRITERPENE SAPONINS AND COMPOUNDS WITH ANGELOYL FUNCTIONAL GROUP, METHODS FOR PREPARING SAME AND USES THEREOF

This application is a Continuation-In-Part of U.S. Ser. No. 11/267,523, filed Nov. 4, 2005, now abandoned, Continuation-In-Part of International Application No. PCT/US05/31900, filed Sep. 7, 2005, Continuation-In-Part of U.S. Ser. No. 11/131,551, filed May 17, 2005, now U.S. Pat No. 7,262,285, Continuation-In-Part of U.S. Ser. No. 11/117,760, filed Apr. 27, 2005, Continuation-In-Part of U.S. Ser. No. 10/906,303, filed Feb. 14, 2005, Continuation-In-Part of International Application No. PCT/US04/43465, filed Dec. 23, 2004, which is a Continuation-In-Part of International Application No. PCT/US04/33359, filed Oct. 8, 2004, which claims the benefit of U.S. Ser. Nos. 60/532,101, filed Dec. 23, 2003, and 60/509,851, filed Oct. 9, 2003; and International Application No. PCT/US05/31900, filed Sep. 7, 2005, claims the benefit of U.S. Ser. Nos. 60/617,379, filed Oct. 8, 2004, 60/613,811, filed Sep. 27, 2004, and 60/607,858, filed Sep. 7, 2004, 60/675,282, Filed Apr. 27, 2005, and 60/675,284, Filed Apr. 27, 2005. The contents of these preceding applications are hereby incorporated in their entireties by reference into this application.

Throughout this application, various publications are referenced. Disclosures of these publications in their entireties are hereby incorporated by reference into this application in order to more fully describe the state of the art to which this invention pertains.

FIELD OF THE INVENTION

This invention relates to saponins, and compounds with angeloyl groups isolated from plants, their uses and functions, and methods of their preparations.

SUMMARY OF THE INVENTION

In accordance with these and other objects of the invention, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

This invention provides a compound comprising a triterpenoidal saponin, triterpenoid, triterpenoidal compound or sapongenin, comprising two angeloyl groups, or at least two side groups selected from the group consisting of: angeloyl groups, tigloyl groups and senecioyl groups, wherein the side groups are attached to carbon 21, 22 or/and 28 of triterpenoidal saponin, triterpenoid, triterpenoidal compound or sapongenin backbone.

This invention provides a composition for inhibiting tumor cell growth, comprising an appropriate amount of a triterpenoidal saponin, triterpenoid, triterpenoidal compound or sapongenin, wherein the triterpenoidal saponin, triterpenoid, triterpenoidal compound or sapongenin comprises two angeloyl groups or any two side groups selected from the group consisting of: angeloyl groups, tigloyl groups and senecioyl groups, wherein the side groups are attached to carbon 21 and 22 of triterpenoidal saponin, triterpenoid, triterpenoidal compound or sapongenin backbone. In an embodiment, the side groups are attached to carbon 21, 22 or/and 28 of triterpenoidal saponin, triterpenoid, triterpenoidal compound or sapongenin backbone.

This invention provides a composition for inhibiting tumor cell growth, comprising an appropriate amount of a triterpenoidal saponin, triterpenoid, triterpenoidal compound or sapongenin, wherein the triterpenoidal saponin, triterpenoid, triterpenoidal compound or sapongenin comprises two angeloyl groups or any two side groups selected from the group consisting of: angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl, wherein the side groups are attached to carbon 21 and 22 of triterpenoidal saponin, triterpenoid, triterpenoidal compound or sapongenin backbone. In an embodiment, the side groups are attached to carbon 21, 22 or/and 28 of triterpenoidal saponin, triterpenoid, triterpenoidal compound or sapongenin backbone.

The invention provides the methods and uses of triterpenoidal saponins purified and isolated from plants.

This invention provides compositions comprising the triterpenoidal saponins or their derivatives for inhibition of tumor growth. The compounds comprise angeloyl group(s) or tigloyl group(s) or senecioyl group(s) or combinations thereof which are attached to carbon 21, 22 or/and 28 of their sapongenines. In an embodiment, the compounds may comprise any two angeloyl groups or tigeloyl groups or senecioyl groups or combinations thereof attached to a sugar moiety which bonds to carbon 21 or 22 of their sapongenines. In an embodiment, the side groups are attached to carbon 21, 22 or/and 28 of triterpenoidal saponin, triterpenoid, triterpenoidal compound or sapongenin backbone.

This invention provides compositions comprising the triterpenoidal saponins or their derivatives for inhibition of tumor growth. The compounds comprise angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or combinations thereof which are attached to carbon 21, 22 or/and 28 of their sapongenines. In an embodiment, the compounds may comprise any two angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or combinations thereof attached to a sugar moiety which bonds to carbon 21 or 22 of their sapongenines. In an embodiment, the side groups are attached to carbon 21, 22 or/and 28 of triterpenoidal saponin, triterpenoid, triterpenoidal compound or sapongenin backbone.

In an embodiment, the saponin comprises a sugar moiety, wherein the sugar moiety comprises at least one sugar, or D-glucose, or D-galactose, or L-rhamnose, or L-arabinose, or D-xylose, or alduronic acid, or D-glucuronic acid or D-galacturonic acid, or their derivative thereof, or the combination thereof.

DETAILED DESCRIPTION OF THE FIGURES

FIG. 1 shows structure of saponins.
FIG. 2 shows structure of saponins.
FIG. 3 shows structure of saponins R5=B or C or S1 (see note 1)

R1=A or B or C

R2=A or B or C

R4=A or B or C

Note 1:

A=angeloyl or Tigloyl or Senecioyl

B=acetyl

C=H

S1=sugar moiety comprising one or more sugar, D-glucose, D-galactose, L-rhamnose, L-arabinose, D-xylose, alduronic acid, D-glucuronic acid, D-galacturonic acid, or their derivatives.

Positions 23-27, 29-30 are attached with CH3 or CH2OH or COOH or acetyl group

FIG. 5 shows a structure of saponins

R5=B or C or S1 (see note 1)

R1=A or B or C

R2=A or B or C

R3=A or B or C

R4=A or B or C

Note 1:

A=angeloyl or Tigloyl or Senecioyl

B=acetyl

C=H

S1=sugar moiety comprising one or more sugar, D-glucose, D-galactose, L-rhamnose, L-arabinose, D-xylose, alduronic acid, D-glucuronic acid, D-galacturonic acid, or their derivatives.

positions 23-27, 29-30 are attached with CH3 or CH2OH or COOH or acetyl group

FIG. 6 shows a structure of saponins

R5=B or C or S1 (see note 1)

R1=A or B or C

R2=A or B or C

R3=A or B or C

R4=A or B or C

Note 1:

A=angeloyl or Tigloyl or Senecioyl

B=acetyl

C=H

S1=sugar moiety comprising one or more sugar, D-glucose, D-galactose, L-rhamnose, L-arabinose, D-xylose, alduronic acid, D-glucuronic acid, D-galacturonic acid, or their derivatives.

positions 23-27, 28-30 are attached with CH3 or CH2OH or COOH or acetyl group

Figure 7:
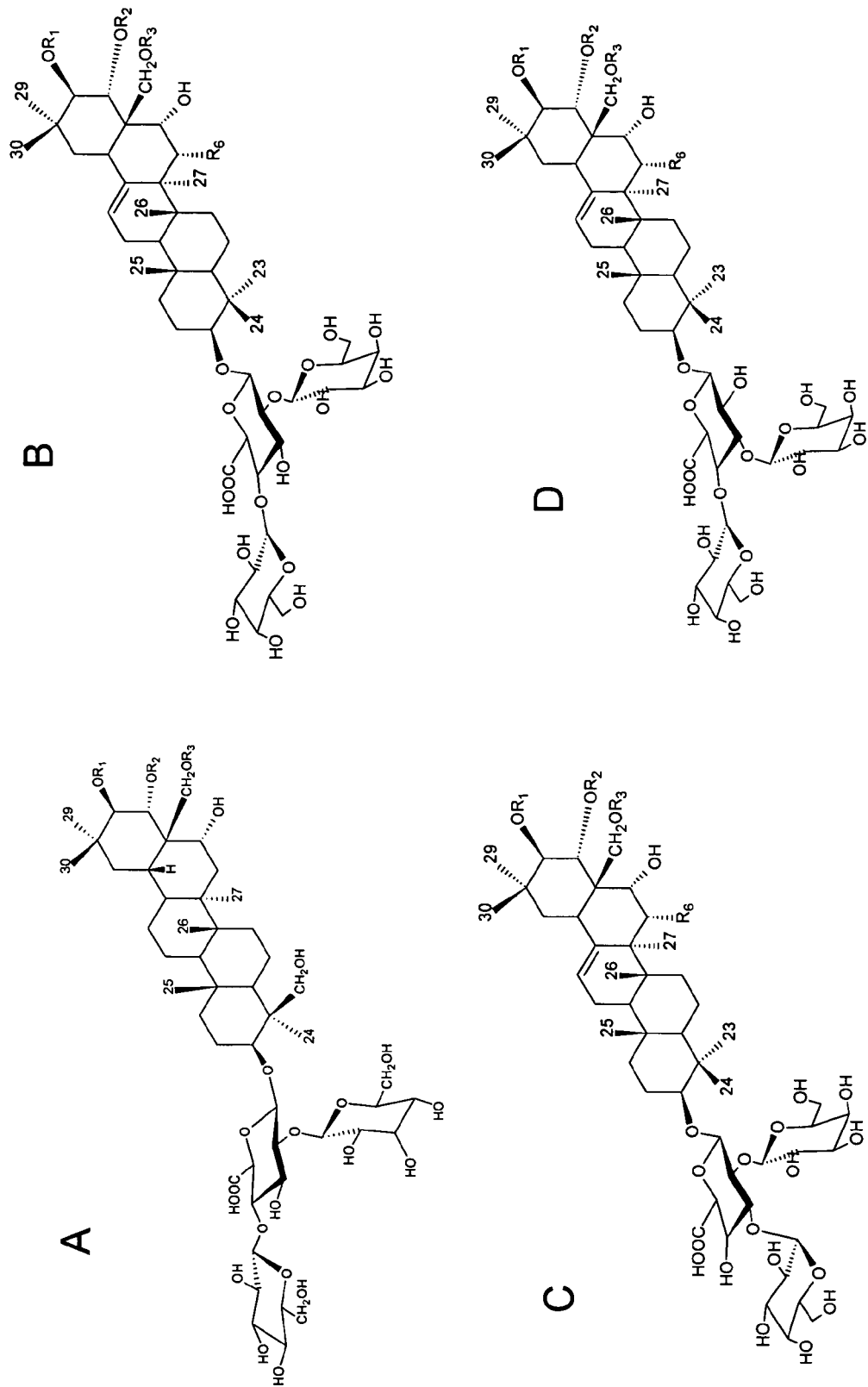

FIG. 7. A shows a structure of saponins

Wherein R1=angeloyl group or tigloyl group or senecioyl group or H.

R2=angeloyl group or tigloyl group or senecioyl group or acetyl group or H.

R3=angeloyl group or tigloyl group or senecioyl group or acetyl group or H.

FIG. 7 B, C, D shows a structure of saponins

Wherein R1=angeloyl group or tigloyl group or senecioyl group or H.

R2=angeloyl group or tigloyl group or senecioyl group or acetyl group or H.

R3=angeloyl group or tigloyl group or senecioyl group or acetyl group or H.

R6=H or OH

Positiion 23-27 and 28-30 are attached with CH3 or CH2OH or COOH or CHO

Figure 8:
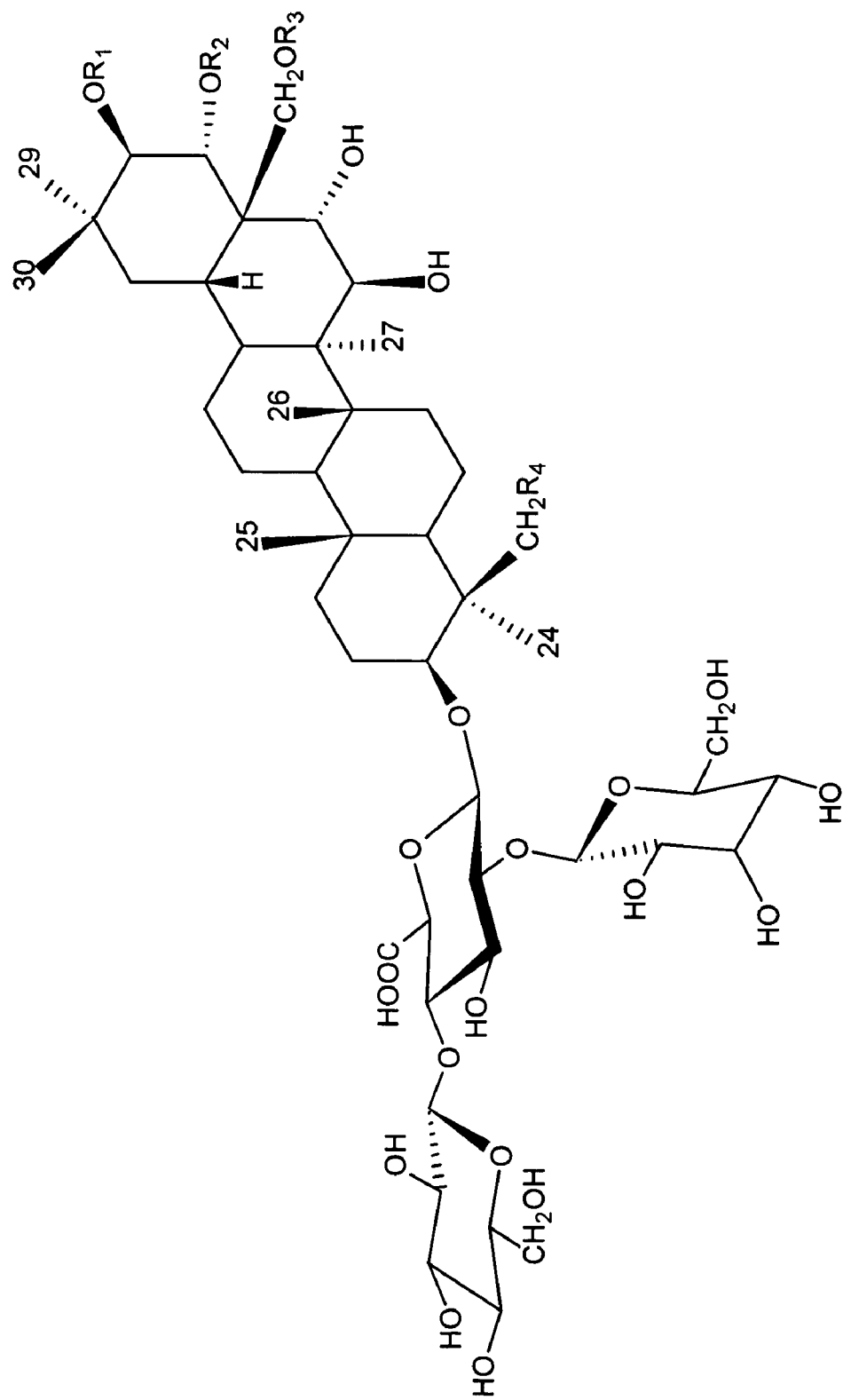

FIG. 8 shows a structure of saponins:

Wherein R1=angeloyl group or tigloyl group or senecioyl group or H.

R2=angeloyl group or tigloyl group or senecioyl group or acetyl group or H.

R3=angeloyl group or tigloyl group or senecioyl group or acetyl group or H.

R4=OH or H

Figure 9:
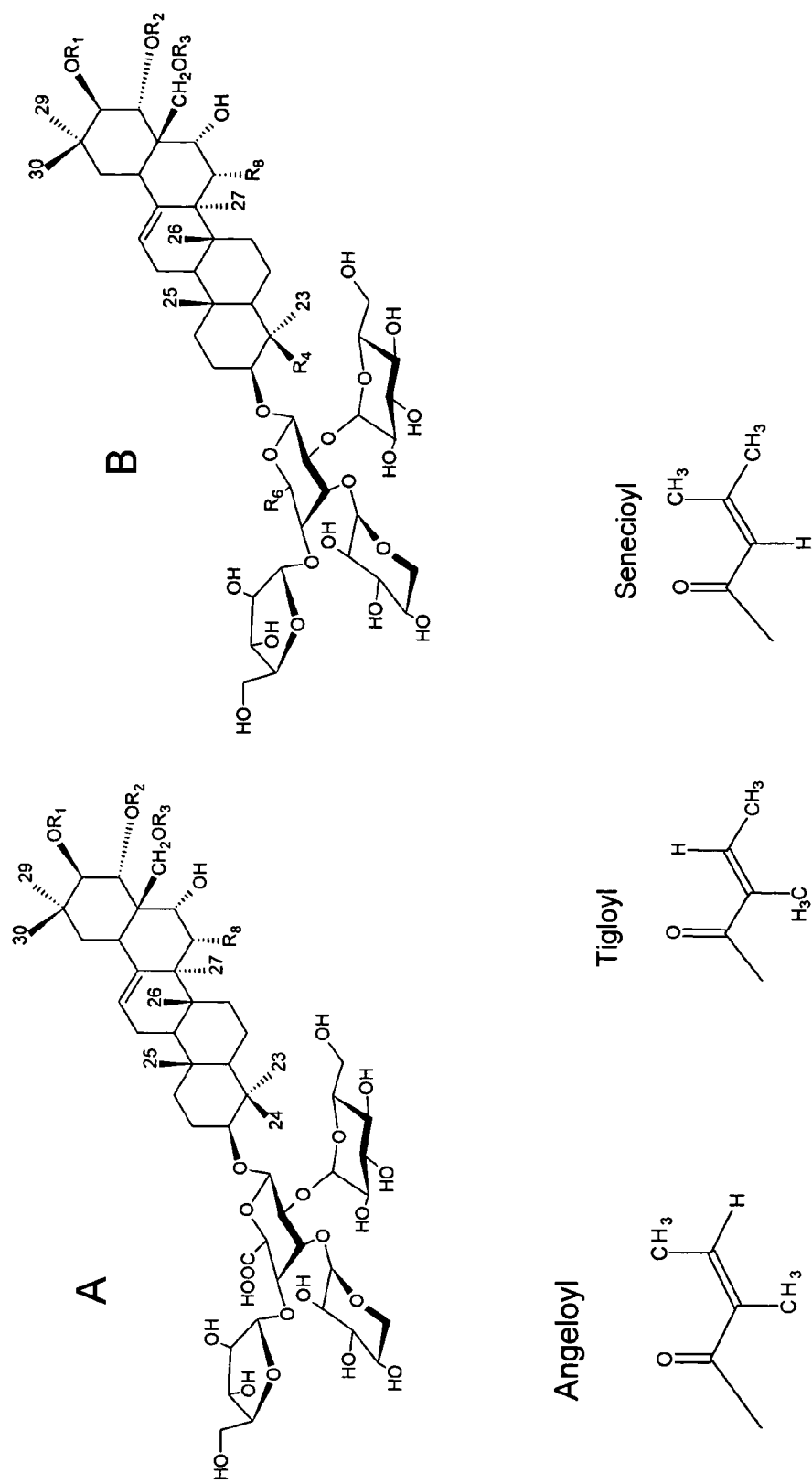

FIG. 9 A shows a structure of saponins:

Wherein R1=angeloyl group or tigloyl group or senecioyl group or acetyl group or H.

R2=angeloyl group or tigloyl group or senecioyl group or acetyl group or H.

R3=Acetyl or H.

R8=H or OH

FIG. 9 B shows a structure of saponins:

Wherein R1=angeloyl group or tigloyl group or senecioyl group or acetyl group or H.

R2=angeloyl group or tigloyl group or senecioyl group or acetyl group or H.

R3=Acetyl or H.

R4=CH3 or CH2OH or COOH

R6=CH3 or CH2OH or COOH

R8=H or OH

Figure 10:
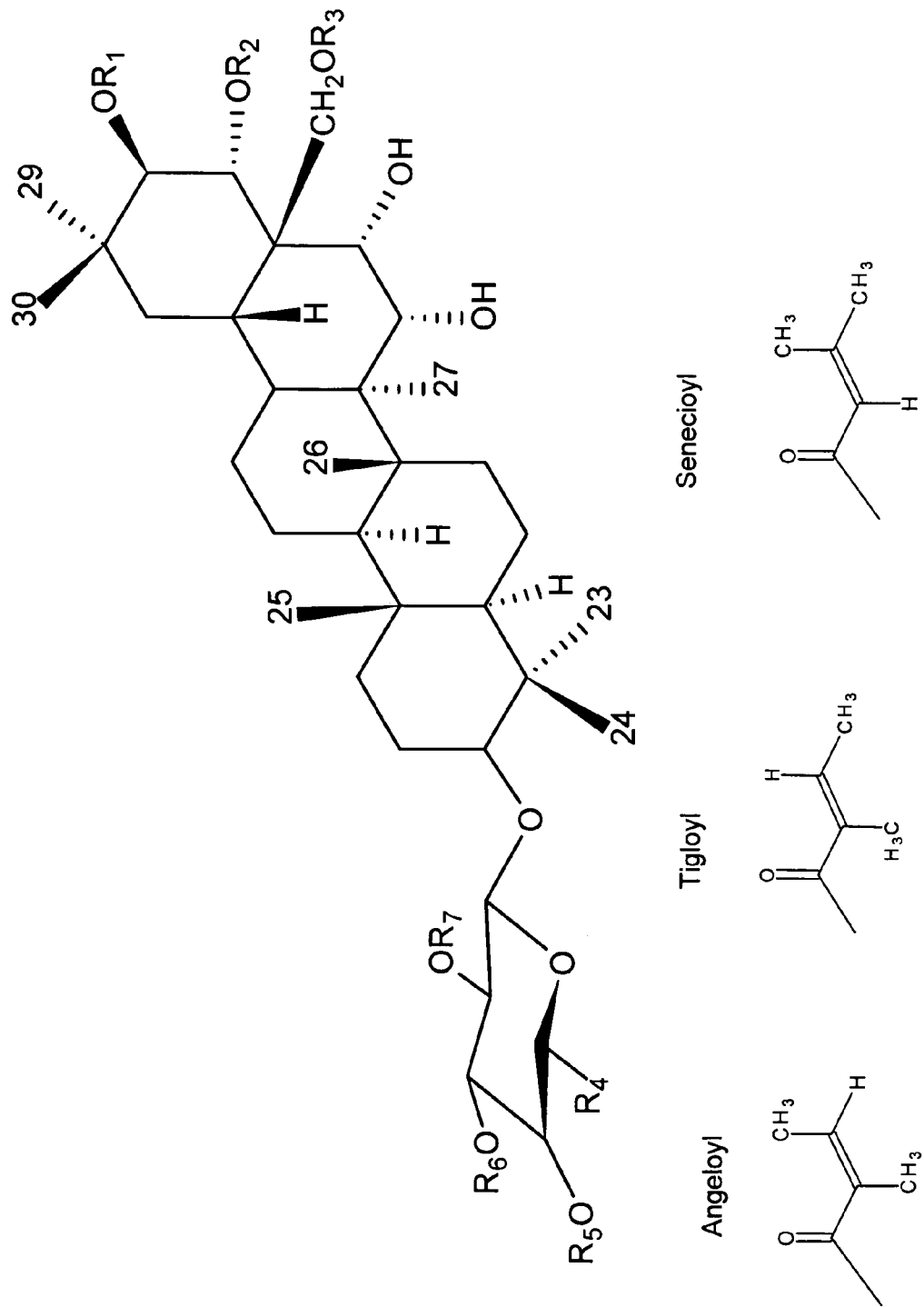

FIG. 10 shows a structure of saponins:

Wherein R1=angeloyl group or tigloyl group or senecioyl group or acetyl group or H.

R2=angeloyl group or tigloyl group or senecioyl group or acetyl group or H.

R3=Acetyl or H.

R4=COOH OR COOMe or $CH_2OH$

R5=α-L-araf and R6=α-L-arap and R7=β-D-glup; or R5, R6, and R7 is a sugar moiety, or D-glucose, or D-galactose, or L-rhamnose, or L-arabinose, or D-xylose, or alduronic acid, or D-glucuronic acid, or D-galacturonic acid, or their derivatives.

Figure 11:
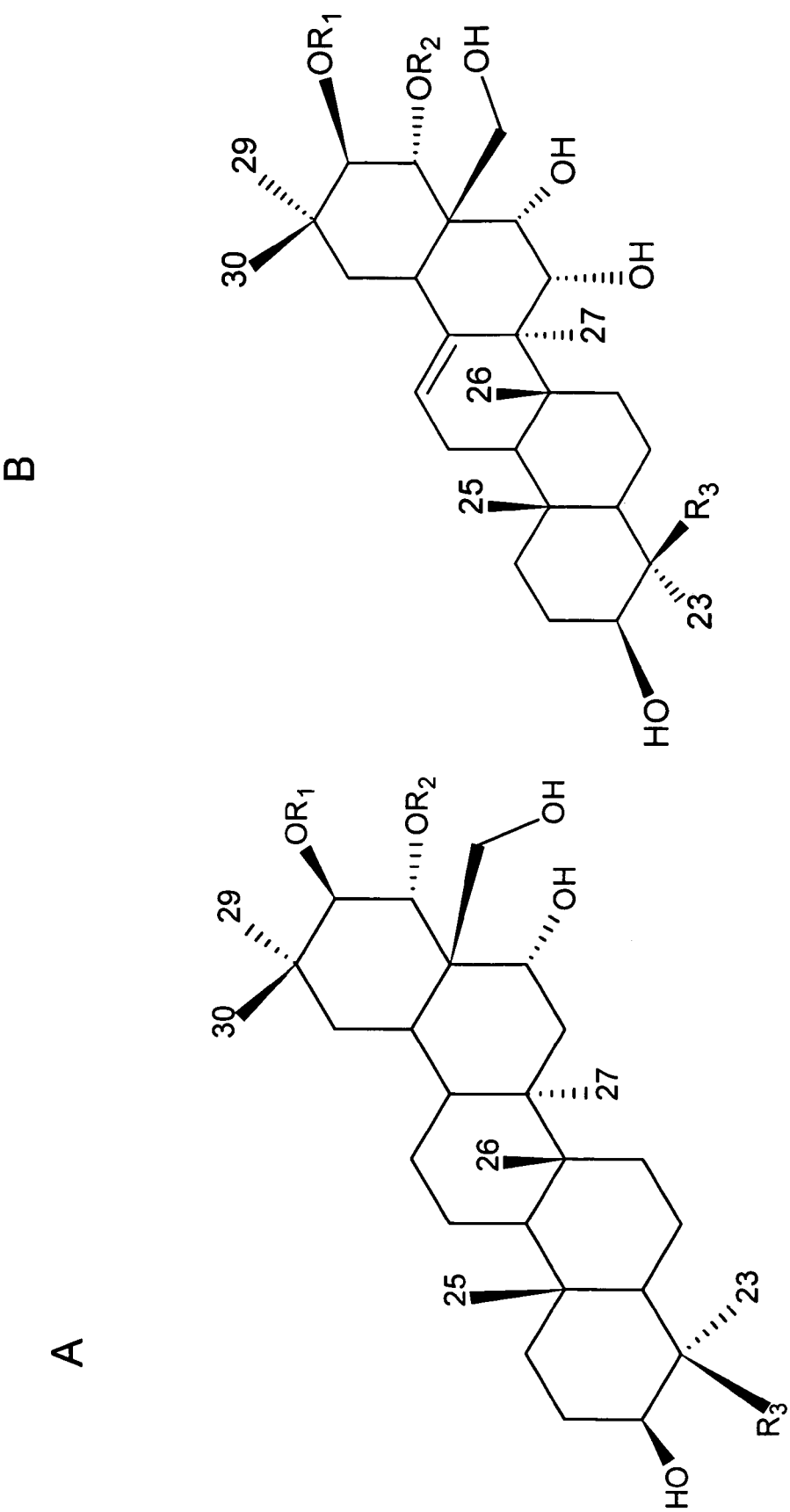

FIG. 11 A shows a structure of saponins:

Wherein R1=angeloyl group or tigloyl group or senecioyl group or acetyl group or H.

R2=angeloyl group or tigloyl group or senecioyl group or acetyl group or H.

R3=$CH_2OH$ or $CH_3$ or CHO

FIG. 11 B shows a structure of saponins:

Wherein R1=angeloyl group or tigloyl group or senecioyl group or acetyl group or H.

R2=angeloyl group or tigloyl group or senecioyl group or acetyl group or H.

R3=$CH_2OH$ or $CH_3$ or CHO

FIG. 12 A shows a structure of saponins:

Wherein R1=angeloyl group or tigloyl group or senecioyl group or acetyl group or H.

R2=angeloyl group or tigloyl group or senecioyl group or acetyl group or H.

R3=$CH_2OH$ or $CH_3$ or CHO or $COOCH_3$

R4=S1=sugar moiety comprising one or more sugar, D-glucose, D-galactose, L-rhamnose, L-arabinose, D-xylose, alduronic acid, D-glucuronic acid, D-galacturonic acid, or/and their derivatives.

FIG. 12 B shows a structure of saponins:

Wherein R1=angeloyl group or tigloyl group or senecioyl group or acetyl group or H.

R2=angeloyl group or tigloyl group or senecioyl group or acetyl group or H.

R3=$CH_2OH$ or $CH_3$ or CHO or $COOCH_3$

R4=sugar moiety comprising one or more sugar, D-glucose, D-galactose, L-rhamnose, L-arabinose, D-xylose, alduronic acid, D-glucuronic acid, D-galacturonic acid, or/and their derivatives.

Figure 13:
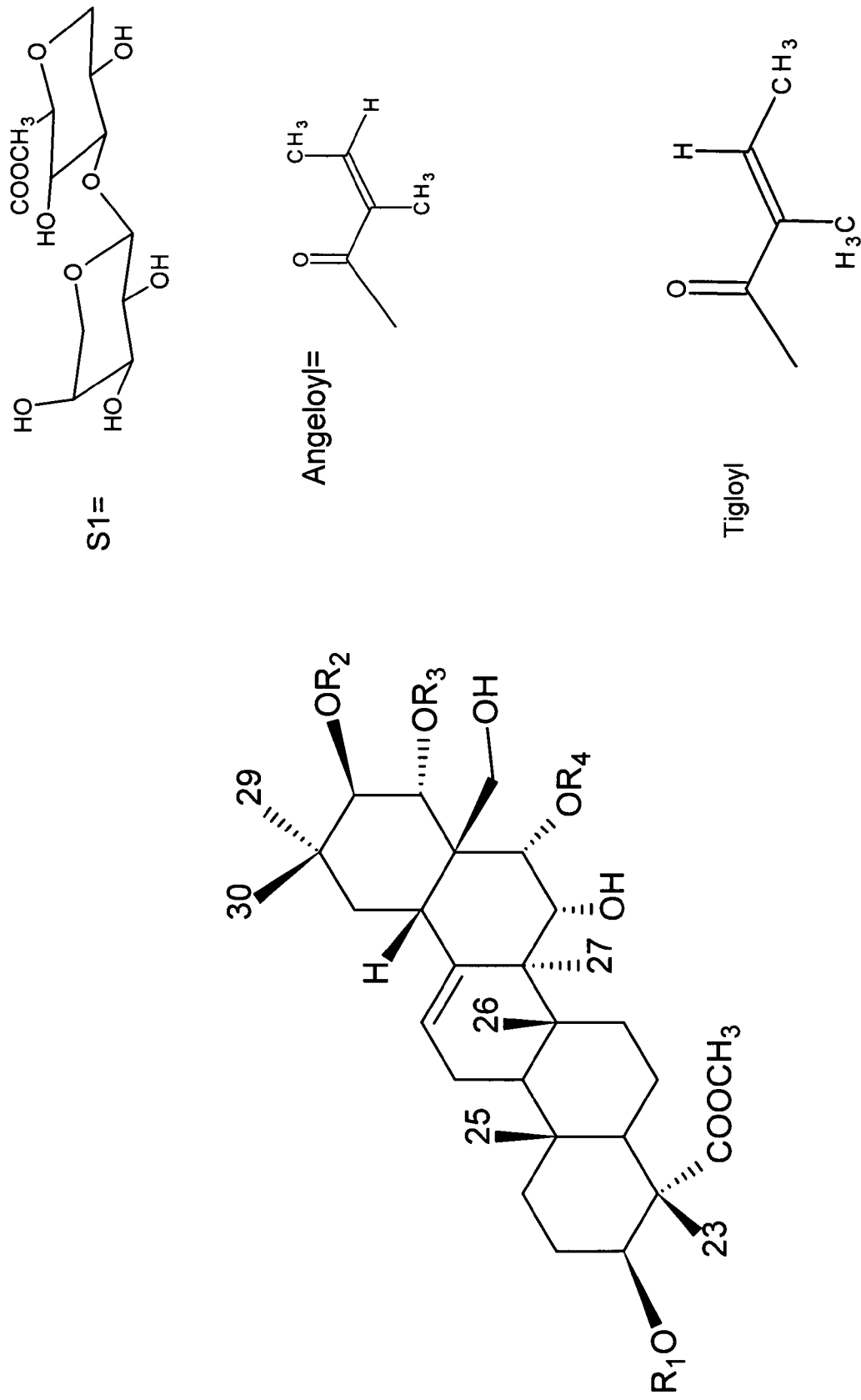

FIG. 13 shows a structure of saponins:

Wherein R2=angeloyl group or tigloyl group or senecioyl group or acetyl group or H.

R3=angeloyl group or tigloyl group or senecioyl group or acetyl group or H.

R4=$CH_2OH$ or $CH_3$ or CHO or $COOCH_3$

R1=sugar moiety comprising one or more sugar, D-glucose, D-galactose, L-rhamnose, L-arabinose, D-xylose, alduronic acid, D-glucuronic acid, D-galacturonic acid, or/and their derivatives.

Figure 14:
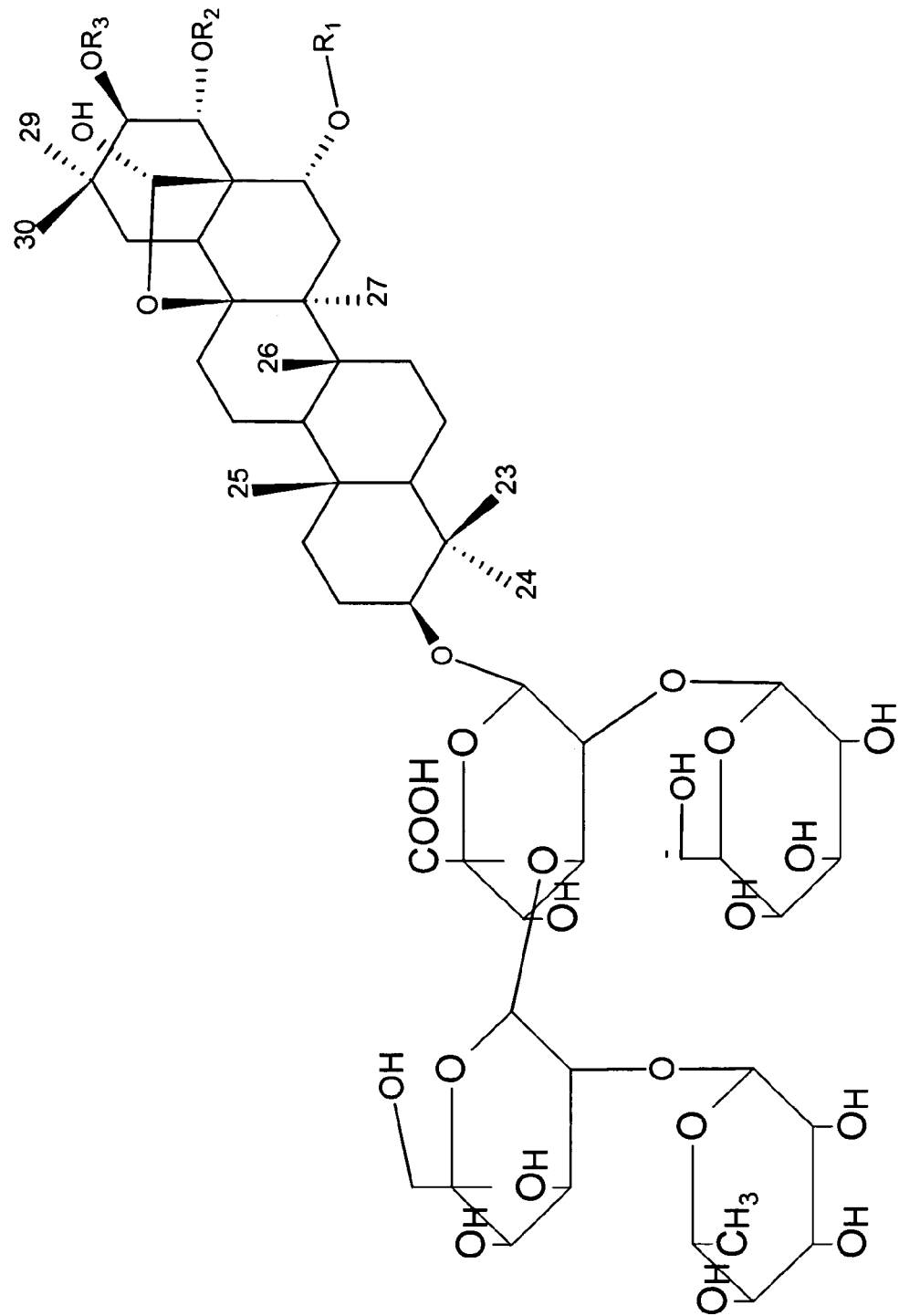

FIG. 14 shows a structure of saponins:

Wherein R1=angeloyl group or tigloyl group or senecioyl group or propanoyl or butanoly or acetyl group or H.

R2=angeloyl group or tigloyl group or senecioyl group or propanoyl or butanoly or acetyl group or H.

R3=angeloyl group or tigloyl group or senecioyl group or propanoyl or butanoly or acetyl group or H.

R4=sugar moiety comprising one or more sugar, D-glucose, D-galactose, L-rhamnose, L-arabinose, D-xylose, alduronic acid, D-glucuronic acid, D-galacturonic acid, or/and their derivatives.

Figure 15:
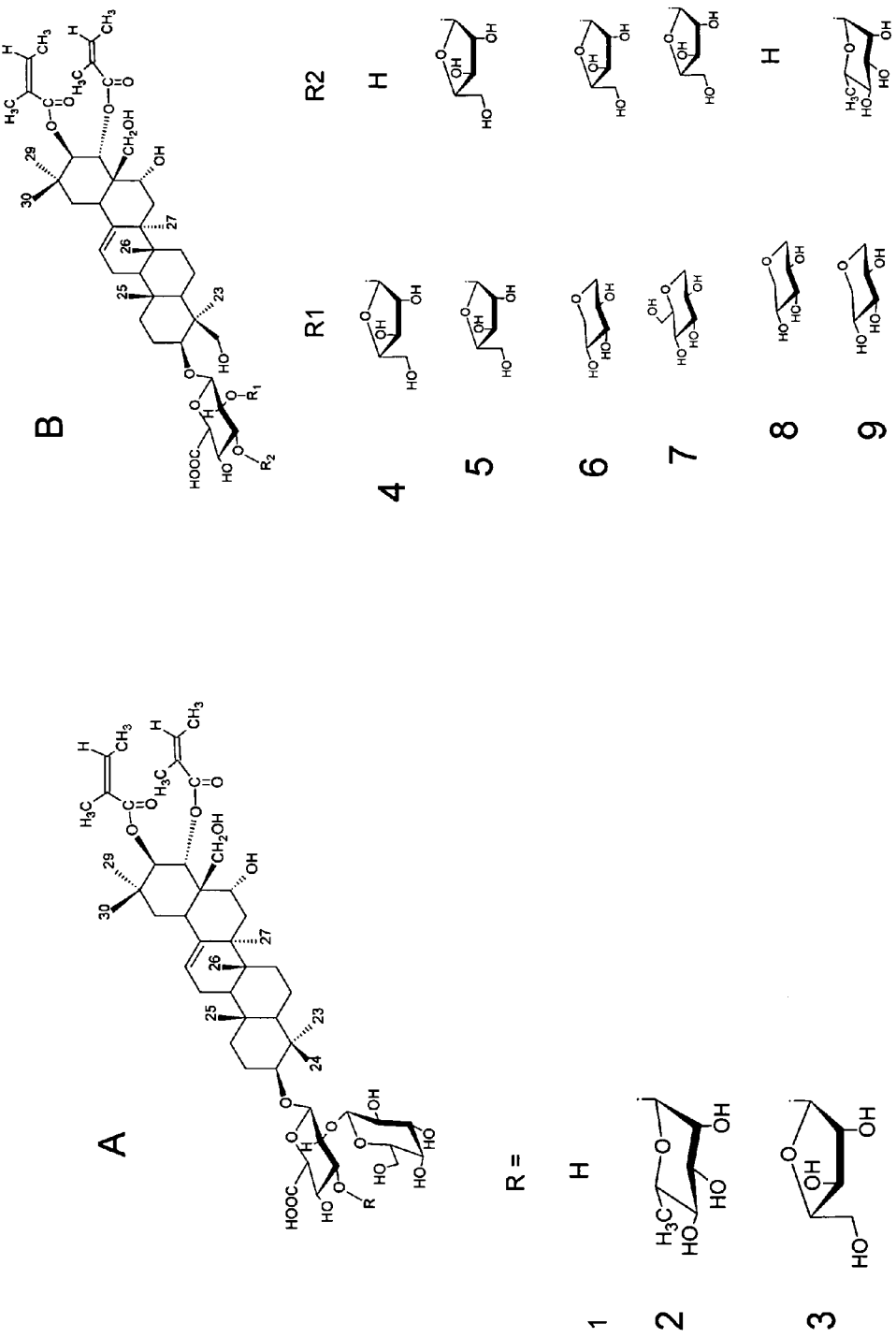

FIG. 15 shows a structure of saponins

FIG. 16 A, 16 B shows a structure of saponins

R1=angeloyl or Tigloyl or Senecioyl or acetyl or H

R2=angeloyl or Tigloyl or Senecioyl or acetyl or H

R6=angeloyl or Tigloyl or Senecioyl or acetyl or H

R3=H or OH

R10=CH3 or CH2OH or CHO

Figure 17:
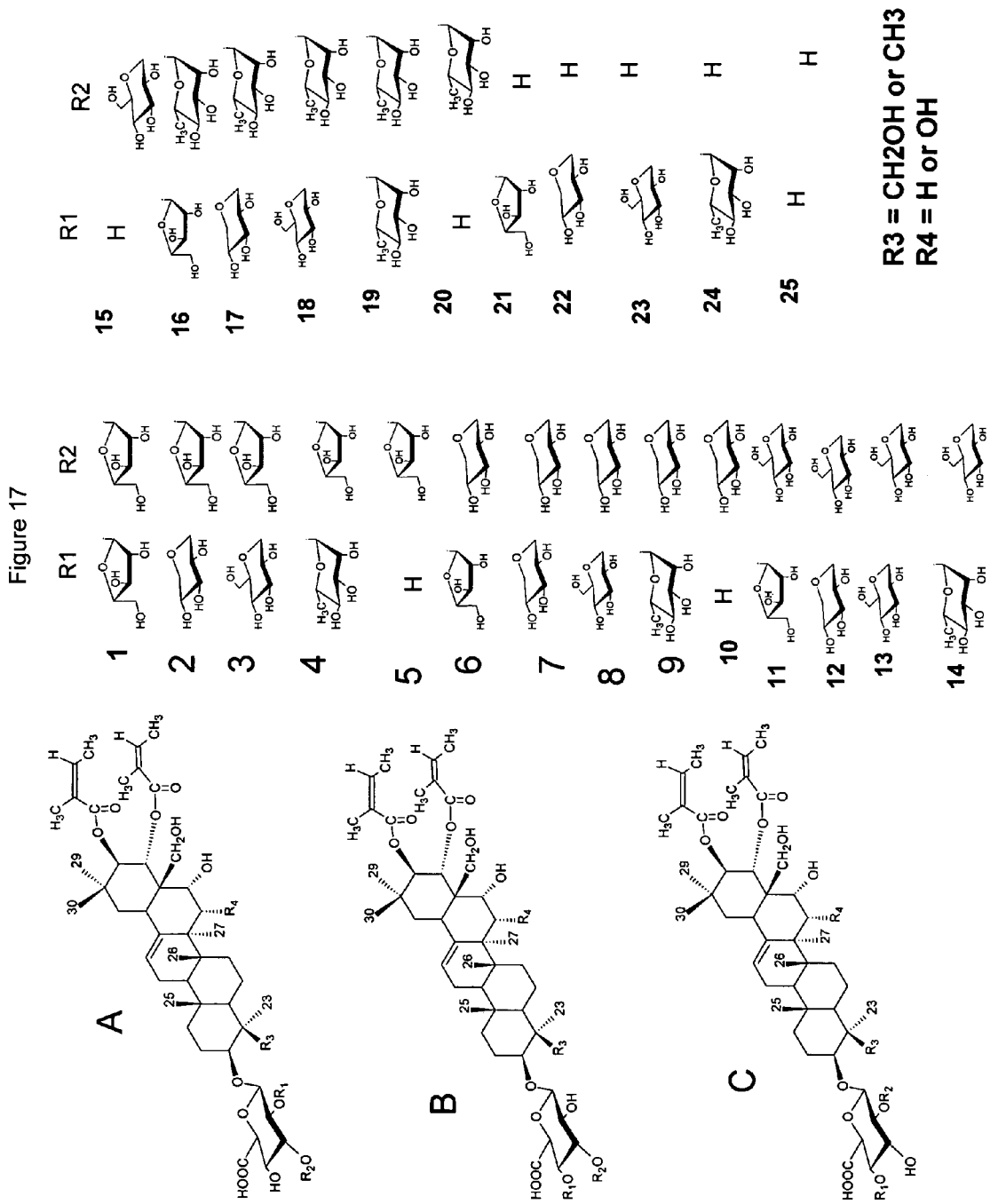
Figure 18:
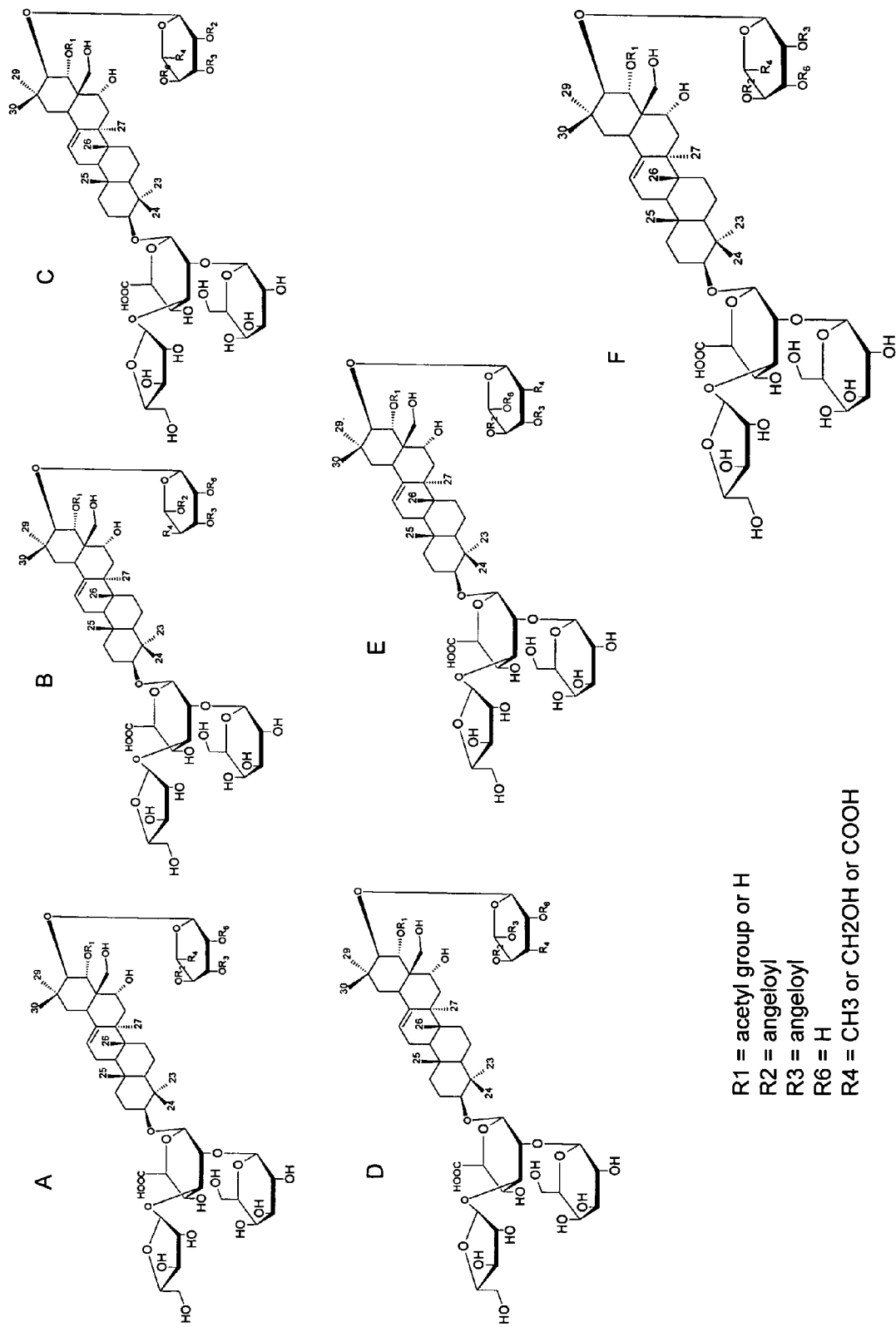
Figure 19:
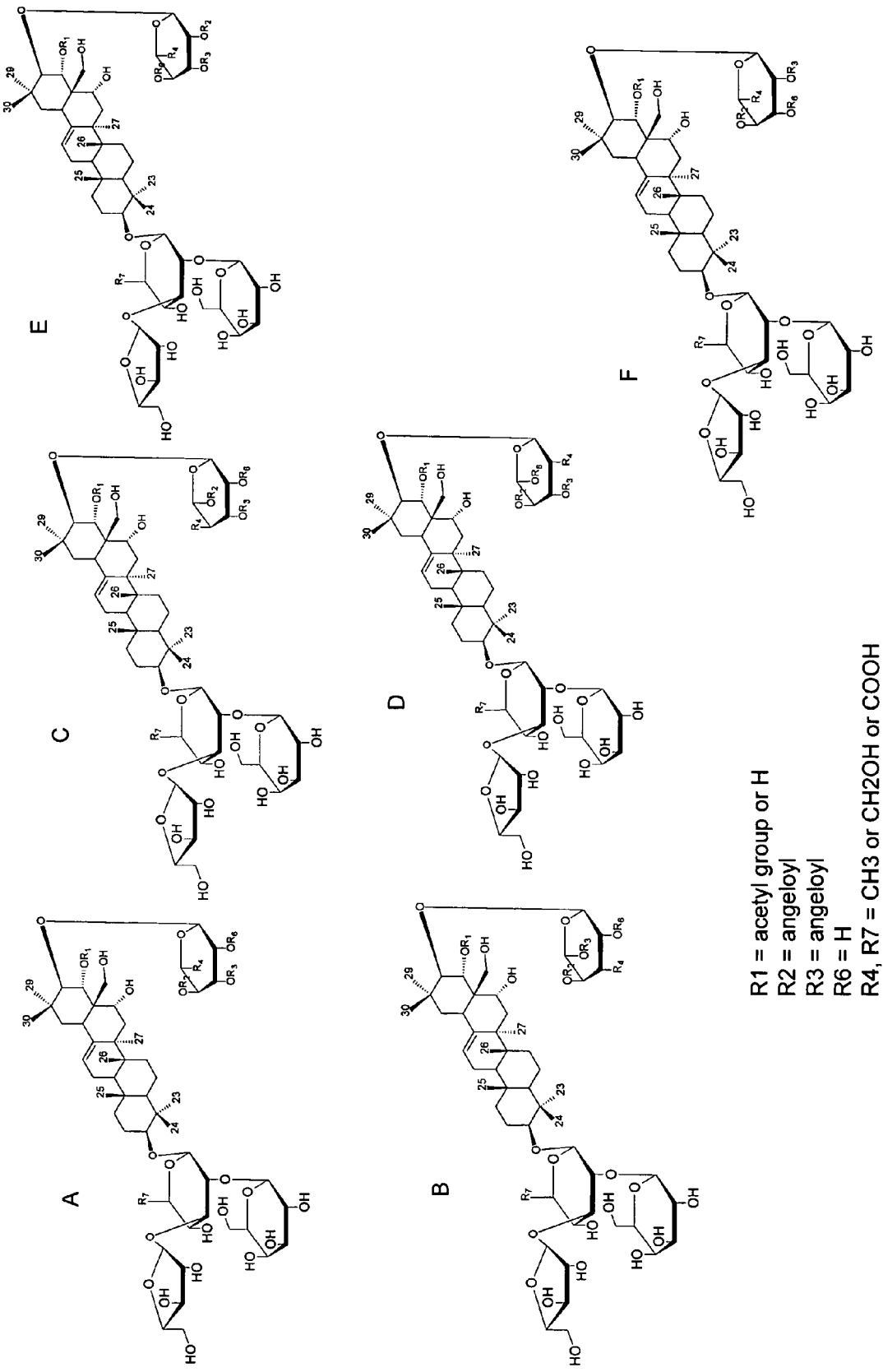
Figure 20:
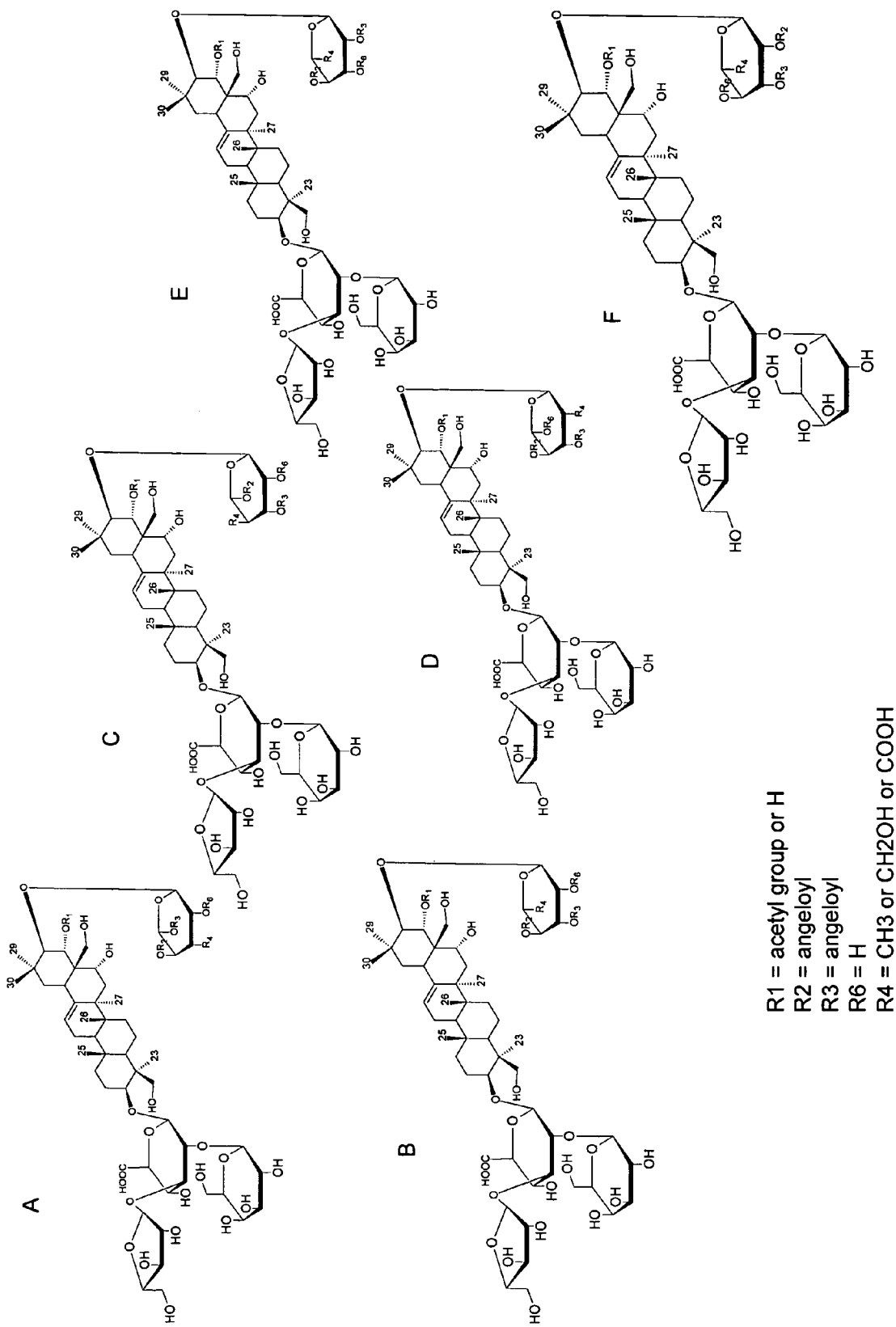
Figure 22:
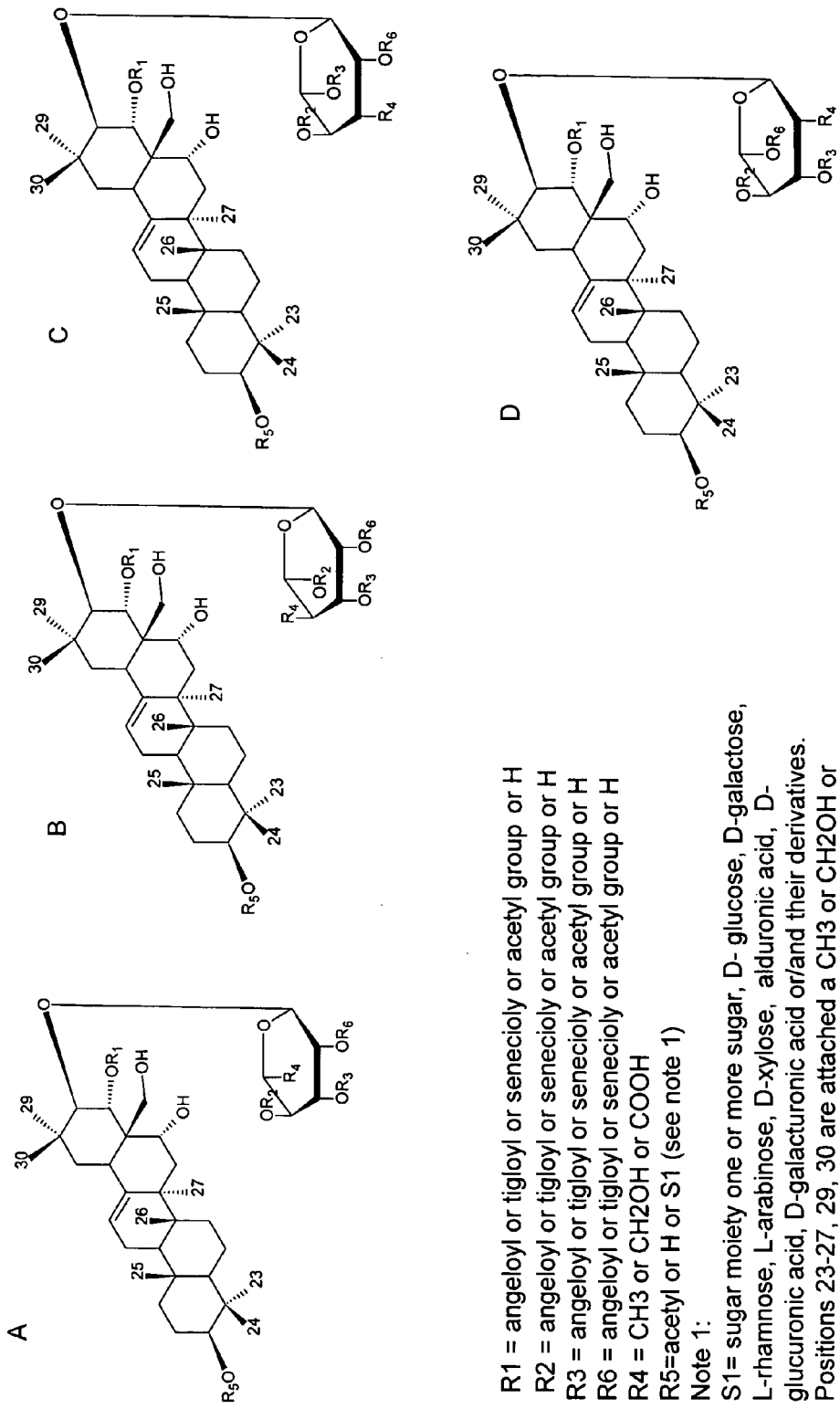
Figure 25:
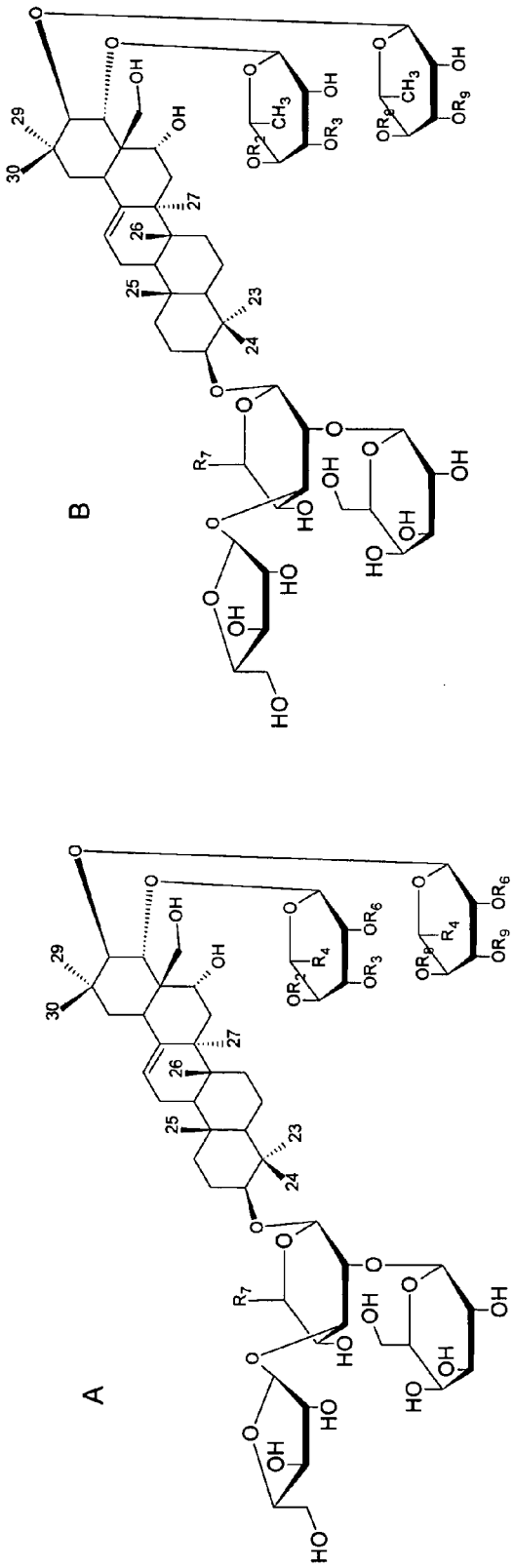
Figure 26:
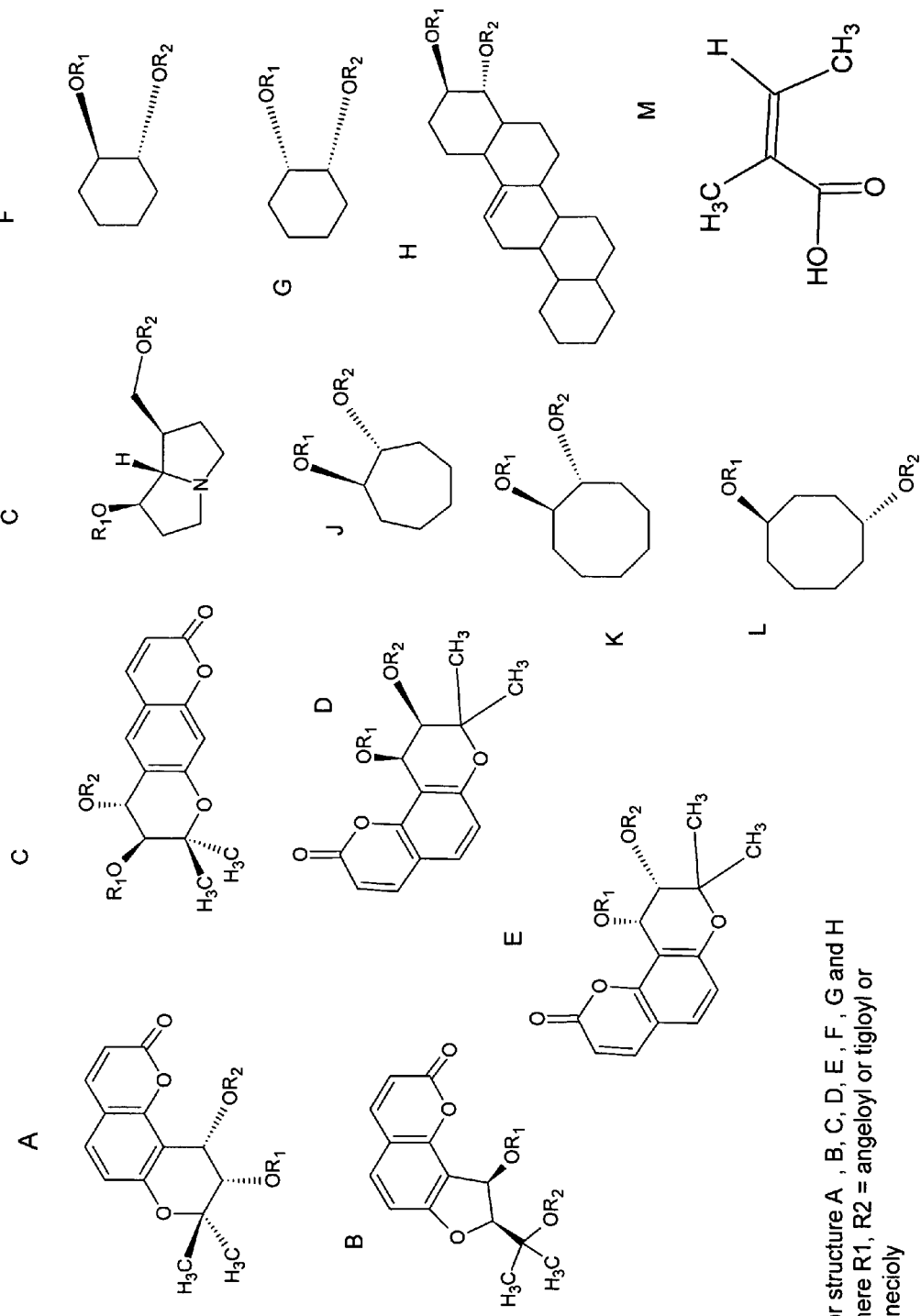
Figure 27:
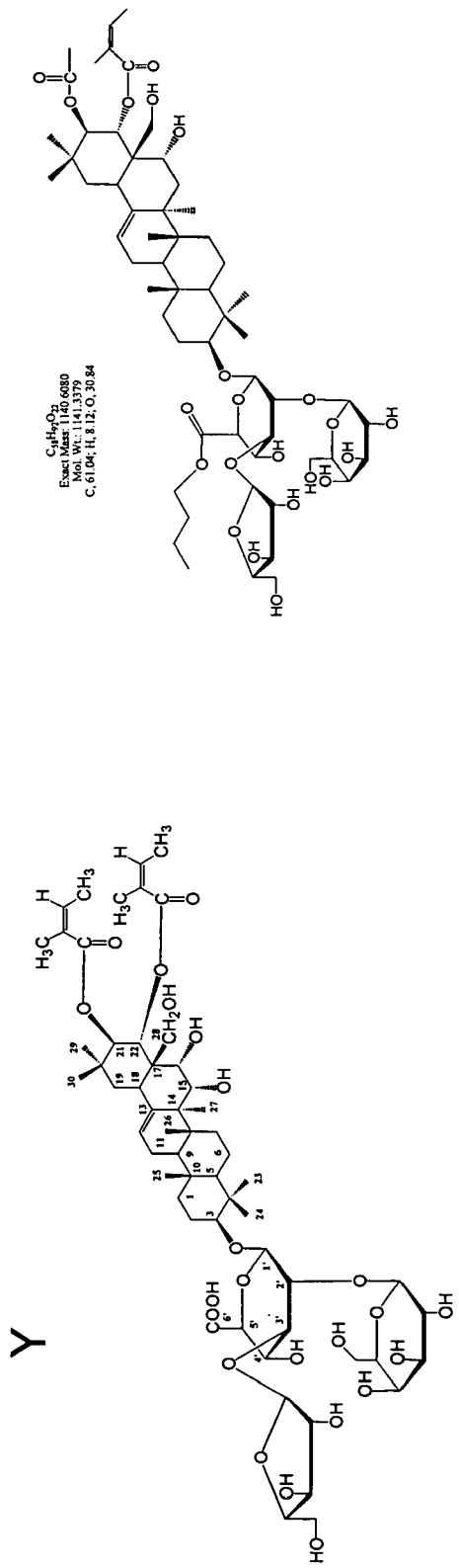
Figure 28:
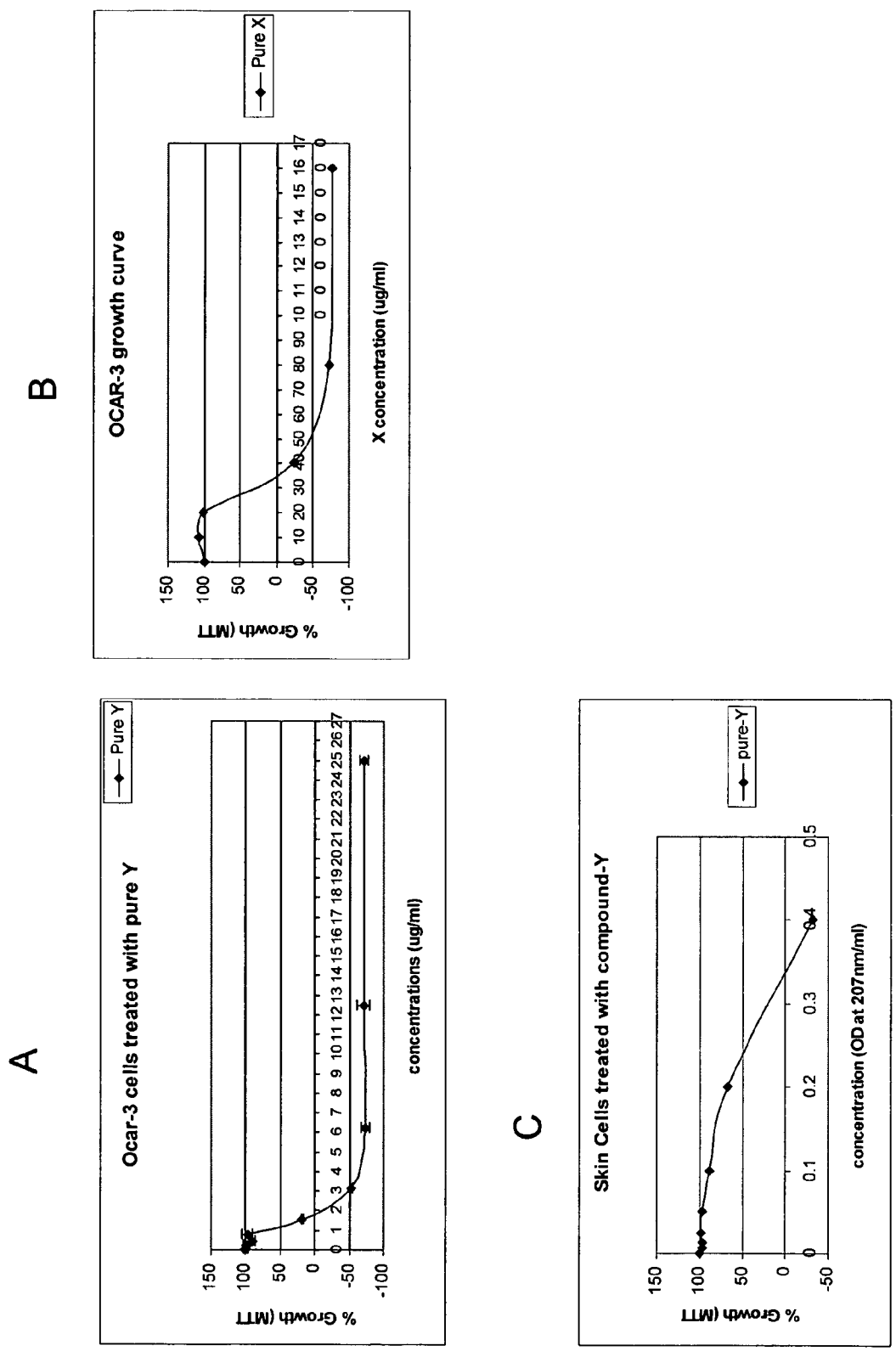

R5=D-glucose or D-galactose or L-rhamnose or L-arabinose or, D-xylose or alduronic acid or D-glucuronic acid or D-galacturonic acid or H R7=D-glucose or D-galactose or L-rhamnose or L-arabinose or, D-xylose or alduronic acid or D-glucuronic acid or D-galacturonic acid or H R8=D-glucose or D-galactose or L-rhamnose or L-arabinose or, D-xylose or alduronic acid or D-glucuronic acid or D-galacturonic acid or H R9=COOH or CH2OH FIG. 17 shows a structure of saponins FIG. 18 shows a structure of saponins FIG. 19 shows a structure of saponins FIG. 20 shows a structure of saponins FIG. 21 shows a structure of saponins FIG. 22 shows a structure of saponins FIG. 23 shows a structure of saponins FIG. 24 shows a structure of saponins FIG. 25 shows a structure of saponins FIG. 26 shows a structure of compounds with angeloyl groups FIG. 27 shows a structure of saponins FIGS. 28 A and B shows the comparison of potency of Compound Y (saponin with 2 angeloyl groups) and compound X (saponin with 1 angeloyl) in ovarian cancer cells. The IC50 for Compound Y in ovary cells is about 1.5 ug/ml while the IC50 for compound X is 30 ug/ml.

FIG. 28 C shows the inhibition of the purified Compound Y on the growth of skin cancer cell. The IC50 is 0.23 ug/ml.

Figure 29:
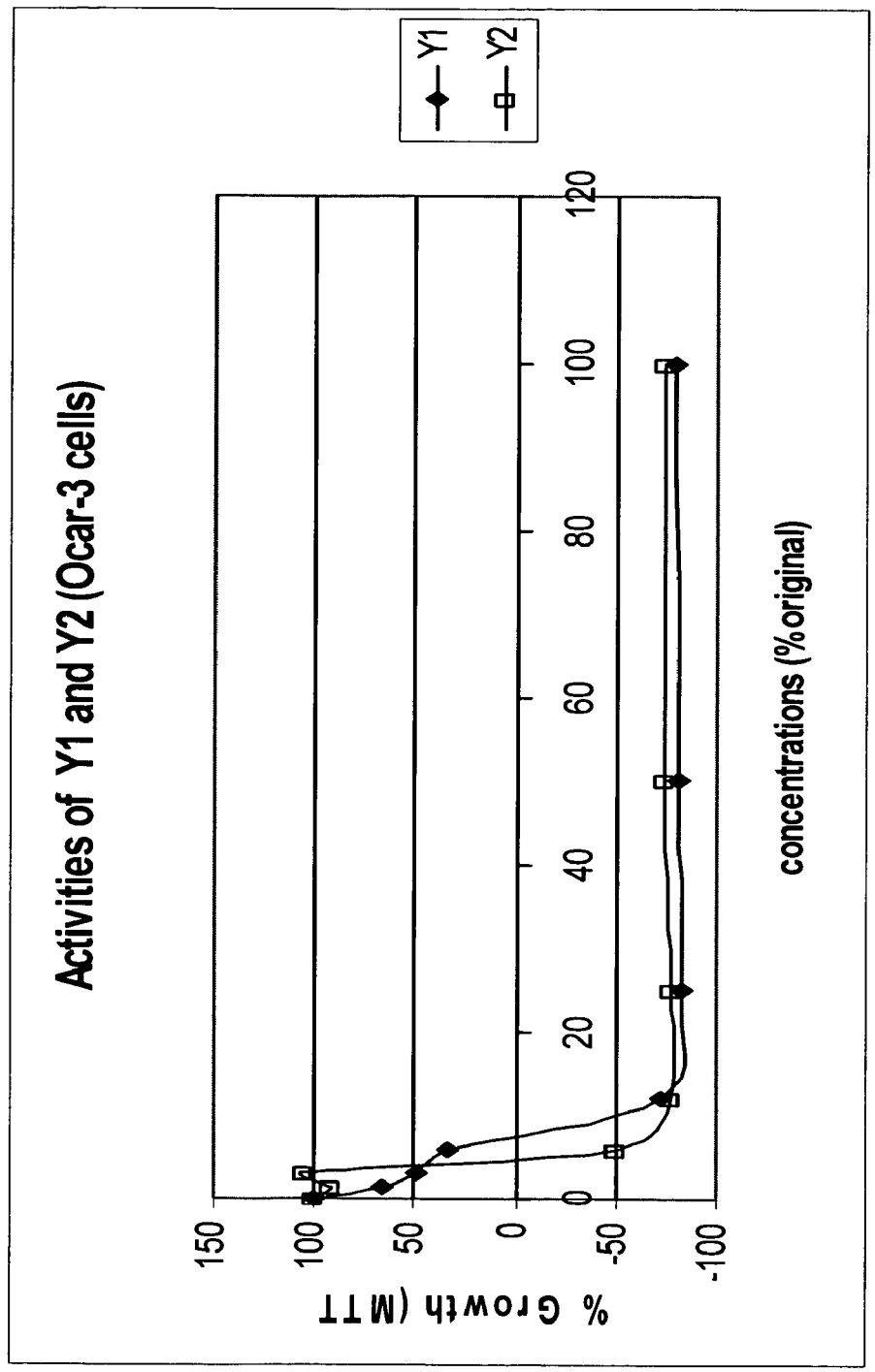

FIG. 29 shows the inhibition of the purified Compound Y1 and Compound Y2 on the growth of ovarian cancer cells.

Figure 30:
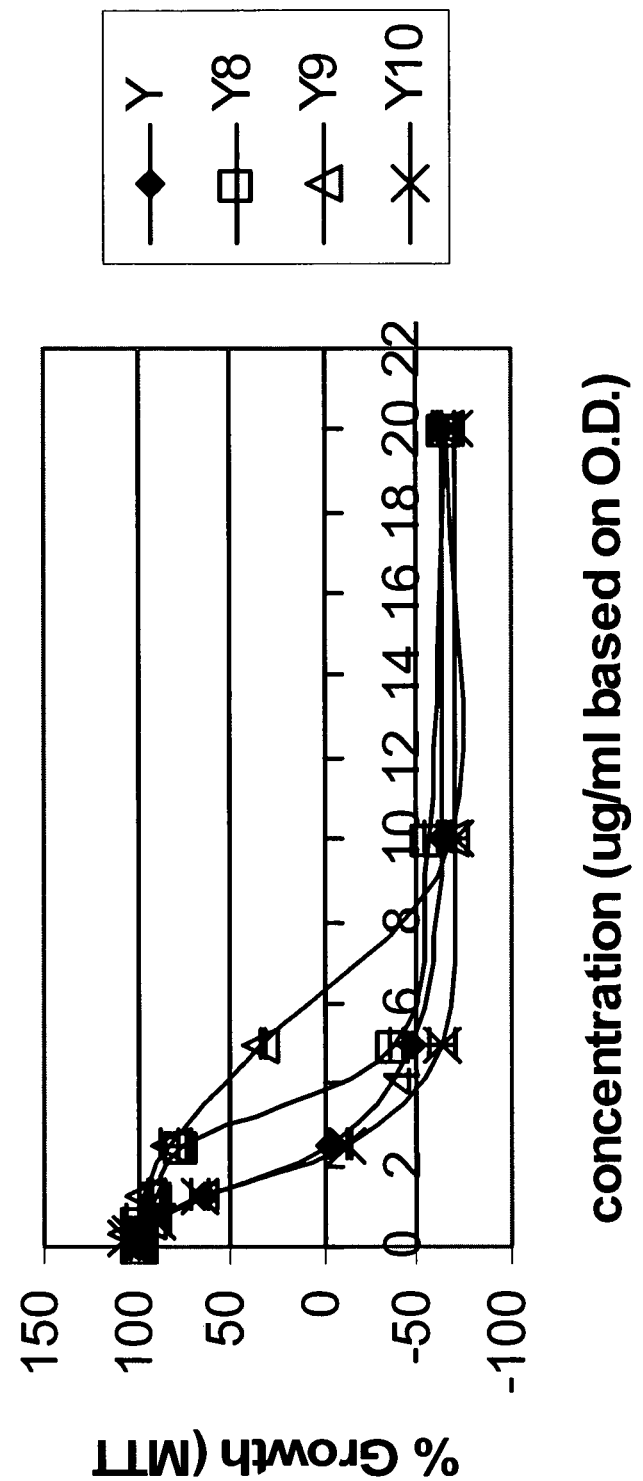

FIG. 30 shows the anticancer activity of Y, Y8, Y9 and Y10 on ovarian cancer cells as determined by MTT assay.

Figure 31:
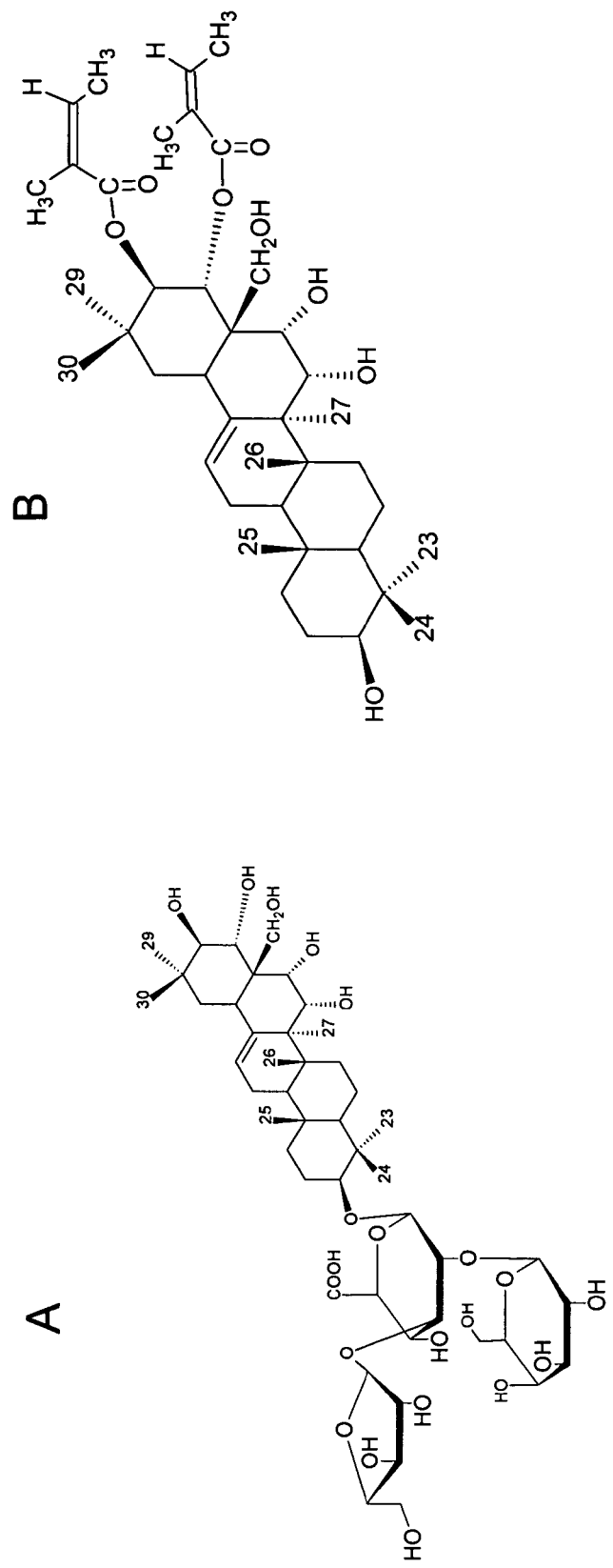

FIG. 31 (A) shows a compound of the invention without angeloyl groups. (B) shows a compound of the invention without sugar moiety.

Figure 32:
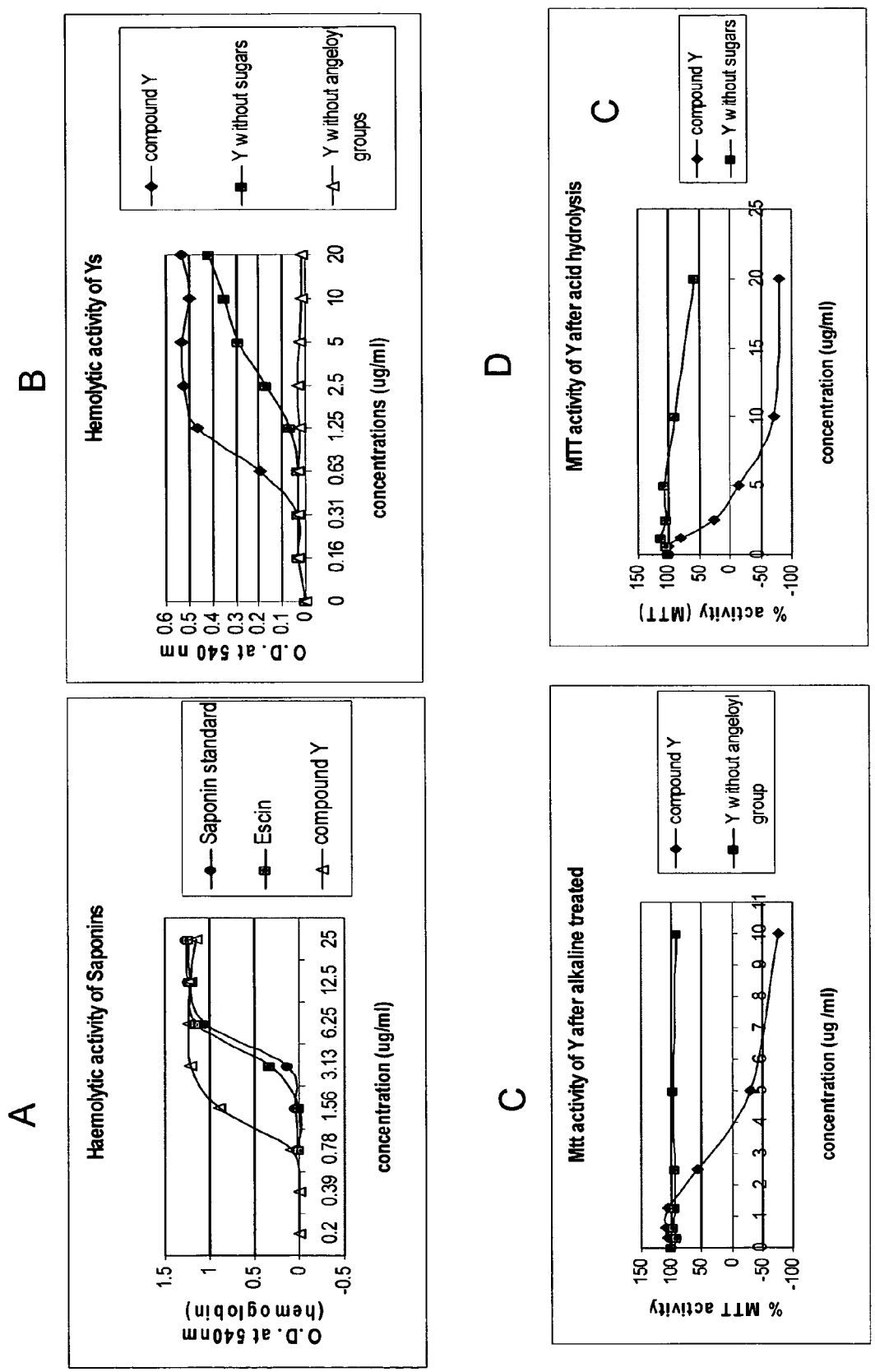

FIG. 32 shows a comparision of MTT and Haemolytic activities of saponin compound and Compound Ys of the invention. (A) and (B) shows hemolytic activities. (C) and (D) show MTT activities.

Figure 33:
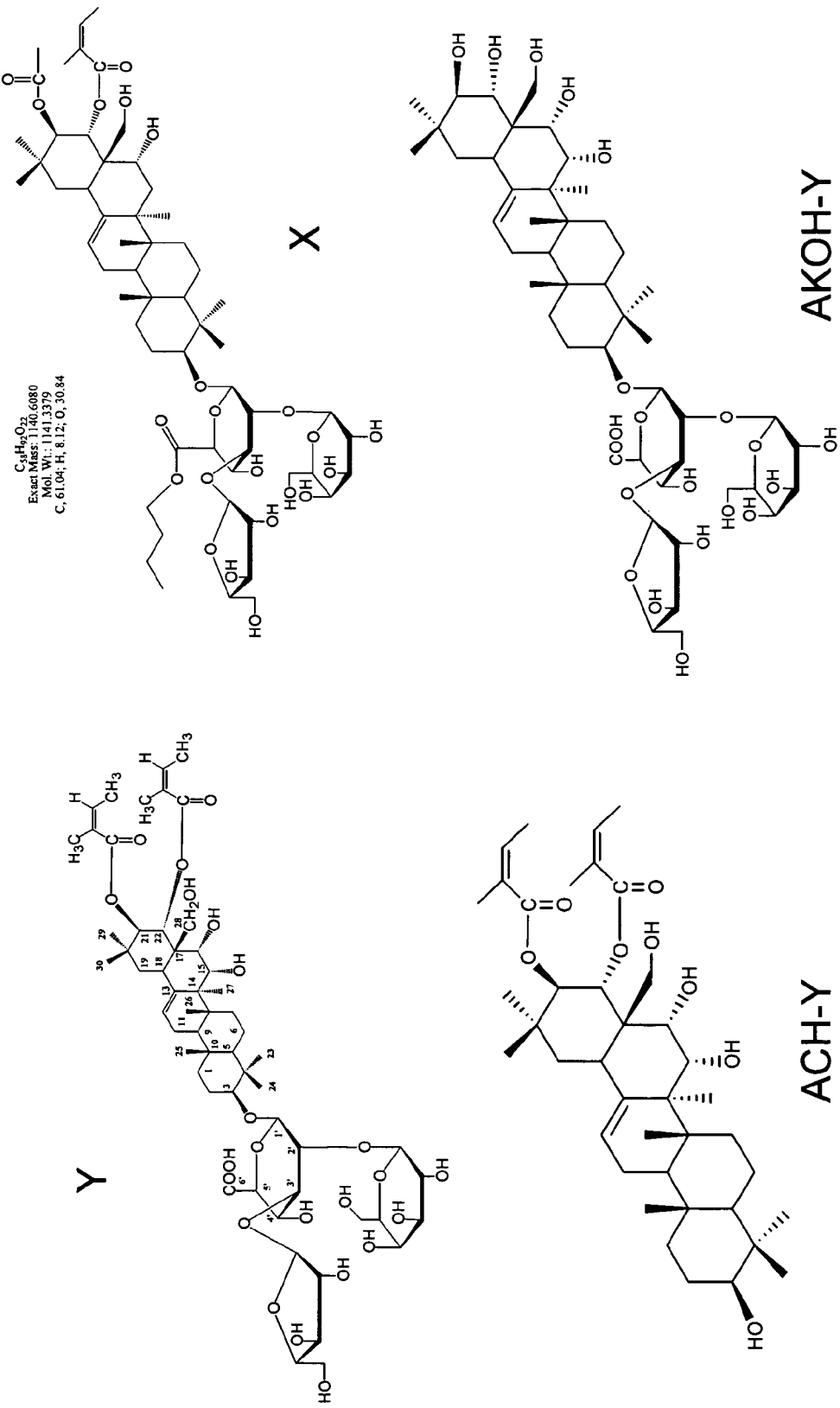

FIG. 33 shows the saponin compounds Y, X ACH-Y, AKOH-Y of the invention. These compounds are purified and their structures were verified by NMR and MS. These compounds are then used for cell growth inhibition studies (MTT).

Figure 34:
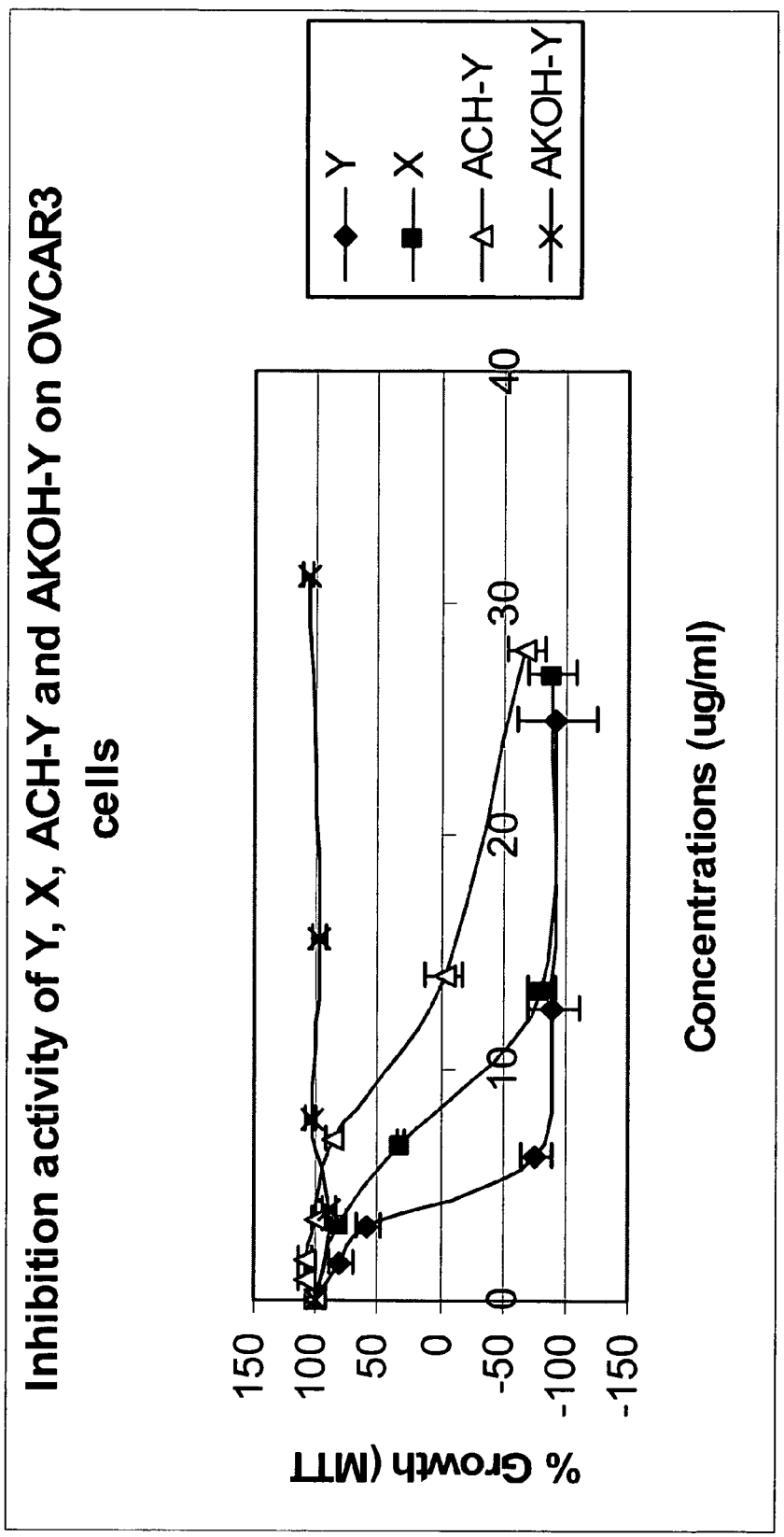

FIG. 34 The experiment results show that Y inhibits tumor growth (with IC50=4 ug/ml). Compound X which has a similar structure to Y but with only one angeloyl group at C22, has less activity (IC50=6 ug/ml) than Y. Removal of sugars from Y (ACH-Y) but retaining the diangeloyl group retains 40% of activity (IC50=9.5 ug/ml). However, removal of both angeloyl groups from C21 and C22 of Y (AKOH-Y) completely abolishes its activity (no activity even at 120 ug/ml). Results indicate that diangeloyl groups in compound Ys are important for anti-tumor activity.

DETAILED DESCRIPTION OF THE INVENTION

This invention describes the results of a program of screening the bioactive compounds from natural plants. Most of the plants are in Sapindaceae family, which has 1400-2000 species with 140-150 genera. The program of screening for bioactive compounds is based on our purification methods and biological assays including the MTT assay.

The invention provides methods and uses of saponins including triterpenoidal saponins purified or isolated from plants in the following genus:

*Acer, Aesculus, Alectryon, Allophylus, Allosanthus, Amesiodendron, Aphania, Aporrhiza, Arfeuillea, Arytera, Atalaya, Athyana, Averrhoidium, Blighia, Boniodendron, Camellia, Camptolepis, Cardiospermum, Castanospora, Chonopetalum, Chouxia, Chytranthus, Conchopetalum, Cossinia, Cubilia, Cupania, Cupaniopsis, Deinbollia, Delavaya, Diatenopteryx, Dictyoneura, Dilodendron, Dimocarpus, Diploglottis, Diplokelepa, Diplopeltis, Dipteronia, Distichostemon, Dodonaea, Doratoxylon, Elattostachys, Eriocoelum, Erioglossum, Erythrophysa, Euchorium, Euphorianthus, Eurycorymbus, Exothea, Filicium, Ganophyllum, Glenniea, Gloeocarpus, Gongrodiscus, Gongrospermum, Guindilia, Guioa, Handeliodendron, Haplocoelum, Harpullia, Hippobromus, Homea, Houssayanthus, Hypelate, Hypseloderma, Jagera, Koelreuteria, Laccodiscus, Lecaniodiscus, Lepiderema, Lepidopetalum, Lepisanthes, Litchi, Llagunoa, Lophostigma, Loxodiscus, Lychnodiscus, Macphersonia, Maesa, Magonia, Majidea, Matayba, Melicoccus, Mischocarpus, Molinaea, Negundo, Neotina, Nephelium, Otonephelium, Otophora, Pappea, Paranephelium, Paullinia, Pavieasia, Pentascyphus, Phyllotrichum, Pittosporum, Placodiscus, Plagioscyphus, Podonephelium, Pometia, Porocystis, Pseudima, Pseudopancovia, Pseudopteris, Ptelea, Radlkofera, Rhysotoechia, Sapindus, Sarcopteryx, Sarcotoechia, Scyphonychium, Serjania, Sisyrolepis, Smelophyllum, Stadmania, Stocksia, Storthocalyx, Synima, Talisia, Thinouia, Thouinia, Thouinidium, Tina, Tinopsis, Toechima, Toulicia, Trigonachras, Tripterodendron, Tristira, Tristiropsis, Tsingya, Ungnadia, Urvillea, Vouarana, Xanthoceras, Xeropspermum, Zanha, Zollingeria.*

Saponins including triterpenoidal saponins may also be purified or isolated from the following species of plants:

*Acer campestre* L., *Acer chienii* Hu et Cheng, *Acer chingii* Hu, *Acer davidii* Franch, *Acer laxiflorum* Pax, *Acer mandshuricum* Maxim., *Acer mono* Maxim., *Acer orientale* L., *Acer palmatum* Thunb., *Acer sinense* Pax, *Acer wilsonii* Redhd., *Acer yui* Fang, *Aesculus arguta, Aesculus assamica* Griff., *Aesculus californica* (Spach) Nutt., *Aesculus chinensis* Bunge, *Aesculus chinensis* var. *Chekiangensis* (Hu et Fang) Fang, *Aesculus chuniana* Hu et Fang, *Aesculus flava* (*A. octandra*), *Aesculus glabra* Willd., *Aesculus hippocastanum, Aesculus indica, Aesculus lantsangensis* Hu et Fang, *wangii Aesculus megaphylla* Hu et Fang, *chinensis Aesculus neglecta, Aesculus octandra* Marsh., *Aesculus parviflora, Aesculus pavia, Aesculus polyneura* Hu et Fang, *Aesculus tsianguii* Hu et Fang, *Aesculus sylvatica, Aesculus turbinata, Aesculus wangii* Hu, *Aesculus wangii* var. *ruticola* Hu et Fang, *Aesculus wilsonii, Allophylus caudatus* Radlk. [*A. racemosus* auct. Non(L.) Radlk], *Allophylus chartaceus* (Kurz.)Radlk., *Allophylus cobbe* (Linn.) Raeuch. var. *velutinus* Corner, *Allophylus dimorphus* Radlk., *Allophylus hirsutus* Radlk., *Allophylus longipes* Radlk., *Allophylus petelotii* Merr., *Allophylus repandifolius* Merr. et Chun, *Allophylus timomsis* (DC.) Bl., *Allophylus tricophyllus* Merr. et Chun, *Allophylus viridis* Radlk., *Amesiodendron chinense* (Merr.) Hu, *Amesiodendron integrifoliolatum* H. S. Lo, *Amesiodendron tienlinense* H. S. Lo, *Aphania oligophylla* (Merr. et Chun) H. S. Lo, *Aphania rubra* (Roxb.) Radlk., *Arytera littoralis* Bl., *Blighia sapida, Boniodendron minus* (Hemsl.) T. Chen, *Barringtonia, Camellia axillaris* Roxb. ex Ker, *Camellia cordifolia* (Mech.) Hakai, *Camellia édithae* Hance, *Camellia irrawadiensis* Barua, *Camellia pitardii* Coh. Stuart, *Camellia reticulate* Lindl., *Camellia rosthomiana* Hand.-Mazz., *Camellia sinensis* O. Ktze., *Camellia tenii* Sealy, *Camellia tsaii* Hu, *Camellia wardii* Kobuski, *Camellia yunnanensis* Coh. Stuart, *Cardiospermum halicacabum* L., *Cupaniopsis anacardioides, Delavaya toxocarpa* Franch., *Dimocarpus confinis* (How et Ho) H. S. Lo, *Dimocarpus fumatus* (Bl.) Leenh. subsp. *cacicola* C. Y. Wu, *Dimocarpus longan* Lour.(*Euphoria longan* Lour.) Steud., *Dimocarpus yunanensis* (W. T. Wang) C. Y. Wu et T. Y. Ming, *Dipteronia dyerana* Henry, *Dipteronia sinensis* Oliv., *Dipteronia sinensis* Oliv. var. *taipeiensis* Fang et Fang f., *Dodonaea microzyga, Dodonaea viscosa* (L) Jacq.[*Ptelea viscosa* L.], *Erioglossum rubiginosum* (Roxb.) Bl., *Erythrophysa alata, Eurycorymbus austrosinensis* Hand.-Mazz., *Eurycorymbus cavaleriei* (Lével.) Rehd. et Hand.-Mazz., *Handeliodendron bodnieri* (Lévl.) Rehd., *Harpullia alata* F. Mueller, *Harpullia arborea* (Blanco) Rdlk., *Harpullia austro-calcdonica* Baillon, *Harpullia camptoneura* Radlk., *Harpullia cauliflora* K. Schum. & Lauterb., *Harpullia crustacea* Radlk., *Harpullia cupanoides* Roxb., *Harpullia frutescens* F. M. Bailey, *Harpullia giganteacapsula* M. Vente, *Harpullia hillii* F. Muell., *Harpullia hirsuta* Radlk., *Harpullia largifolia* Radlk., *Harpullia leptococca* Radlk., *Harpullia myrmecophila* Merr. & Perry, *Harpullia longipetala* Leench, *Harpullia peekeliana* Melch., *Harpullia pendula* Planch. ex F. muell., *Harpullia petiolaris* Radlk., *Harpullia ramiflora* Radlk., *Harpullia rhachiptera* Rdlk., *Harpullia rhyticarpa* C. T. White & Francis, *Harpullia solomenensis* M. Vente, *Harpullia vaga* Merr. & Perry, *Hypelate trifoliate, Koelreuteria apiculata* Rehd. et Wils., *Koelreuteria bipinnata* Franch., *Koelreuteria bipinnata* var. *integrifoliola* (Merr.) T. chen (*K. integrifoliola* Merr.), *Koelreutena elegans* (Seem.) A. C. Smith susp. *formosana* (Hayata) Meye, *Koelreutena monor* Hemsl., *Koelreuteria paniculata* Laxm., *Lepisanthes basicardia* Radlk., *Lepisanthes browniana* Hiern, *Lepisanthes hainanensis* H. S. Lo, *Litchi chinensis* Sonn., *Maesa hupehensis* Rehl., *Maesa japonica* (Thunb.) Moritzi, *Maesa lanceolata, Maesa laxiflora, Maesa montana* A. DC., *Maesa perlarius* (Lour.) Merr. *Maesa tenera* Mez, *Melicoccus bijuatus, Mischocarpus hainanensis* H. S. Lo, *Mischocarpus pentapetalus* (Roxb.) Radlk., *Mischocarpus sundaicus* Bl., *Nephelium Chryseum* Bl., *Nephelium lappaceum, Nephelium topengii* (Merr.) H. S. Lo, *Otophora unilocularis* (Leenh.) H. S. Lo, *Paranephelium hainanensis* H. S. Lo, *Paranephelium hystrix* W. W. Smith, *Pavieasia kwangsiensis* H. S. Lo, *Pavieasia yunnanensis* H. S. Lo, *Pittosporum balancae* DC., *Pittosporum brevicalyx* (Oliv.) Gagnep., *Pittosporum crassifolium* A. Cunn., *Pittosporum crispulum* Gagnep., *Pittosporum daphyniphylloides* Hayata, *Pittosporum elevaticostatum* H. T. Chang et Yan, *Pittosporum eugennioides* A. Cunn., *Pittosporum glabratum* Lindl., *Pittosporum glabratum* Lindl. var. *neriifolium* Rehd., *Pittosporum heterophyllum* Franch., *Pittosporum illicioides* Makino, *Pittosporum kerrii* Craib, *Pittosporum kunmingense* H. T. Chang et Yan, *Pittosporum leptosepalum* Gowda, *Pittosporum napaulense* (DC.) Rehd. et Wils., *Pittosporum omeiense* H. T. Chang et Yan, *Pittosporum ovoideum* Gowda, *Pittosporum parvicapsulare* H. T. Chang et Yan, *Pittosporum pauciflorum* Hook. et Arn., *Pittosporum pentandrum* var. *hainanense* (Gangnep.) H. L. Li, *Pittosporum perryanum* Gowda, *Pittosporum phillyraeoides* DC., *Pittosporum planilobum* H. T. Chang et Yan, *Pittosporum podocarpum* Gagnep., *Pittosporum podocarpum* Gagnep., *Pittosporum pulchrum* Gagnep., *Pittosporum rehderianum* Gowda, *Pittosporum rhombifolium* A. Cunn. ex Hook., *Pittosporum sahnianum* Gowda, *Pittosporum subulisepalum* Hu et Wang, *Pittosporum tenuifolium* Gaertn., *Pittosporum tobira* (Thunb.) Ait., *Pittosporum tobira* (Thunb.) Ait., var. *calvescens* Ohwi, *Pittosporum tonkenese*

Gagnep., *Pittosporum trigonocarpum* Lévl., *Pittosporum truncatum* Pritz., *Pittosporum undulatifolium* H. T. Chan et Yan, *Pittosporum undulatum* Venten., *Pittosporum viridiflorum, Pittosporum xylocarpum* Hu et Wang, *Pometia pinnata* J. R. et G. Forst., *Ptelea trifoliate, Ptelea viscosa* Linn., *Sapindus abruptus* Lour., *Sapindus Chinesis* Murray, *Sapindus delavayi* (Franch.) Radlk. [*Pancovia delavayi* Franch], *Sapindus mukorossi* Gaertn., *Sapindus rarak* DC., *Sapindus rarak* DC., var. *velutinus* C. Y. Wu, *Sapindus saponaria* var. *drummondii, Sapindus tomentosus* Kurz, *Ungnadia speciosa, Xanthoceras sorbifolia* Bunge. *Xeropspermum bonii* (Lecomte) Radlk.

This invention provides a compound comprising the structures recited in FIGS. 1 to 27. This invention provides a compound comprising a triterpenoidal saponin, triterpenoid, triterpenoidal compound or sapongenin, comprising two angeloyl group or at least two side groups selected from the group consisting of: angeloyl groups, tigloyl groups and senecioyl groups, wherein the side groups are attached to carbon 21 and 22 of triterpenoidal saponin, triterpenoid, triterpenoidal compound or sapongenin backbone. In an embodiment, the saponin comprising a sugar moiety, wherein the sugar moiety comprises at least one sugar, or D-glucose, or D-galactose, or L-rhamnose, or L-arabinose, or D-xylose, or alduronic acid, or D-glucuronic acid or D-galacturonic acid, or their derivative thereof, or the combination thereof. A sugar moiety is a segment of molecule comprising one or more sugar group. The above compounds are obtainable from the above-described plants. The compounds comprising the structure in FIGS. 1 to 27 are obtainable from the above-described plants.

This invention further provides composition comprising the structures recited in FIGS. 1 to 27, or a compound comprising a triterpenoidal saponin, triterpenoid, triterpenoidal compound or sapongenin, comprising at least two side groups selected from the group consisting of: angeloyl groups, tigloyl groups and senecioyl groups, wherein the side groups are attached to carbon 21, 22 or 28 of triterpenoidal saponin, triterpenoid, triterpenoidal compound or sapongenin backbone. These compositions are obtainable from the above-identified plants.

This invention further provides composition comprising the structures recited in FIGS. 1 to 27, or a compound comprising two angeloyl groups or at least two side groups selected from the group consisting of: angeloyl groups, tigloyl groups and senecioyl groups, This invention provides uses of the saponins isolated from the roots, kernel, leave, bark, stem, husk, seed, seed shell or fruit of the above plants, and methods of their preparations.

This invention provides a method of preparing the saponins, comprising the steps of:

(a) extracting roots, kernel, leave, bark, stem, husk, seed, seed shell or fruit or combinations thereof of the above plant with organic solvents such as ethanol or methanol to obtain a organic extract;

(b) collecting the organic extract;

(c) refluxing the organic extract to obtain a second extract;

(d) removing the organic solvent from the second extract to obtain a third extract;

(e) drying and sterilizing the third extract to obtain a crude extract powder;

(f) fractionating the crude extract powder into fractions or components. Fractionation may be achieved by HPLC and FPLC chromatography with silica gel, C18 or other equivalent solid phase materials;

(g) monitoring the fractions. If using HPLC or FPLC, absorption wavelength at 207 nm to 500 nm may be used;

(h) identifying the bioactive components of the crude extract;

(i) purifying one or more bioactive components of the crude extract with chromatographic techniques that employ FPLC to obtain one or more fraction of the bioactive component; and (j) isolating the bioactive components with chromatographic techniques that employ preparative columns and HPLC.

The following is an example of methods and materials that were used to test the bioactivities of Saponins or compounds of this invention.

Cells. Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain), SK-MEL-5 (Skin) and OVCAR-3 (ovary). Cells were grown in culture medium (HeLa-S3, DU145, MCF-7, Hep-G2 and T98G in MEN (Earle's salts); HTB-9, H460, K562, OVCAR-3 in RPMI-1640; HCT-116, U2OS in McCoy-5A) supplemented with 10% fetal calf serum, glutamine and antibiotics in a 5% $CO_2$ humidified incubator at 37° C.

MTT Assay. The procedure for MTT assay followed the method described in (Carmichael et al., 1987) with modifications. Cells were seeded into a 96-wells plate at concentrations of 10,000/well (HTB-9, HeLa, H460, HCT116, T98G, OVCAR-3), 15,000/well (DU145, MCF-7, HepG2, U2OS), or 40,000/well (K562), for 24 hours before drug-treatment. Cells were then exposed to drugs for 48 hours (72 hours for HepG2, U2OS, and 96 hours for MCF-7). After the drug-treatment, MTT (0.5 mg/ml) was added to cultures for an hour. The formation of formazan (product of the reduction of tetrazolium by viable cells) was dissolved with DMSO and the O.D. at 490 nm was measured by an ELISA reader. The MTT level of cells before drug-treatment was also measured (T0). The % cell-growth (% G) is calculated as:

$$\% \ G = (TD - T0 / TC - T0) \times 100 \tag{1},$$

where TC or TD represent O.D. readings of control or drug-treated cells. When T0>TD, then the cytotoxicity (LC) expressed as % of the control is calculated as:

$$\% \ LC = (TD - T0 / T0) \times 100 \tag{2}$$

This invention provides a composition effective in reducing or inhibiting cancer growth. The cancer includes but is not limited to bladder cancer, bone cancer and ovary cancer.

This invention provides a composition comprising triterpenoidal saponins or their derivatives for inhibiting tumor growth.

This invention provides a compound selected from a compound of formula (1):

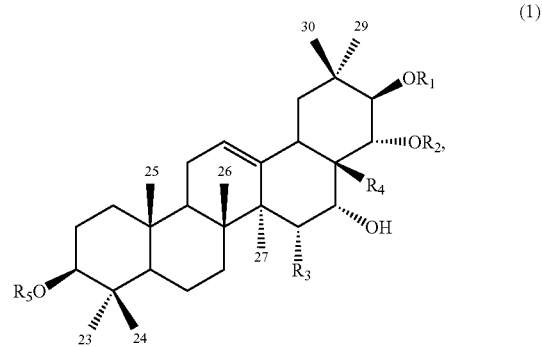

or a salt, ester, metabolite or derivative thereof, wherein R1 and R2 represent angeloyl group; R3 represents H or OH; R4 represent CH2OR6; and wherein R6 is H; R5 represents at least one sugar moiety or its derivatives.

In an embodiment, R1 and R2 represent angeloyl group; R3 represents H or OH; R4 represents COOR6 wherein R6 is H.

In an embodiment, R1 represents H; R2 represents angeloyl group; R3 represents H or OH; R4 represents CH2OR6 or COOR6; wherein R6 is an angeloyl group.

In another embodiment, R4 represents CH2OR6 or COO R6; at least two of R1, R2, and R6 comprise an angeloyl group or acid having five carbons; R3 represents H or OH; and wherein R6 is angeloyl group, H, acetyl group, tigloyl group, senecioly group, or an acid having two to five carbons.

In a further embodiment, at least one angeloyl of R1 or R2 is replaced by acetyl group, tigloyl group, senecioly group, or an acid having two to five carbons; R3 represents H or OH; R4 represents CH2OR6 or COOR6; and wherein R6 is angeloyl group.

In a further embodiment, the R4 represents CH2OR6 or COOR6; and wherein R6 is H or acetyl.

In a further embodiment, at least one of R1, R2, and R4 comprises a sugar moiety or is a compound comprises sugar moiety, wherein the sugar moiety comprises at least two angeloyl groups, acetyl group, tigloyl group, senecioly group, or an acid having two to five carbons or combination thereof. In a further embodiment, positions 23, 24, 25, 26, 29, 30 of the compound independently comprise CH3, CH2OH, CHO, COOH, alkyls group, acetyl group or derivative thereof.

In a further embodiment, R5 represents sugar moiety comprising glucose, galactose or/and arabinose.

In a further embodiment, R5 represents sugar moiety, wherein the sugar moiety comprises two sugars selected from D-glucose, D-galactose, L-rhamnose, L-arabinose, D-xylose, alduronic acid, D-glucuronic acid, D-galacturonic acid, and derivative thereof, and the combination thereof.

In a further embodiment, R5 represents sugar moiety, wherein the sugar moiety comprises three sugars selected from D-glucose, D-galactose, L-rhamnose, L-arabinose, D-xylose, alduronic acid, D-glucuronic acid, D-galacturonic acid, and derivative thereof, and the combination thereof.

In a further embodiment, R5 represents sugar moiety, wherein the sugar moiety comprises three sugars selected from D-glucose, D-galactose, L-rhamnose, L-arabinose, D-xylose, and derivative thereof, and the combination thereof.

In a further embodiment, R5 represents sugar moiety, wherein the sugar moiety comprises at least one sugar, or D-glucose, D-galactose, or L-rhamnose, or L-arabinose, or D-xylose, or alduronic acid, or D-glucuronic acid or D-galacturonic acid, or derivative thereof, or the combination thereof.

In an embodiment, R5 represents a compound capable of performing the function of the sugar moiety.

In a further embodiment, the R5 represents H. In a further embodiment, R4 represents H or OH or CH3. In a further embodiment, R1 or/and R2 is a functional group capable of performing the function of the angeloyl. R5 represents a compound capable of performing the function of the sugar moiety.

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound. In a further embodiment, the angeloyl groups are in a trans-position on a structure.

This invention provides a compound selected from a compound of formula (2):

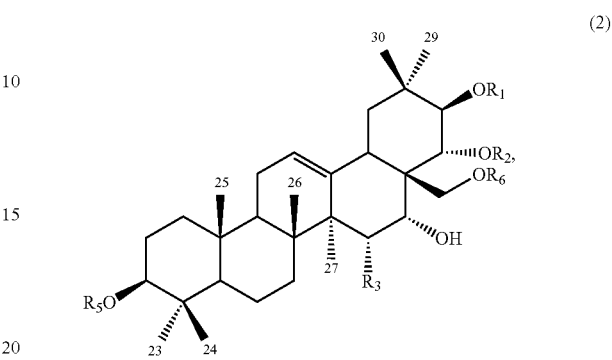

(2)

or a salt, ester or derivative thereof, wherein R1 represents angeloyl group; R2 represents angeloyl group; R3 represents OH or H; Positions 23, 24, 25, 26, 27, 29, 30 of the compound independently comprise CH3, or CH2OH, or CHO, or COOH, alkyls group, or acetyl group, or derivative; R6 represents Ac or H; and R5 represents sugar moiety, wherein the sugar moiety comprises at least one sugar, or D-glucose, or D-galactose, or L-rhamnose, or L-arabinose, or D-xylose, or alduronic acid, or D-glucuronic acid, or D-galacturonic acid, or their derivative thereof, or the combination thereof. In an embodiment, R5 represents a compound capable of performing the function of the sugar moiety. In another embodiment the sugar moiety comprises L-arabinose, D-glucose and/or D-galactose, or combinations thereof. In a further embodiment, any two of R1, R2 or R6 are angeloyl groups, or any one of R1, R2 or R6 is attached to a sugar moiety in which two angeloyl groups are attached to adjacent carbons of the monosaccharides. In a further embodiment, R1, R2, and R6 comprises angeloyl group, acetyl group, tigloyl group, senecioly group, or an acid with two to five carbons or combibation thereof. In a further embodiment, at least one of R1, R2 or R6 is attached a sugar moiety, wherein sugar moiety comprises two angeloyl group, acetyl group, tigloyl group, senecioly group, acid having two to five carbons, or combinations thereof.

This invention provides a compound selected from a compound of formula (3):

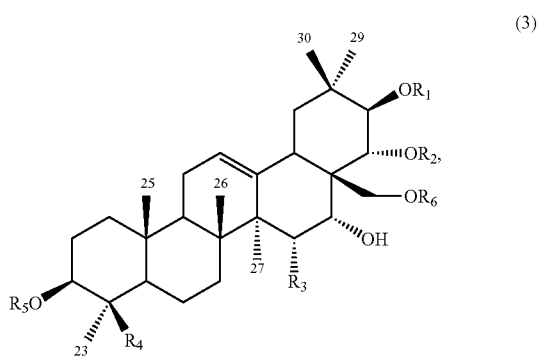

(3)

or a salt, ester or derivative thereof, wherein R1 represents angeloyl group; R2 represents angeloyl group; R3 represents OH or H; R4 represents CH3 or CH2OH or alkyls group or their derivatives; R6 represents Ac or H and R5 represents sugar moiety, wherein the sugar moiety comprises at least one sugar, or D-glucose, or D-galactose, or L-rhamnose, or L-arabinose, or D-xylose, or alduronic acid, or D-glucuronic acid, or D-galacturonic acid, or derivative thereof, or the combination thereof. In an embodiment, R5 represents a compound capable of performing the function of sugar moiety. In another embodiment the sugar moiety comprises L-arabinose, or D-glucose, or D-galactose, or combinations thereof. In a further embodiment, at least one of R1, R2 or R6 is attached a sugar moiety or rhamnose, wherein sugar moiety or rhamnose comprises two angeloyl group, acetyl group, tigloyl group, senecioly group, acid having two to five carbons, or combinations thereof.

This invention provides a compound selected from a compound of formula (4):

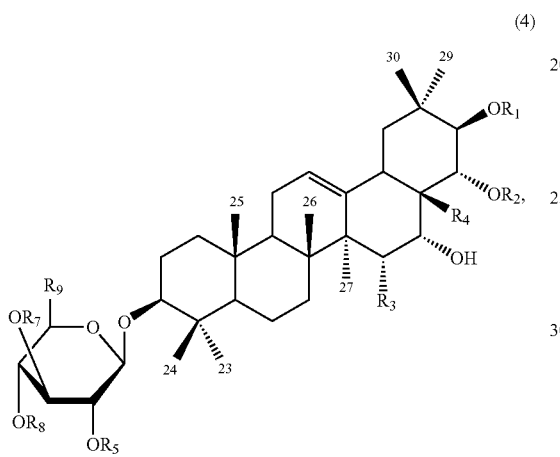

(4)

or a salt, ester, metabolite or derivative thereof, wherein R1 and R2 represent angeloyl group; R3 represents H or OH; R4 represent CH2OR6; and wherein R6 is H or acetyl; R5 represents sugar moiety or D-glucose; R7 represents a sugar moiety or L-arabinose; R8 represents sugar moiety or D-galactose; R9 represent COOH or CH2OH.

In an embodiment, R4 represents COOR6, wherein the R6 is H or acetyl. In an embodiment, the R5, R7 or/and R8 are H or sugar moiety, wherein the sugar moiety comprises at least one sugar, or glucose, or galactose, or rhamnose, or arabinose, or xylose, or alduronic acid, or glucuronic acid or galacturonic acid, or derivative thereof. In an embodiment, at least 2 of R1, R2 and R6 are angeloyl group; R4 represent CH2OR6 or COOR6, wherein R6, R1 and R2 are angeloyl group, acetyl group, tigloyl group, senecioly group, an acid having two to five carbons or H. In a further embodiment, at least two of R1, R2 and R6 are angeloyl group, acetyl group, tigloyl group, senecioly group, or an acid having two to five carbons; R3 represents H or OH; R4 represents CH2OR6 or COOR6, where R6 is H or angeloyl group, acetyl group, tigloyl group, senecioly group.

In an embodiment, R1 and R2 represent angeloyl group; R3 represents H or OH; R4 represents COOR6 wherein R6 is H;

In an embodiment, R1 represents H; R2 represents angeloyl group; R3 represents H or OH; R4 represents CH2OR6 or COOR6; wherein R6 is an angeloyl group.

In another embodiment, at least two of R1, R2, and R6 comprise an angeloyl group; R3 represents H or OH; R4 represents CH2OR6 or COOR6; and wherein R6 is H, angeloyl group, acetyl group, tigloyl group, senecioly group, or an acid having two to five carbons.

In a further embodiment, at least one angeloyl of R1 or R2 is replaced by acetyl group, tigloyl group, senecioly group, or an acid having two to five carbons; R3 represents H or OH; R4 represents CH2OR6 or COOR6; and wherein R6 is angeloyl group.

In a further embodiment, at least one of R1, R2, and R6 is a sugar moiety or rhamnose comprising at least two angeloyl groups, acetyl group, tigloyl group, senecioly group, or an acid having two to five carbons or combination thereof. In a further embodiment, positions 23, 24, 25, 26, 29, 30 of the compound independently comprise CH3, CH2OH, CHO, COOH, alkyls group, acetyl group or derivative thereof. In a further embodiment, R4 represents H or OH or CH3. A sugar moiety is a segment of molecule comprising one or more sugar group.

This invention provides a compound selected from a compound of formula (5):

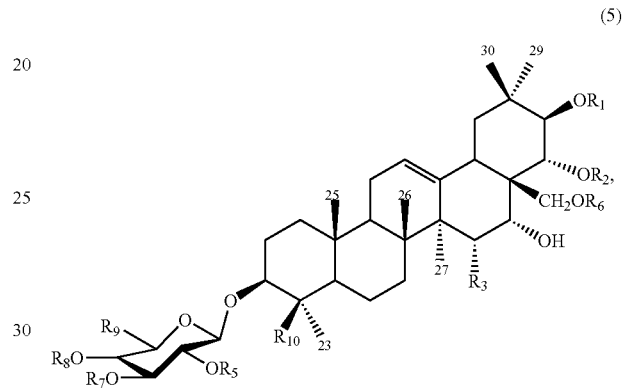

(5)

or a salt, ester, metabolite or derivative thereof, wherein R1 and R2 represent angeloyl group; R3 represents H or OH; R6 represent H or acetyl; R9 represents COOH or CH2OH; R10 represent CH3 or CH2OH or COOH; R5, R7 and R8 are H or/and sugar moiety, wherein the sugar moiety comprises at least one sugar, D-glucose, D-galactose, L-rhamnose, L-arabinose, D-xylose, alduronic acid, D-glucuronic acid, or D-galacturonic acid, or derivative thereof. In an embodiment, at least one of R1, R2, and R6 is a sugar moiety or compound comprising at least two angeloyl groups, acetyl group, tigloyl group, senecioly group, or an acid having two to five carbons or combination thereof. In another embodiment, at least two of R1, R2, and R6 comprise an angeloyl group This invention provides a compound selected from a compound of formula (6):

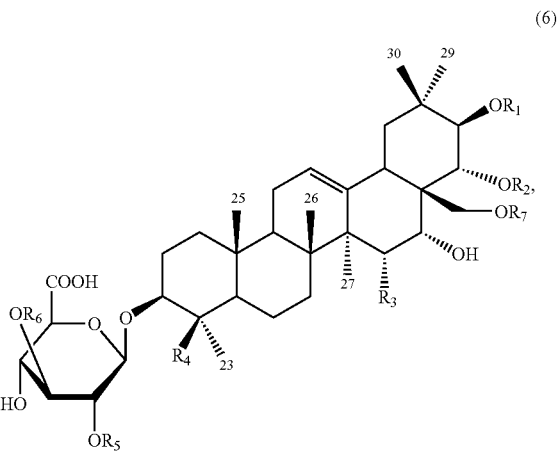

(6)

or a salt, ester or, derivative thereof, wherein R1 represents angeloyl group; R2 represents angeloyl group; R3 represents OH or H; R4 represents CH3 or CH2OH; R7 represents H; and R5 represents D-glucose, D-Galactose, L-arabinose or H; and R6 represents D-glucose, D-Galactose, L-arabinose or H. In anbodiment, R5 or/and R6 are H or sugar moiety comprises at least one sugar, D-glucose, D-galactose, L-rhamnose, L-arabinose, D-xylose, alduronic acid, D-glucuronic acid, or D-galacturonic acid, or derivative thereof.

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a compound selected from a compound of formula (1A):

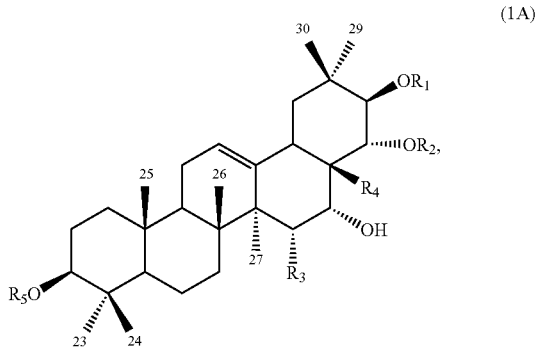

(1A)

or a salt, ester, metabolite or derivative thereof, wherein R1 and R2 independently represent angeloyl group; R3 represents H or OH; R4 represent CH2OR6; and wherein R6 is H; R5 represents at least one sugar moiety or its derivatives. In an embodiment, R1 and R2 independently represent angeloyl group; R3 represents H or OH; R4 represents COOR6 wherein R6 is H; R5 represents at least one sugar moiety or its derivatives.

In an embodiment, R1 represents H; R2 represents angeloyl group; R3 represents H or OH; R4 represents CH2OR6 or COOR6; wherein R6 is an angeloyl group; and R5 represents at least one sugar moiety or its derivatives.

In another embodiment, R3 represents-H or OH; R4 represents CH2OR6 or COOR6; and wherein R6 is angeloyl group, H, acetyl group, tigloyl group, senecioyl group, or an acid having two to five carbons; at least two of R1, R2, and R6 comprise an angeloyl group or acid having five carbons; R5 represents at least one sugar moiety or its derivatives.

In a further embodiment, at least one angeloyl from R1 or R2 is replaced by acetyl group, tigloyl group, senecioyl group, or an acid having two to five carbons; R3 represents H or OH; R4 represents CH2OR6 or COOR6 wherein R6 is angeloyl group; R5 represents at least one sugar moiety or its derivatives.

In a further embodiment, R4 represents CH2OR6 or COOR6; at least one of R1, R2, and R6 is a sugar moiety comprising at least two angeloyl groups, acetyl group, tigloyl group, senecioyl group, or an acid having two to five carbons or combination thereof.

In a further embodiment, position 24 of the compound comprises CH3 or CH2OH. In a further embodiment, positions 23, 24, 25, 26, 29, 30 of the compound independently comprise CH3 or CH2OH.

In a further embodiment, positions 23, 24, 25, 26, 29, 30 of the compound independently comprise CH3, CH2OH, CHO, COOH, COOalkyl, COOaryl, COO-heterocyclic, COO-heteroaryl, $CH_2O$aryl, $CH_2O$— heterocyclic, $CH_2O$— heteroaryl, alkyls group, acetyl group or derivative thereof.

In a further embodiment, R5 represents sugar moiety comprising glucose, galactose and arabinose.

In a further embodiment, R5 represents sugar moiety, wherein the sugar moiety comprises at least one sugar, or D-glucose, D-galactose, or L-rhamnose, or L-arabinose, or D-xylose, or alduronic acid, or D-glucuronic acid or D-galacturonic acid, or derivative thereof, or the combination thereof.

In a further embodiment, R5 represents sugar moiety, wherein the sugar moiety comprises two sugars comprising D-glucose, or D-galactose, or L-rhamnose, or L-arabinose, or D-xylose, or alduronic acid, or D-glucuronic acid or D-galacturonic acid, or derivative thereof, or the combination thereof.

In a further embodiment, R5 represents sugar moiety, wherein the sugar moiety comprises at least three sugars selected from D-glucose, or D-galactose, or L-rhamnose, or L-arabinose, or D-xylose, or alduronic acid, or D-glucuronic acid or D-galacturonic acid, or derivative thereof, or the combination thereof.

In a further embodiment, R5 represents sugar moiety, wherein the sugar moiety comprises at least one sugar, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof.

In a further embodiment, R5 represents sugar moiety, wherein the sugar moiety comprises three sugars selected from glucose, galactose, rhamnose, arabinose, xylose, fucose, allose, altrose, gulose, idose, lyxose, mannose, psicose, ribose, sorbose, tagatose, talose, fructose, alduronic acid, glucuronic acid and galacturonic acid, and derivative thereof, and the combination thereof.

In a further embodiment, R5 represents sugar moiety, wherein the sugar moiety comprises three sugars selected from glucose, galactose, rhamnose, arabinose, xylose, fucose, and derivative thereof, and the combination thereof.

In an embodiment, R5 represents a compound capable of performing the function of the sugar moiety. In a further embodiment, the R5 represents H. In a further embodiment, R4 represents H or OH or CH3.

In a further embodiment, R1 or/and R2 is a functional group capable of performing the function of the angeloyl. R5 represents a compound capable of performing the function of the sugar moiety.

In a further embodiment, R1 and R2 are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl.

In a further embodiment, R1 and R2 comprise angeloyl, tigloyl, senecioyl, benzoyl or alkenoyl.

In a further embodiment, R4 represents CH2OR6; at least two of R1, R2 and R6 are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl. In a further embodiment, R4 represents CH2OR6; at least two of R1, R2 and R6 are comprise angeloyl, tigloyl, senecioyl, benzoyl or alkenoyl.

In a further embodiment, R4 represents CH2OR6; at least two of R1, R2 and R6 are comprise angeloyl, benzoyl or alkenoyl.

In a further embodiment, R1 and R2 are selected from H, angeloyl, acetyl, tigloyl, senecioyl, alkyl, acyl, benzoyl, dibenzoyl, alkanoyl, alkenoyl, benzoyl alkyl substituted alkanoyl, aryl, heterocylic or heteroraryl; R4 represents CH2OR6 or COOR6; wherein R6 is selected from H, COCH3, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; at least two of R1, R2 and R6 are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, at least two of R1, R2 and R4 are comprising angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, at least two of R1, R2 and R4 comprise angeloyl, acetyl, tigloyl, senecioyl, benzoyl, alkenoyl, or derivative thereof.

In a further embodiment, at least two of R1, R2 and R4 comprise angeloyl, tigloyl, senecioyl, benzoyl, alkenoyl, or derivative thereof.

In a further embodiment, at least two of R1, R2 and R4 comprise a compound capable of performing the function of angeloyl.

In a further embodiment, at least two of R1, R2 and R4 comprise a compound capable of performing the function of benzoyl.

In a further embodiment, R4 represents CH2OR6, COOR6 or CH2COOR6; at least two of R1, R2 and R6 are comprise angeloyl, tigloyl, senecioyl, benzoyl, alkenoyl, benzoyl or derivative thereof.

In a further embodiment, R4 represents CH2OR6, COOR6 or CH2COOR6; R1, R2 and/or R6 is/are sugar moiety, which comprise compounds selected from H, angeloyl, acetyl, tigloyl, senecioly, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; R1, R2 and/or R6 is/are sugar moiety, which comprise at least 2 compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; R1, R2 and/or R6 is/are sugar moiety, which comprise at least 2 compounds selected from angeloyl, tigloyl, senecioyl, benzoyl, alkenoyl or derivative thereof.

In a further embodiment, R4 represents CH2OR6, COOR6 or CH2COOR6; R1, R2 and/or R6 is/are sugar moiety, which comprise at least 2 compounds selected from angeloyl, benzoyl, alkenoyl or derivative thereof.

In a further embodiment, a compound selected from formula (1A) comprises at least 2 compounds selected from angeloyl, acetyl, tigloyl, senecioyl, or derivative thereof or a compound performing the function of angeloyl.

In a further embodiment, a compound selected from formula (1A) comprise at least 2 compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocyclic or heteroraryl or derivative thereof.

In a further embodiment, a compound selected from formula (1A) comprises a sugar moiety or a compound capable of performing function of sugar moiety and at least 2 compounds selected from angeloyl, acetyl, tigloyl, senecioyl, or derivative thereof or a compound capable performing the function of angeloyl.

In a further embodiment, a compound selected from formula (1A) comprise a sugar moiety or a compound capable of performing the function of sugar moiety and at least 2 compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, a compound selected from formula (1A) wherein R1 and R2 comprise compound selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, acyl, heterocylic or heteroraryl or derivative thereof. R4 is a compound comprising CH2OCCH3, CH2COOalkyl, CH2OH, COOH, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a compound selected from a compound of formula (1B):

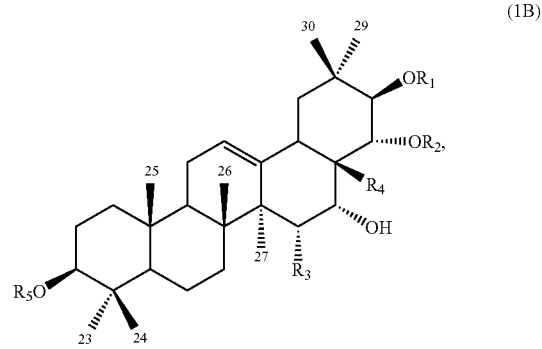

(1B)

or a salt, ester, metabolite or derivative thereof, wherein R1 comprise compound selected from hydrogen, angeloyl, acetyl, tigloyl, senecioyl, alkyl, dibenzoyl, benzoyl, alkanoyl, alkenoyl, benzoyl alkyl substituted alkanoyl, aryl, heterocylic or heteroraryl or derivative thereof; R2 comprise compound selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof; R4 represents CH2OR6, COOR6 wherein R6 is selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof; R3 is H or OH; R5 represents sugar moiety, wherein the sugar moiety comprises at least one sugar, D-glucose, D-galactose, L-rhamnose, L-arabinose, D-xylose, alduronic acid, D-glucuronic acid or D-galacturonic acid or derivative thereof, or the combination thereof.

In an embodiment, R1 represent a sugar moiety comprises at least two compound selected from, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R1 represent a sugar moiety comprises at least one compound selected from, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R2 represent a sugar moiety comprises at least one compound selected from, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R2 represent a sugar moiety or a compound comprises at least two compound selected from, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R4 represents CH2OR6, COOR6 wherein R6 is a sugar moiety which comprises at least one compound selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R4 represents CH2OR6, COOR6 wherein R6 is a sugar moiety which comprises at least two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R4 represents CH2OR6, COOR6 wherein R6 is a sugar moiety which comprises at least two compounds selected from angeloyl, acetyl, tigloyl, senecioyl, alkyl, In an embodiment, R4 represents CH2OR6, COOR6 wherein R6 is a sugar moiety which comprises at least two compounds selected from angeloyl, acetyl, tigloyl, senecioyl, alkyl, benzoyl, dibenzoyl, alkanoyl, alkenoyl, dibenzoyl, benzoyl alkyl substituted alkanoyl, aryl, acyl, heterocylic or heteroraryl or derivative thereof.

In an embodiment, R4 represents CH2OR6, COOR6 of formula (1B), at least two of R1, R2 and R6 comprise the compound selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R4 represents CH2OR6, COOR6 of formula (1B), at least two of R1, R2 and R6 comprise angeloyl, benzoyl, alkenoyl, or derivative thereof.

In an embodiment, R4 is a compound comprising CH2OCCH3, CH2COOalkyl, CH2OH, COOH, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, R5 represents sugar moiety, wherein the sugar moiety comprises at least one sugar, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof.

In a further embodiment, R5 represents sugar moiety, wherein the sugar moiety comprises two sugars selected from glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivative thereof, and the combination thereof.

In a further embodiment, R5 represents sugar moiety, wherein the sugar moiety comprises three sugars selected from glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivative thereof, and the combination thereof.

In a further embodiment, R5 represents sugar moiety, wherein the sugar moiety comprises at least four sugars selected from glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivative thereof, and the combination thereof.

In a further embodiment, R5 represents sugar moiety, wherein the sugar moiety comprises three sugars selected from glucose, galactose, rhamnose, arabinose, xylose, fucose, and derivative thereof, and the combination thereof.

In an embodiment, R5 represents sugar moiety or a compound capable of performing the function of the sugar moiety.

In a further embodiment, the R5 represents H.

In a further embodiment, R4 represents H or OH or CH3.

In a further embodiment, positions 23, 24, 25, 26, 29, 30 of the compound independently comprise CH3, CH2OH, CHO, COOH, COOalkyl, COOaryl, COO-heterocyclic, COO-heteroaryl, $CH_2Oaryl$, $CH_2O$— heterocyclic, $CH_2O$— heteroaryl, alkyls group, acetyl group or derivative thereof.

In a further embodiment, R5 represents sugar moiety selected from D-glucose, D-galactose, L-rhamnose and L-arabinose and their combination thereof.

In a further embodiment, R5 represents sugar moiety comprising D-glucose, D-galactose and L-arabinose or their combination thereof.

In a further embodiment, R5 represents sugar moiety comprising D-glucose, D-galactose, L-rhamnose, D-xylose or L-arabinose or their combination thereof or derivative thereof.

In a further embodiment, R5 represents sugar moiety, wherein the sugar moiety comprises at least two sugar selected from D-glucose, D-galactose, L-rhamnose, L-arabinose, D-xylose, alduronic acid, D-glucuronic acid, D-galacturonic acid and derivative thereof, and the combination thereof.

In a further embodiment, R5 represents sugar moiety, wherein the sugar moiety comprises three sugars selected from D-glucose, D-galactose, L-rhamnose, L-arabinose, D-xylose, alduronic acid, D-glucuronic acid, D-galacturonic acid and derivative thereof, and the combination thereof.

In a further embodiment, R5 represents sugar moiety, wherein the sugar moiety comprises at least three sugars selected from D-glucose, D-galactose, L-rhamnose, L-arabinose, D-xylose, alduronic acid, D-glucuronic acid, D-galacturonic acid and derivative thereof, and the combination thereof.

In a further embodiment, R1 and R2 independently comprise an angeloyl group.

In a further embodiment, R1 is a sugar moiety or a compound which comprise two angeloyl groups.

In a further embodiment, R1 and R2 independently comprise a benzoyl group.

In a further embodiment, R1 is a sugar moiety which comprises two benzoly groups.

In a further embodiment, R3 represents H or OH.

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a compound selected from a compound of formula (1C):

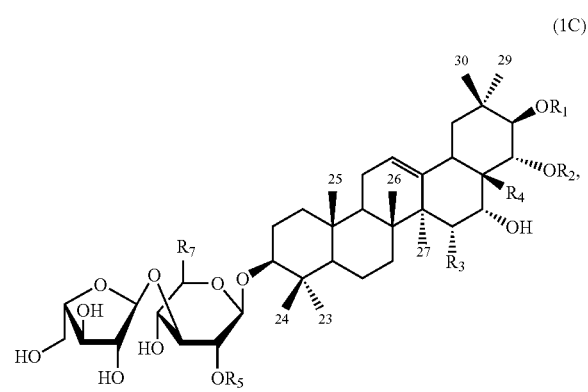

(1C)

or a salt, ester, metabolite or derivative thereof, wherein R1 and R2 independently represent angeloyl group; R3 represents H or OH; R4 represent CH2OR6 wherein R6 is H; R5 represents sugar moiety or D-glucose, D-galactose or its derivatives. R7 represent COOH In an embodiment, R1 and R2 independently represent angeloyl group; R3 represents H or OH; R4 represents COOR6 wherein R6 is H; R5 represents sugar moiety or D-glucose, D-galactose or its derivatives. R7 represent COOH.

In an embodiment, R1 represents H; R2 represents angeloyl group; R3 represents H or OH; R4 represents CH2OR6 or COOR6; wherein R6 is an angeloyl group or acetyl group.

In another embodiment, at least two of R1, R2, and R6 comprise an angeloyl group or acid having five carbons; R3 represents H or OH; R4 represents CH2OR6 or COOR6; and wherein R6 is angeloyl group, H, acetyl group, tigloyl group, senecioyl group, or an acid having two to five carbons.

In a further embodiment, at least one angeloyl from R1 or R2 is replaced by acetyl group, tigloyl group, senecioyl group, or an acid having two to five carbons; R3 represents H or OH; R4 represents CH2OR6 or COOR6 wherein R6 is angeloyl group.

In a further embodiment, R4 represents CH2OR6 or COOR6; at least one of R1, R2, and R6 is a sugar moiety comprising at least two angeloyl groups, acetyl group, tigloyl group, senecioyl group, or an acid having two to five carbons or combination thereof.

In a further embodiment, positions 24 of the compound comprise CH3 or CH2OH.

In a further embodiment, R7 represent COOH, CH2OH or CH3.

In a further embodiment, R7 represent CH3, CH2OH, CHO, COOH, COOalkyl.

In a further embodiment, R7 represent CH3, CH2OH, CHO; COOH, COOalkyl, COOaryl, COO-heterocyclic, COO-heteroaryl, CH2Oaryl, CH2O— heterocyclic, CH2O-heteroaryl, alkyls group, acetyl group or derivative thereof.

In a further embodiment, positions 24 of the compound comprise CH3 or CH2OH.

In a further embodiment, positions 23, 24, 25, 26, 29, 30 of the compound independently comprise CH3, CH2OH.

In a further embodiment, positions 23, 24, 25, 26, 29, 30 of the compound independently comprise CH3, CH2OH, CHO, COOH, COOalkyl, COOaryl, COO-heterocyclic, COO-heteroaryl, CH2Oaryl, CH2O-heterocyclic, CH2O-heteroaryl, alkyls group, acetyl group or derivative thereof.

In a further embodiment, R5 represents sugar moiety comprising glucose or galactose.

In a further embodiment, R5 represents sugar moiety, or D-glucose, D-galactose, or L-rhamnose, or L-arabinose, or D-xylose, or alduronic acid, or D-glucuronic acid or D-galacturonic acid, or derivative thereof, or the combination thereof.

In a further embodiment, R5 represents sugar moiety, glucose, galactose, rhamnose, arabinose, xylose, fucose or derivative thereof.

In a further embodiment, R5 represents sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof.

In an embodiment, the R5 represents H.

In a further embodiment, R4 represents CH2OR6 wherein R6 represent H or acetyl group.

In a further embodiment, R4 represents H or OH or CH3.

In a further embodiment, R1 or/and R2 is a functional group capable of performing the function of the angeloyl. R5 represents a compound capable of performing the function of the sugar moiety.

In a further embodiment, R1 and R2 are selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R1 or/and R2 is a sugar moiety comprise two of compounds selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R1 and R2 are selected from H, angeloyl, acetyl, tigloyl, senecioyl, alkyl, benzoyl, alkanoyl, alkenoyl, benzoyl alkyl substituted alkanoyl, aryl, acyl, heterocylic or heteroraryl; R4 represents CH2OR6 or COOR6; wherein R6 is selected from H, COCH3, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; at least two of R1, R2 and R6 are selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; R1, R2 and/or R6 is/are sugar moiety, which comprise compounds selected from H, angeloyl, acetyl, tigloyl, senecioly, alkyl, benzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; R1, R2 and/or R6 is/are sugar moiety, which comprise at least 2 compounds selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, a compound selected from formula (1C) comprises at least 2 compounds selected from angeloyl, acetyl, tigloyl, senecioyl, or derivative thereof or a compound capable performing the function of angeloyl.

In a further embodiment, a compound selected from formula (1C) comprise at least 2 compounds selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, a compound selected from formula (1C) wherein R1 and R2 comprise compound selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof. R4 is a compound comprising CH2OCCH3, CH2COOalkyl, CH2OH, COOH, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a compound selected from a compound of formula (1D):

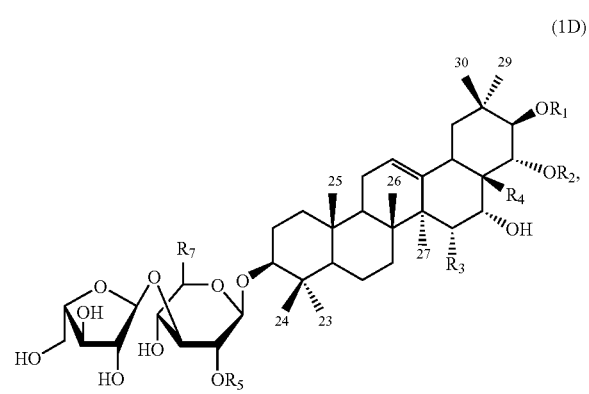

(1D)

or a salt, ester, metabolite or derivative thereof, wherein R1 comprise compound selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof; R2 comprise compound selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof; R4 represents CH2OR6, COOR6 wherein R6 is selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof; R3 is H or OH; R5 represents sugar moiety, or D-glucose or D-galactose; R7 represent COOH In ambodiment, R7 represent CH3, CH2OH, COOH, COOalkyl, In ambodiment, R7 represent CH3, CH2OH, CHO, COOH, COOalkyl, COOaryl, COO-heterocyclic, COO-heteroaryl, $CH_2Oaryl$, $CH_2O$-heterocyclic, $CH_2O$-heteroaryl, alkyls group, acetyl group or derivative thereof.

In an embodiment, R1 represent a compound comprising a sugar moiety comprises at least two compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R1 represent a compound comprising a sugar moiety comprises at least one compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R2 represent a compound comprising a sugar moiety comprises at least one compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R2 represent a compound comprising a sugar moiety or a compound which comprises at least two compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof; In an embodiment, R4 represents CH2OR6, COOR6 wherein R6 is a sugar moiety which comprises at least one compound selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R4 represents CH2OR6, COOR6 wherein R6 is a sugar moiety which comprises at least two compounds selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R4 represents CH2OR6, COOR6 wherein R6 is a sugar moiety which comprises at least two compounds selected from angeloyl, acetyl, tigloyl, senecioyl, alkyl, In an embodiment, R4 represents CH2OR6, COOR6 wherein R6 is a sugar moiety which comprises at least two compounds selected from angeloyl, acetyl, tigloyl, senecioyl, alkyl, benzoyl, alkanoyl, alkenoyl, dibenzoyl, benzoyl alkyl substituted alkanoyl, aryl, acyl, heterocylic or heteroraryl or derivative thereof;

In an embodiment, R4 represents CH2OR6, COOR6 wherein at least two of R1, R2 and R6 comprise the compound selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R4 is a compound comprising CH2OCCH3, CH2COOalkyl, CH2OH, COOH, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R5 represents sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof. In an embodiment, R5 represents a compound capable of performing the function of the sugar moiety. In a further embodiment, the R5 represents H. In a further embodiment, R4 represents H or OH or CH3.

In an embodiment, position 24 of the compound comprise CH3 or CH2OH,

In a further embodiment, positions 23, 24, 25, 26, 29, 30 of the compound independently comprise CH3, CH2OH, CHO, COOH, COOalkyl, COOaryl, COO-heterocyclic, COO-heteroaryl, CH$_2$Oaryl, CH$_2$O-heterocyclic, CH$_2$O-heteroaryl, alkyls group, acetyl group or derivative thereof.

In a further embodiment, R5 represents sugar moiety comprising L-glucose, D-galactose, L-rhamnose, or/and L-arabinose.

In a further embodiment, R1 and R2 independently represent angeloyl group; In a further embodiment, R1 is a sugar moiety or rhamnose which comprise two angeloyl groups.

In a further embodiment, R3 represents H or OH;

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a method of inhibiting tumor cell growth comprising administering to a subject, in need thereof, an appropriate amount of triterpenoidal saponins comprising two or more angeloyl groups or comprising the structure of FIGS. 1-27.

This invention provides a composition comprising the compounds as described above effective in reducing or inhibiting cancer growth. The cancer includes but is not limited to bladder cancer, bone cancer, skin cancer and ovarian cancer.

The saponins isolated from *Xanthoceras sorbifolia* with the characteristic structure described in the present invention can be used for anti-cancer therapy. The cancer includes but is not limited to bladder cancer, bone cancer, skin cancer and ovarian cancer.

Figure 1:
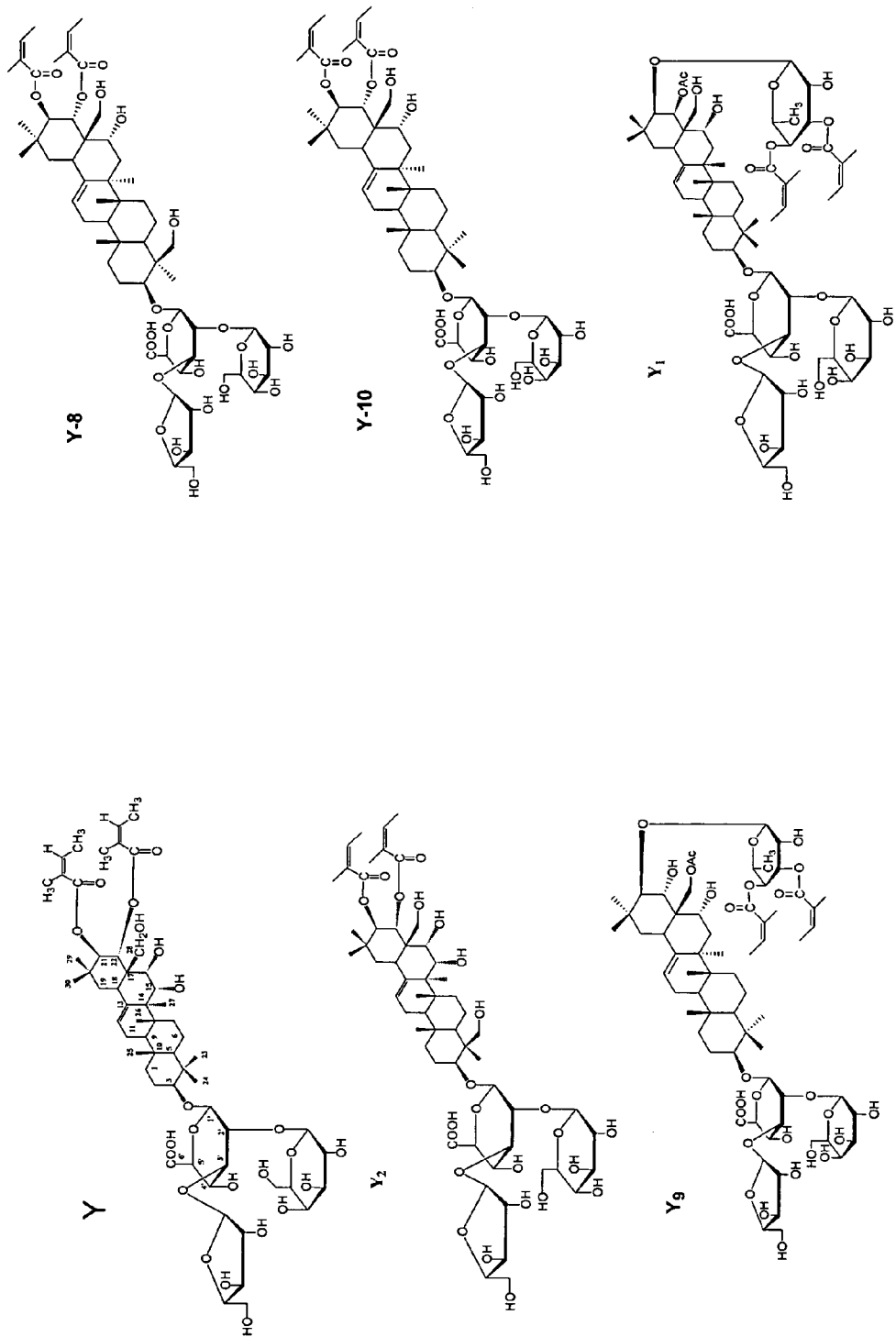
Figure 4:
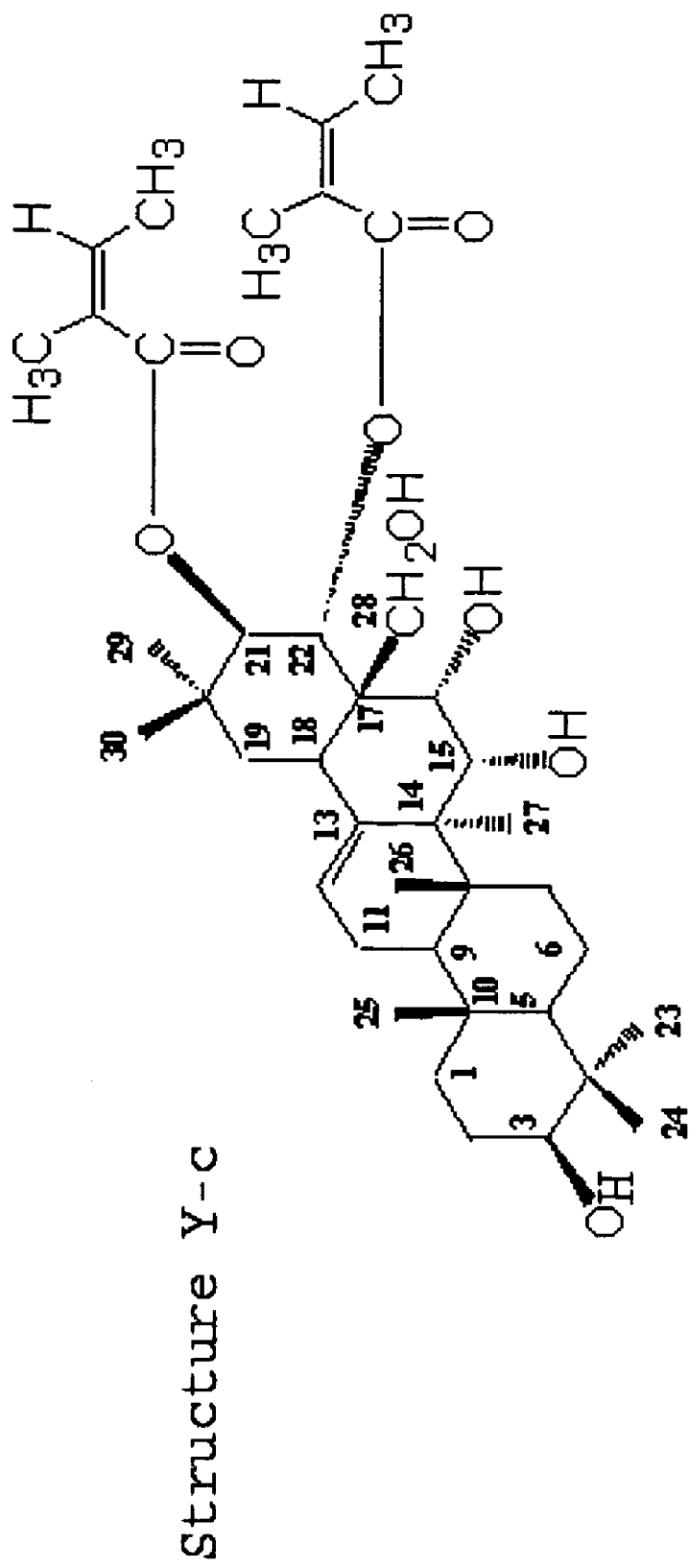
FIG. 4 shows structure of saponins

This invention provides a composition comprising the above described compounds or their derivatives for treating human immunodeficiency virus (HIV), Severe Acute Respiratory Syndrome (SARS), flu disease or inhibits virus activities. The biologically active triterpenoid saponins structures are shown in FIG. 1

Triterpenoid saponins comprises the formula as following:

3-O-{[β-D-galactopyranosyl (1→2)]-[α-L-arabinofuranosyl (1→3)]-β-D-glucuronopyranoside butyl ester}-21-O-acetyl-22-O-angeloyl-3β,16α,21β,22α,28-pentahydroxyolean-12-ene.

3-O-[β-D-galactopyranosyl(1→2)]-α-L-arabinofuranosyl (1→3)-β-D-glucuronopyranosyl-21,22-O-diangeloyl-3β, 15α,16α,21β, 22α,28-hexahydroxyolean-12-ene, 3-O-[β-D-galactopyranosyl(1→2)]-α-L-arabinofuranosyl (1→3)-β-D-glucuronopyranosyl-21-O-(3,4-diangeloyl)-α-L-rhamnophyranosyl-22-O-acetyl-3β,16α,21β, 22α, 28-pentahydroxyolean-12-ene, 3-O-[β-D-glucopyranosyl-(1→2)]-α-L-arabinofuranosyl (1→3)-β-D-glucuronopyranosyl-21,22-O-diangeloyl-3β, 15α,16α,21β,22α,24β,28-heptahydroxyolean-12-ene, 3-O-[β-glucopyranosyl (1→2)]-α-arabinofuranosyl (1→3)-β-glucuronopyranosyl-21,22-O-diangeloyl-3β,16α,21β, 22α,24β,28-hexahydroxyolean-12-ene, 3-O-[β-galactopyranosyl (1→2)]-α-arabinofuranosyl (1→3)-β-glucuronopyranosyl-21-O-(3,4-diangeloyl)-α-rhamnopyranosyl-28-O-acetyl-3β,16α,21β,22α,28-pentahydroxyolean-12-ene, 3-O-[β-galactopyranosyl (1→2)]-α-arabinofuranosyl (1→3)-β-glucuronopyranosyl-21,22-O-diangeloyl-3β, 16α,21β,22α,28-pentahydroxyolean-12'-ene, This invention provides a composition comprising the compounds as described above effective in reducing or inhibiting cancer growth. The cancer includes but is not limited to bladder cancer, bone cancer, skin cancer and ovarian cancer.

This invention provides a composition for reducing or inhibiting cancer growth comprising any of compound selected from following:

A) 3-O-[β-D-galactopyranosyl(1→2)]-α-L-arabinofuranosyl(1→3)-β-D-glucuronopyranosyl-21,22-O-diangeloyl-3β,15α,16α,21β,22α,28-hexahydroxyolean-12-ene, B) 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β,16α,21β, 22α,28-pentahydroxyolean-12-ene C) 3-O-[β-D-glucopyranosyl-(1→2)]-α-L-arabinofuranosyl (1→3)-(-D-glucuronopyranosyl-21,22-O-diangeloyl-3β, 15α,16α,21β,22α,28-heptahydroxyolean-12-ene D) 3-O-[β-galactopyranosyl (1→2)]-α-arabinofuranosyl (1→43)-β-glucuronopyranosyl-21,22-O-diangeloyl-3β, 16α,21β,22α,28-pentahydroxyolean-12-ene E) 3-O-[β-galactopyranosyl (1→2)]-α-arabinofuranosyl (1→3)-β-glucuronopyranosyl-21-O-(3,4-diangeloyl)-α-rhamnopyranosyl-28-O-acetyl-3β,16α,21β,22α,28-pentahydroxyolean-12-ene F) 3-O-[β-galactopyranosyl (1→2)]-α-arabinofuranosyl (1→3)-β-glucuronopyranosyl-21,22-O-diangeloyl-3β, 16α,21β,22α,28-pentahydroxyolean-12-ene G) 3-O-[β-D-galactopyranosyl (1→2)]-α-L-arabinofuranosyl (1→3)-β-D-glucuronopyranosyl-21,22-O-dibenzoyl-3β,15α,16α,21β,22α,28-hexahydroxyolean-12-ene, H) 3-O-[β-D-galactopyranosyl(1→2)]-α-L-arabinofuranosyl(1→3)-β-D-glucuronopyranosyl-21-O-(3,4-dibenzoyl)-α-L-rhamnophyranosyl-22-O-acetyl-3β,16α,21β, 22α,28-pentahydroxyolean-12-ene I) 3-O-[β-D-glucopyranosyl-(1→2)]-α-L-arabinofuranosyl (1→3)-(-D-glucuronopyranosyl-21,22-O-dibenzoyl-3β, 15α,16α,21β,22α,24 β,28-heptahydroxyolean-12-ene J) 3-O-[β-galactopyranosyl (1→2)]-α-arabinofuranosyl (1→3)-β-glucuronopyranosyl-21,22-O-dibenzoyl-3β, 16α,21β,22α,28-pentahydroxyolean-12-ene K) 3-O-[β-galactopyranosyl (1→2)]-α-arabinofuranosyl (1→3)-β-glucuronopyranosyl-21-O-(3,4-dibenzoyl)-α-rhamnopyranosyl-28-O-acetyl-3β,16α,21β,22α,28-pentahydroxyolean-12-ene L) 3-O-[β-galactopyranosyl (1→2)]-α-arabinofuranosyl (1→3)-β-glucuronopyranosyl-21,22-O-dibenzoyl-3β, 16α,21β,22α,28-pentahydroxyolean-12-ene M) 3-O-[β-D-galactopyranosyl (1→2)]-β-D-xyopyranosyl (1→3)-β-D-glucuronopyranosyl-21,22-O-dibenzoyl-3β, 15α,16α,21β,22α,28-hexahydroxyolean-12-ene, N) 3-O-[β-D-galactopyranosyl(1→2)]-β-D-xyopyranosyl (1→3)-β-D-glucuronopyranosyl-21-O-(3,4-dibenzoyl)-α-L-rhamnophyranosyl-22-O-acetyl-3β,16α,21β,22α, 28-pentahydroxyolean-12-ene O) 3-O-[β-D-glucopyranosyl-(1→2)]-β-D-xyopyranosyl (1→3)-(-D-glucuronopyranosyl-21,22-O-dibenzoyl-3β, 15α,16α,21β,22α,24β,28-heptahydroxyolean-12-ene P) 3-O-[β-D-galactopyranosyl (1→2)]-β-D-xyopyranosyl (1→3)-β-D-glucuronopyranosyl-21,22-O-dibenzoyl-3β, 16α,21β,22α,28-pentahydroxyolean-12-ene Q) 3-O-[β-galactopyranosyl (1→2)]-β-xyopyranosyl (1→3)-β-glucuronopyranosyl-21-O-(3,4-dibenzoyl)-α-rhamnopyranosyl-28-O-acetyl-3β,16α,21β,22α,28-pentahydroxyolean-12-ene R) 3-O-[β-galactopyranosyl (1→2)]-β-xyopyranosyl (1→3)-β-glucuronopyranosyl-21,22-O-dibenzoyl-3β,16α,21β, 22α,28-pentahydroxyolean-12-ene S) 3-O-[β-D-galactopyranosyl(1→2)]-β-D-xyopyranosyl (1→3)-β-D-glucuronopyranosyl-21,22-O-diangeloyl-3β,15α,16α,21β,22α,28-hexahydroxyolean-12-ene, T) 3-O-[β-D-galactopyranosyl(1→2)]-β-D-xyopyranosyl (1→3)-β-D-glucuronopyranosyl-21-O-(3,4-diangeloyl)-α-L-rhamnophyranosyl-22-O-acetyl-3β,16α,21β,22α,28-pentahydroxyolean-12-ene U) 3-O-[β-D-glucopyranosyl-(1→2)]-β-D-xyopyranosyl (1→3)-(-D-glucuronopyranosyl-21,22-O-diangeloyl-3β,15α,16α,21β,22α,24β,28-heptahydroxyolean-12-ene V) 3-O-[β-galactopyranosyl (1→2)]-β-D-xyopyranosyl (1→3)-β-glucuronopyranosyl-21,22-O-diangeloyl-3β,16α,21β,22α,28-pentahydroxyolean-12-ene W) 3-O-[β-galactopyranosyl (1→2)]-β-D-xyopyranosyl (1→3)-β-glucuronopyranosyl-21-O-(3,4-diangeloyl)-α-rhamnopyranosyl-28-O-acetyl-3β,16α,21β,22α,28-pentahydroxyolean-12-ene X) 3-O-[β-D-galactopyranosyl (1→2)]-β-D-xyopyranosyl (1→3)-β-D-glucuronopyranosyl-21,22-O-diangeloyl-3β,16α,21β,22α,28-pentahydroxyolean-12-ene This invention provides a composition for reducing or inhibiting cancer growth comprising any of compound selected from following:

A) 3-O-[β-D-galactopyranosyl(1→2)]-α-L-arabinofuranosyl(1→3)-β-D-glucuronopyranosyl-21-O-angeloyl,22-O-benzoyl-3β,15α,16α,21β,22α,28-hexahydroxyolean-12-ene, B) 3-O-[β-D-galactopyranosyl(1→2)]-α-L-arabinofuranosyl(1→3)-β-D-glucuronopyranosyl-21-O-(3-angeloyl,4-benzoyl)-α-L-rhamnophyranosyl-22-O-acetyl-3β,16α,21β,22α,28-pentahydroxyolean-12-ene C) 3-O-[β-D-glucopyranosyl-(1→2)]-α-L-arabinofuranosyl(1→3)-(-D-glucuronopyranosyl-21-O-angeloyl,22-O-benzoyl-3β,15α,16α,21β,22α,24β,28-heptahydroxyolean-12-ene D) 3-O-[β-galactopyranosyl (1→2)]-α-arabinofuranosyl (1→3)-β-glucuronopyranosyl-21-O-angeloyl,22-benzoyl-3β,16α,21β,22α,28-pentahydroxyolean-12-ene E) 3-O-[β-galactopyranosyl (1→2)]-α-arabinofuranosyl (1→3)-β-glucuronopyranosyl-21-O-F) (3-angeloyl,4-benzoyl)-α-rhamnopyranosyl-28-O-acetyl-3β,16α,21β,22α,28-pentahydroxyolean-12-ene F) 3-O-[β-galactopyranosyl (1→2)]-α-arabinofuranosyl (1→3)-β-glucuronopyranosyl-21-O-angeloyl,22-O-benzoyl-3β,16α,21β,22α,28-pentahydroxyolean-12-ene G) 3-O-[β-D-galactopyranosyl (1→2)]-α-L-arabinofuranosyl (1→3)-β-D-glucuronopyranosyl-21-O-benzoyl,22-O-angeloyl-3β,15α,16α,21β,22α,28-hexahydroxyolean-12-ene, H) 3-O-[β-D-galactopyranosyl(1→2)]-α-L-arabinofuranosyl(1→3)-β-D-glucuronopyranosyl-21-O-(3-benzoyl,4-angeloyl)-α-L-rhamnophyranosyl-22-O-acetyl-3β,16α,21β,22α,28-pentahydroxyolean-12-ene I) 3-O-[β-D-glucopyranosyl-(1→2)]-α-L-arabinofuranosyl (1→3)-(-D-glucuronopyranosyl-21-O-benzoyl,22-O-angeloyl-3β,15α,16α,21β,22α,24β,28-heptahydroxyolean-12-ene J) 3-O-[β-galactopyranosyl (1→2)]-α-arabinofuranosyl (1→3)-β-glucuronopyranosyl-21-O-benzoyl,22-O-angeloyl-3β,16α,21β,22α,28-pentahydroxyolean-12-ene K) 3-O-[β-galactopyranosyl (1→2)]-α-arabinofuranosyl (1→3)-β-glucuronopyranosyl-21-O-(3-benzoyl,4-angeloyl)-α-rhamnopyranosyl-28-O-acetyl-3β,16α,21β,22α,28-pentahydroxyolean-12-ene L) 3-O-[β-galactopyranosyl (1→2)]-α-arabinofuranosyl (1→3)-β-glucuronopyranosyl-21-O-benzoyl,22-O-angeloyl-3β,16α,21β,22α,28-pentahydroxyolean-12-ene M) 3-O-[β-D-galactopyranosyl (1→2)]-β-D-xyopyranosyl (1→3)-β-D-glucuronopyranosyl-21-O-angeloyl,22-O-benzoyl-3β,15α,16α,21β,22α,28-hexahydroxyolean-12-ene, N) 3-O-[β-D-galactopyranosyl(1→2)]-β-D-xyopyranosyl (1→3)-β-D-glucuronopyranosyl-21-O-(3-angeloyl,4-dibenzoyl)-α-L-rhamnophyranosyl-22-O-acetyl-3β,16α,21β,22α,28-pentahydroxyolean-12-ene O) 3-O-[β-D-glucopyranosyl-(1→2)]-β-D-xyopyranosyl (1→3)-(-D-glucuronopyranosyl-21-O-21-O-angeloyl,22-O-benzoyl-3β,15α,16α,21β,22α,24β,28-heptahydroxyolean-12-ene P) 3-O-[β-D-galactopyranosyl (1→2)]-β-D-xyopyranosyl (1→3)-β-D-glucuronopyranosyl-2121-O-angeloyl,22-O-benzoyl-3β,16α,21β,22α,28-pentahydroxyolean-12-ene Q) 3-O-[β-galactopyranosyl (1→2)]-β-xyopyranosyl (1→3)-β-glucuronopyranosyl-21-O-(3-angeloyl,4-dibenzoyl)-α-rhamnopyranosyl-28-O-acetyl-3β,16α,21β,22α,28-pentahydroxyolean-12-ene R) 3-O-[β-galactopyranosyl (1→2)]-β-xyopyranosyl (1→3)-β-glucuronopyranosyl-angeloyl,22-O-benzoyl-3β,16α,21β,22α,28-pentahydroxyolean-12-ene S) 3-O-[β-D-galactopyranosyl(1→2)]-β-D-xyopyranosyl (1→3)-β-D-glucuronopyranosyl-21-O-benzoyl, 22-O-angeloyl-3β,15α,16α,21β,22α,28-hexahydroxyolean-12-ene, T) 3-O-[β-D-galactopyranosyl(1→2)]-β-D-xyopyranosyl (1→3)-β-D-glucuronopyranosyl-21-O-(3-benzoyl,4-angeloyl)-α-L-rhamnophyranosyl-22-O-acetyl-3β,16α,21β,22α,28-pentahydroxyolean-12-ene U) 3-O-[β-D-glucopyranosyl-(1→2)]-β-D-xyopyranosyl (1→3)-(-D-glucuronopyranosyl-21-O-benzoyl,22-O-angeloyl-3β,15α,16α,21β,22α,24β,28-heptahydroxyolean-12-ene V) 3-O-[β-galactopyranosyl (1→2)]-β-D-xyopyranosyl (1→3)-β-glucuronopyranosyl-21-O-benzoyl,22-O-angeloyl-3β,16α,21β,22α,28-pentahydroxyolean-12-ene W) 3-O-[β-galactopyranosyl (1→2)]-β-D-xyopyranosyl (1→3)-β-glucuronopyranosyl-21-O-(3-benzoyl,4-angeloyl)-α-rhamnopyranosyl-28-O-acetyl-3β,16α,21β,22α,28-pentahydroxyolean-12-ene X) 3-O-[β-D-galactopyranosyl (1→2)]-β-D-xyopyranosyl (1→3)-β-D-glucuronopyranosyl-21-O-benzoyl,22-O-angeloyl-3β,16α,21β,22α,28-pentahydroxyolean-12-ene Triterpenoid saponins with the characteristic structure mentioned above in this invention can be used to reduce or inhibit cancer growth. The cancer includes but is not limited to bladder cancer, bone cancer, skin cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

The saponins isolated from *Harpullia austro-calcdonica* with the characteristic structure described in the present invention can be used for anti-cancer therapy. The cancer includes but is not limited to bladder cancer, bone cancer and ovarian cancer.

This invention provides a composition comprising the above described compounds or their derivatives for inhibiting human immunodeficiency virus (HIV), Severe Acute Respiratory Syndrome (SARS), flu disease or inhibits virus activities.

The biologically active triterpenoid saponins structures are shown in FIG. 11A. See also Phytochemistry 59 (2002) 825-832, Triterpenoid saponins and acylated prosapogenins from *Harpullia austro-calcdonica*.

Wherein R1=R2=angeloyl group; R3=CH2OH or CH3 or CHO.

The biologically active triterpenoid saponins structures are shown in FIG. 15. See also Phytochemistry 66 (2005) 825-835, Haemolytic acylated triterpenoid saponins from *Harpullia austro-calcdonica*.

Triterpenoid saponins isolated from seeds of *Aesculus chinensis* having the characteristic structure(s) as disclosed in the present invention can be used in anti-cancer therapy. The cancer that triterpenoid saponins is effective against includes but is not limited to bladder cancer, bone cancer and ovarian cancer. This invention provides a composition comprising the above-described compounds and their derivatives for inhibiting cancer, Severe Acute Respiratory Syndrome (SARS), flu disease or inhibits virus activities.

Triterpenoidal saponins comprise the structures shown or described in FIG. 7A.

| Wherein | R1 | R2 | R3 |
|---|---|---|---|
| 1 | Tigloyl | Acetyl | H |
| 2 | Angeloyl | Acetyl | H |
| 3 | Tigloyl | H | H |
| 4 | Angeloyl | H | Acetyl |
| 5 | H | Tigloyl | Acetyl |
| 6 | H | Angeloyl | Acetyl |
| 7 | H | H | Tigloyl |
| 8 | H | H | Angeloyl |

See also J. Nat. Prod. 1999, 62, 1510-1513.Anti-HIV-1 Protease Triterpenoid Saponins from the seed of *Aesculus chinensis*.

Triterpenoid saponins isolated from *Aesculus, Aesculus arguta, Aesculus assamica* Griff., *Aesculus californica* (Spach) Nutt., *Aesculus chinensis* Bunge, *Aesculus chinensis* var. *Chekiangensis* (Hu et Fang) Fang, *Aesculus chuniana* Hu et Fang, *Aesculus flava* (*A. octandra*), *Aesculus glabra* Willd., *Aesculus hippocastanum, Aesculus indica, Aesculus lantsangensis* Hu et Fang, *wangii Aesculus megaphylla* Hu et Fang, *chinensis Aesculus neglecta, Aesculus octandra* Marsh., *Aesculus parviflora, Aesculus pavia, Aesculus polyneura* Hu et Fang, *Aesculus tsianguii* Hu et Fang, *Aesculus sylvatica, Aesculus turbinata, Aesculus wangii* Hu, *Aesculus wangii* var. *ruticola* Hu et Fang or *Aesculus wilsonii*, having the characteristic structure(s) as disclosed in the present invention can be used in anti-cancer therapy. The cancer that triterpenoid saponin is effective against includes but is not limited to bladder cancer, bone cancer and ovarian cancer. This invention provides a composition comprising the above-described compounds and their derivatives for inhibiting cancer, Severe Acute Respiratory Syndrome (SARS), flu disease or inhibits virus activities.

Triterpenoid saponins comprise the structures shown or described in FIG. 7A, 7B, 7C, 7D.

Wherein R1=angeloyl group or tigloyl group or senecioyl group or acetyl or H.

R2=angeloyl group or tigloyl group or senecioyl group or acetyl group or acetyl or H.

R3=angeloyl group or tigloyl group or senecioyl group or acetyl group or acetyl or H.

R6=H or OH

Position 23-27 and 28-30 are attached with CH3 or CH2OH or COOH or CHO

Triterpenoid saponins isolated from *Aesculus, Aesculus arguta, Aesculus assamica* Griff., *Aesculus californica* (Spach) Nutt., *Aesculus chinensis* Bunge, *Aesculus chinensis* var. *Chekiangensis* (Hu et Fang) Fang, *Aesculus chuniana* Hu et Fang, *Aesculus flava* (*A. octandra*), *Aesculus glabra* Willd., *Aesculus hippocastanum, Aesculus indica, Aesculus lantsangensis* Hu et Fang, *wangii Aesculus megaphylla* Hu et Fang, *chinensis Aesculus neglecta, Aesculus octandra* Marsh., *Aesculus parviflora, Aesculus pavia, Aesculus polyneura* Hu et Fang, *Aesculus tsianguii* Hu et Fang, *Aesculus sylvatica, Aesculus turbinata, Aesculus wangii* Hu, *Aesculus wangii* var. *ruticola* Hu et Fang or *Aesculus wilsonii*, having the characteristic structure(s) as disclosed in the present invention can be used in anti-cancer therapy. The cancer that triterpenoid saponin is effective against includes but is not limited to bladder cancer, bone cancer, skin cancer and ovarian cancer. This invention provides a composition comprising the above-described compounds and their derivatives for inhibiting cancer, Severe Acute Respiratory Syndrome (SARS), flu disease or inhibits virus activities.

Triterpenoidal saponins comprise the structures shown or described in FIG. 16A, 16B.

Wherein R1=angeloyl or Tigloyl or Senecioyl or acetyl or H

R2=angeloyl or Tigloyl or Senecioyl or acetyl or H

R6=angeloyl or Tigloyl or Senecioyl or acetyl or H

R3=H or OH

R10=CH3 or CH2OH or CHO

R5=sugar moiety or D-glucose or D-galactose or L-rhamnose or L-arabinose or, D-xylose or alduronic acid or D-glucuronic acid or D-galacturonic acid or H R7=sugar moiety or D-glucose or D-galactose or L-rhamnose or L-arabinose or, D-xylose or alduronic acid or D-glucuronic acid or D-galacturonic acid or H R8=sugar moiety or D-glucose or D-galactose or L-rhamnose or L-arabinose or, D-xylose or alduronic acid or D-glucuronic acid or D-galacturonic acid or H R9=COOH or CH2OH Triterpenoid saponins isolated from the plants described in this invention with the characteristic structure mentioned in this invention can be used to reduce or inhibit cancer growth. The cancer includes but is not limited to bladder cancer, bone cancer, skin cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

See structure of compounds in FIG. 17.

Triterpenoid saponins isolated from roots of *Camellia sinensis* var. *assamica*, showed in FIG. 13 with the characteristic structure mentioned in this invention is effective in inhibiting or reducing cancer growth. The cancer includes but is not limited to bladder cancer, bone cancer, skin cancer and ovarian cancer.

This invention provides a composition comprising the above described compounds and their derivatives for inhibiting human immunodeficiency virus (HIV), Severe Acute Respiratory Syndrome (SARS), flu disease or inhibits virus activities. See also Phytochemistry 53(2000) 941-946 Triterpenoid saponins from the roots of tea plant (*Camellia sinensis* var. *assamica*).

Triterpenoid saponins isolated from *Pittosporum viridiflorum* with the characteristic structure mentioned in this invention can be used to reduce or inhibit cancer growth. The cancer includes but is not limited to bladder cancer, bone cancer, skin cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

See structure of compounds in FIGS. 9 A and 9B.

Wherein R1=angeloyl group.

R2=senecioyl group.

See also 3:J. Nat. Prod. 2002, 65, 65-68. A New Triterpene Saponin from *Pittosporum viridiflorum* from Madagascar Rainforest.

The triterpenoid saponins isolated from Pittosporum tobira with the characteristic structure mentioned in this invention can be used for anti-cancer therapy. The cancer includes but is not limited to bladder cancer, bone cancer and ovary cancer. This invention also provides a composition comprising the above described compounds and their derivatives capable of inhibiting human immunodeficiency virus (HIV), Severe Acute Respiratory Syndrome (SARS) or flu disease, or capable of inhibiting viral activities.

See structure of compounds in FIG. 10.

Wherein

|   | R1 | R2 | R3 | R4 |
|---|---|---|---|---|
| 1. | 2-acetoxy-2-methybutanoyl | acetyl | H | COOH |
| 2. | Angeloyl | acetyl | H | COOH |
| 3. | Angeloyl | H | acetyl | COOH |
| 4. | Angeloyl | angeloyl | H | COOH |
| 5 | H | H | H | COOH |
| 7 | H | H | H | COOMe |
| 8 | H | H | H | $CH_2OH$ |

R5 = α-L-ara$f$
R6 = α-L-ara$p$
R7 = β-D-glu$p$

See also Tetrahedron 58(2002)10127-10136. Isolation and structure elucidation of four new triterpenoid estersaponins from fruit of *Pittosporum tobira* AIT.

The triterpenoid saponins isolated from *Maesa lanceolata* with the characterized structure mentioned in this invention can be used to reduce or inhibit cancer growth. The cancer includes but is not limited to bladder cancer, bone cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

See structure of compounds in FIG. 14.

Wherein:

| compound | R1 | R2 | R3 |
|---|---|---|---|
| 2 | acetyl | H | angeloyl |
| 3 | H | acetyl | angeloyl |
| 5 | H | propanoyl | angeloyl |
| 7 | H | butanoyl | angeloyl |
| 8 | H | angeloyl | angeloyl |

-continued

| compound | R1 | R2 | R3 |
|---|---|---|---|
| 4 | acetyl | acetyl | angeloyl |
| 6 | acetyl | propanoyl | angeloyl |
| 9 | acetyl | butanoyl | angeloyl |
| 10 | acetyl | angeloyl | angeloyl |

See also Phytochemistry 52(1999)1121-1131. New acylated triterpenoid saponins from *Maesa lanceolata*.

The triterpenoid saponins isolated from *Xanthoceras sobifolia* with the characteristic structure mentioned in this invention can be used to reduce or inhibit cancer growth. The cancer includes but is not limited to bladder cancer, bone cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

See structures of saponins in FIG. 1 to FIG. 6.

See also PCT/US04/043459 and PCT/US04/043465.

This invention provides a method for inhibiting tumor cell growth, human immunodeficiency virus (HIV), Severe Acute Respiratory Syndrome (SARS) or flu disease, or capable of inhibiting viral activities, comprising contacting an effective amount of the compounds in FIG. 1 to FIG. 27. In an embodiment, the above described compound comprising at least two angeloyl groups at carbon 21, 22 and 28. In an embodiment, the above described compound comprising at least two angeloyl groups, tigloyl groups, senecioyl groups or acetyl group or their combinations.

This invention provides a method for inhibiting tumor cell growth, human immunodeficiency virus (HIV), Severe Acute Respiratory Syndrome (SARS) or flu disease, or capable of inhibiting viral activities, comprising contacting an effective amount of the compounds in the FIGS. 3A and B wherein the compound comprises two angeloyl groups at any two of R1, R2 and R4; or the compounds in FIGS. 5A, 5B, 6A and 6B wherein the compound comprises two angeloyl groups at any two of R1, R2, R3 and R4; or the compounds in FIGS. 7A, 7B, 7C and 7D wherein the compound comprises two angeloyl groups at any two of R1, R2 and R3; or the compounds in FIG. 8 wherein the compound comprises two angeloyl groups at any two of R1, R2 and R3; or the compounds in FIGS. 9A, 9B and 10 wherein the compound comprises two angeloyl groups at any two of R1, R2 and R3; or the compounds in FIGS. 11, 12 and 13 wherein the compound comprises angeloyl groups at R1 and R2; or the compounds in FIG. 14 wherein the compound comprises two angeloyl groups at any two of R1, R2 and R3; or the compounds in FIG. 15 wherein the compound comprises two angeloyl groups; or the compounds in FIG. 16 wherein the compound comprises two angeloyl groups at any two of R1, R2 and R6; or the compounds in FIG. 16-25 wherein the compound comprises two angeloyl groups.

This invention provides a method for inhibiting tumor cell growth, human immunodeficiency virus (HIV), Severe Acute Respiratory Syndrome (SARS) or flu disease, or capable of inhibiting viral activities, comprising contacting an effective amount of the above described compounds. In an embodiment, the compound is a triterpenoidal saponin or a sapongenin comprising two angeloyl groups attached to carbon 21 and 22 of its sapogenin. In an embodiment, the sapongenin comprising any two of angeloyl groups, tigloyl groups or senecioyl groups, or their combinations thereof attached to carbon 21 and 22 of its sapogenin. In another embodiment, the compound is a triterpenoidal saponin or a sapongenin comprising any two of angeloyl groups, tigeloyl groups or senecioyl groups, or their combinations thereof attached to a sugar moiety which bonds to carbon 21 or 22.

In a further embodiment, the compound is a triterpenoidal saponin or sapongenin comprising at least any one of angeloyl group, tigloyl group, or senecioyl group, or their combinations thereof attached to carbon 21 and/or 22 of its sapogenin. In a further embodiment, the compound is a triterpenoidal saponin or a sapongenin comprising at least two of angeloyl group or tigloyl group or senecioyl group, or their combinations thereof attached to a sugar moiety which bonds to carbon 21 or 22. In an embodiment, the compound is a triterpenoidal saponin or a sapongenin comprising at least two angeloyl groups attached to carbon 21, 22 or 28 of its sapogenin. In another embodiment, the compound is a triterpenoidal saponin or a sapongenin comprising any two of angeloyl groups, tigeloyl groups or senecioyl groups, or their combinations thereof attached to a sugar moiety which bonds to carbon 21, 22 or 28. In an embodiment, the compound is a triterpenoidal saponin or a sapongenin comprising a sugar moiety comprises at least two angeloyl groups attached to carbon 21, 22 or 28 of its sapogenin.

In a further embodiment, the compound is a five ring triterpene comprising at least two angeloyl group, attached to the side chains at one end of the five rings of its sapogenin and a sugar moiety is attached to the side chains of the ring at the other end of the triterpene. In an embodiment the compound comprising at least any two of angeloyl group, tigloyl group, or senecioyl group, or their combinations thereof.

In a further embodiment, the compound is a sapogenin or triterpene comprising at least two angeloyl group, attached to the side chains of its sapogenin and a sugar moiety is attached to the side chains of the triterpene or sapogenin. In an embodiment the compound comprising at least any two of angeloyl group, tigloyl group, or senecioyl group, or their combinations thereof.

In a further embodiment, the compound comprises at least two angeloyl group, attached to the side chains of a compound and a sugar moiety is attached to a side chain of the compound. In an embodiment the compound comprising at least any two of angeloyl group, tigloyl group, or senecioyl group, or their combinations thereof. In an embodiment, the angeloyl can be replaced by a function group which has the function as angeloyl group.

In a further embodiment, a sugar moiety or chain with one or more sugar such as D-glucose, D-galactose, L-rhamnose, L-arabinose, D-xylose, alduronic acid, D-glucuronic acid or D-galacturonic acid, or their combinations thereof, or their derivatives thereof is attached to carbon 3.

In a further embodiment, the compound is a triterpene or sapongenin comprising at least any one of angeloyl group, tigloyl group or senecioyl group, or their combinations thereof attached to it. In a further embodiment, the compound is a triterpene or sapongenin comprising at least one of angeloyl group, tigloyl group or senecioyl group, or their combinations thereof attached to a sugar moiety which bonds to it.

In a further embodiment, at least one sugar moiety with one or more sugar, D-glucose, D-galactose, L-rhamnose, L-arabinose, D-xylose, or alduronic acid, D-glucuronic acid or D-galacturonic acid, or their combinations thereof, or their derivatives thereof is attached to the triterpene. In a further embodiment, bonds 23-30 are attached with CH3 or CH2OH or COOH or acetyl group.

The activities of a saponin compound for regulating or inhibiting tumor cell growth are based on or attributed to its structure that comprises functional group(s) such as angeloyl group, tigloyl group, senecioyl group or acetyl group, or their combinations thereof.

The Compound Y1 and Compound Y2 which comprise with two angeloyl groups show the inhibition on the growth of ovarian cancer cells. See FIG. 29.

The Compound Y, Y8, Y9 and Y10 which comprise with two angeloyl groups show the inhibition on ovarian cancer cells as determined by MTT assay. See FIG. 30.

The compound with single angeloyl group shows weaker anticancer activity than a compound with two angeloyl groups. See FIG. 28.

The compound with two angeloyl groups is more potency than the one with on angeloyl for inhibiting human immunodeficiency virus (HIV), Severe Acute Respiratory Syndrome (SARS), flu disease or inhibits virus activities.

This invention provides a composition comprising the compounds comprises the structure of:

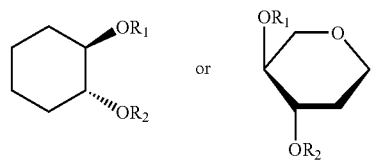

wherein R1 and R2 are angeloyl group. In embodiment, R1 and R2 are angeloyl groups, tigloyl groups, senecioyl groups or acetyl group or their combinations. In embodiment, R1 and R2 comprise compound selected from angeloyl, acetyl, tigloyl, senecioyl, alkyl, benzoyl, dibenzoyl, alkanoyl, alkenoyl, benzoyl alkyl substituted alkanoyl, aryl, heterocylic or heteroraryl or derivative thereof.

The above compounds can be used for inhibiting tumor cell growth, human immunodeficiency virus (HIV), Severe Acute Respiratory Syndrome (SARS) or flu disease, or capable of inhibiting viral activities, comprising contacting an effective amount of the above described compounds.

This invention provides a method of inhibiting the growth of ovarian cancer, breast cancer, brain cancer, bladder cancer, prostate cancer, bone cancer, skin cancer, leukocyte cancer, liver cancer or leukemia in a subject, comprising administering to a subject, in need thereof, an effective amount of the compound which comprises any of the above structures to said subject.

Theis invention provides a method for inhibiting tumor cell growth, regulating cell growth, reducing inflammation, in a subject, comprising administering to a subject, in need thereof, an effective amount of the compound which comprises any of the above structures to said subject.

This invention provides a method for reducing leg swelling, reducing the symptom of chronic venous insufficiency, peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, haemonhoids, peripheral oedema formation or postoperative swelling; for reducing symptoms of leg pain; for treating pruritis, lower leg volume, for reducing symptoms of pain; thrombosis, thrombophlebitis; for preventing gastric ulcers antispasmotic comprising administering to a subject, in need thereof, an effective amount of the composition of this invention.

This invention provides a composition comprising the compounds of the invention for treating enuresis and frequency micturition, and for improving the functions of the central nervous system including signaling the bladder to wake up from deep sleep or to relax the bladder so that it can store more urine. The compounds of the invention can be used to relax the detrusor tension caused by aging, stress, nervousness, over-activity, instability, hyper-reflexia, and uninhibited bladder. In another embodiment, the compounds may be used for relaxing the contracted bladder tissue induced by acetylcholine (Ach). The compounds identified and isolated from extract of this invention may be used as acetylcolinesterase, an AChE inhibitor, for regulating Antidiuretic hormone (ADH), which reduces the volume of urine, and as an anti-inflammatory agent.

The compounds of the invention can be used for accelerating the growth of bladder, for suppressing deep sleep, for increasing alterness in a sleeping subject, for modulating the release, breakdown and uptake of Antidieuretic hormone (ADH) and its receptors, for modulating the secretion, breakdown and uptake of Adrenocorticotropic hormone (ACTH) and its receptors, for modulating the release, breakdown and uptake of 5-hydroxytryptamine and its receptors, for modulating the release, breakdown and uptake of Acetycholine (Ach) and its receptors, for modulating the release, breakdown and uptake of Adrenaline (AD) and its receptors, for modulating the release, breakdown and uptake of Dopamine (DA) and its receptors, for modulating the release, breakdown and uptake of Norepinephrine (NE) and its receptors, for preventing sleep paralysis, for modulating the formation, release, breakdown and activity of neuropeptides and their receptors.

This invention provides a composition comprising the compounds of the invention for treating cancers; for inhibiting virus; for preventing cerebral aging; for improving memory; improving cerebral functions, for curing enuresis, frequent micturition, urinary incontinence dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-Kappa B activation; for treating brain edema, sever acute respiratory syndrome, respiratory viral diseases, chronic venous insufficiency, hypertension, chronic venous disease, anti-oedematous, anti inflammatory, haemonhoids, peripheral oedema formation, varicose vein disease, flu, post traumatic edema and postoperative swelling; for inhibiting ethanol absorption; for lowering blood sugar; for regulating the adreocorticotropin and corticosterone level; and for treating impotence or premature ejaculation or diabetes. See U.S. Ser. No. 10/906,303, filed Feb. 14, 2005, International Application No. PCT/US04/43465, filed Dec. 23, 2004, International Application No. PCT/US04/33359, filed Oct. 8, 2004, and U.S. Ser. No. 11/131,551, filed May 17, 2005, the contents of which are incorporated herein by reference.

This invention provides a composition for treating chronic venous insufficiency, peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, haemonhoids, peripheral oedema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic.

This invention provides a composition for AntiMS, antianeurysm, antiasthmatic, antibradykinic, anticapillarihemorrhagic, anticephalagic, anticervicobrachialgic, antieclamptic, antiedemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, cancerostatic, corticosterogenic, diuretic, fungicide, hemolytic, hyaluronidase inhibitor, lymphagogue, natriuretic, pesticide, pituitary stimulant, thymolytic, vasoprotective, venotonic treatment, In an embodiment, an angeloyl group combined with a coumarin shows strong anti-tumor activities.

This invention provides a compound capable of reducing or inhibiting cancer cell growth, comprising the following structure:

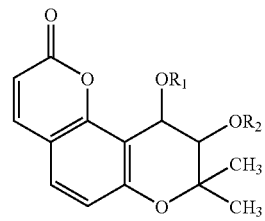

Wherein the R1, R2=Angeloyl, or tigloyl, or senecioyl, or acetyl group.

If the Angeloyl or tigloyl or senecioyl or acetyl in the above compound is replaced with hydroxyl group, the anti-tumor activities will be lost. The replacement of Angeloyl group with tigloyl group also reduces the anti-tumor activities. If we replace the acetyl group with Angeloyl group, the anti-tumor activities is increased. In an embodiment, Angeloyl group combined with a coumarin shows activities. The structure is shown below:

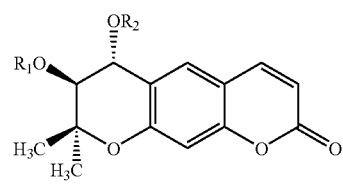

Wherein the R1, R2=Angeloyl or tigloyl or senecioyl or acetyl group.

The structure of the active compounds isolated from *Angelica edulis Miyabe* is shown below:

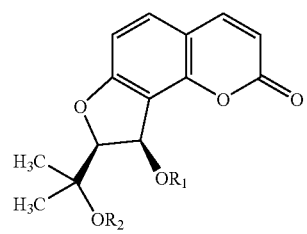

Wherein the R1, R2=Angeloyl or tigloyl or senecioyl or actyl group.

The above described compounds can be used for inhibiting cancer, wherein the cancer is not limited to breast cancer, leukocyte cancer, liver cancer, ovarian cancer, bladder cancer, prostate cancer, bone cancer, skin cancer, lung cancer, brain cancer, cervix cancer, KB cancer or brain cancer.

A sugar moiety is a segment of molecule comprising one or more sugar group.

Alkenyl means, unsaturated linear or branched structures and combinations thereof, having 1-7 carbon atoms, one or more double bonds therein. Non-limiting examples alkenyl groups include vinyl, propenyl, isopropenyl, butenyl, s- and t-butenyl, pentenyl, hexenyl, butadienyl, pentadienyl, hexadienyl.

An aryl is a functional group of organic molecule derived from an aromatic compound such as benzene, a 6-14 menbered carbocyclic aromatic ring system cpmprising 1-3 benzene ring s. If two or more aromatic rings are present, then the rings are fused together, so that adjacent rings share a commonbond. Examples include phenyl and naphthyl. The aryl group may be substituted with one or more sunstitutes independetly selected from halogen, alkyl or alkoxy.

Acyl is a function group obtained from an organic acid by the removal of the carboxyl. Acyl groups can be written as having the general formula —COR, where there is a double bond between the carbon and oxygen. The names of acyl groups typically end in -yl, such as formyl, acetyl, propionyl, butyryl, benzoyl. Benzoyl is one of acyls, C6H5.COR, obtained from benzoic acid by the removal of the carboxyl.

heterocyclic compound—a compound containing a heterocyclic ring which refers to a non-aromatic ring having 1-4 heteroatoms said ring being isolated or fused to a second ring selected from 3- to 7-menbered alicyclic ring containing 0-4 heteroatoms, aryl and heteroaryl, wherein said heterocyclic include pyrrolidinyl, pipyrazinyl, morpholinyl, trahydrofuranyl, imidazolinyl thiomorpholinyl, and the like.

heterocyclyl groups derived from heteroarenes by removal of a hydrogen atom from any ring atom.

alkanoyl is the general name for an organic functional group R.CO—, where R represents hydrogen nor an alkyl group. Preferably alkanoyl is selected from acetyl, propionoyl, butyryl, isobutyryl, pentanoyl and hexanoyl.

Alkenoyl is alkenylcarbonyl in which alkenyl is defined above. Examples are pentenoyl(tigloyl) and hexenoyl(angeloyl).

Alkyl is a radical containing only carbon and hydrogen atoms arranged in a chain, branched, cyclic or bicyclic structure or their combinations, having 1-18 carbon atoms. Examples included but not limited to methyl, ethyl, propyl isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl, cyclohexyl.

EXPERIMENTAL DETAILS

Experiment 1

Herb Extraction (a) extracting powder of husks or branches or stems or leaves or kernels or roots or barks with organic solvent at ratio of 1:2 for 4-5 times for 20-35 hours each time to form an organic extract; (b) collecting the organic extract; (c) refluxing the organic extract for 2-3 times at 80° C. to form second extract; (d) removing the organic solvent from the second extract; and (e) drying and sterilizing the second extract to form the extract powder.

Experiment 2

Analysis of Extract Components by HPLC Chromatography

Methods.

HPLC. A C-18 reverse phase μbondapak column (Water P/N 27324) was equilibrated with 10% acetonitrile, 0.005% Trifluoroacetic acid (equilibration solution). An extract of plants prepared using the methods described in Experiment 1 was dissolved in equilibration solution (1 mg/ml) before applying into the column. 20 ug of samples was applied into column. Elution conditions: Fractions were eluted (with flow rate 0.5 ml/min.) with acetonitrile gradient from 10% to 80% in 70 min, and then remains at 80% for 10 min. The acetonitrile concentration then decreased to 10% and remained at 10% for 25 min. The fractions were monitored at 207 nm and recorded in chart with a chart speed of 0.25 cm/min and with OD full scale of 0.128. Instruments. Waters Model 510 Solvent Delivery System; Waters 484 tunable Absorbance Detector; Waters 745/745B Data Module.

Absorbance analysis: The absorption profile of extract at various wavelengths was determined. An extract of the present invention was dissolved in 10% acetonitrile/TFA and scanned at 200-700 nm with a spectrophotometer [Spectronic Ins. Model Gene Sys2].

Results

HPLC. The peaks can be accounted for in the profile. The major peaks are labelled following increased concentration of acetonitrile elution.

Absorption maximum. Three absorption maximum were identified for plant extract; 207 nm, 278 nm and 500 nm.

Experiment 3

Determination of the Cell-Growth Activity Effected by Extract with Cancer Cells Derived from Different Human Organs Using MTT Assay Methods and Materials Cells. Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain), Skin and OVCAR-3 (ovary). Cells were grown in culture medium (HeLa-S3, DU145, MCF-7, Hep-G2 and T98G in MEN (Earle's salts); HTB-9, H460, K562, OVCAR-3 in RPMI-1640; HCT-116, U2OS in McCoy-5A) supplemented with 10% fetal calf serum, glutamine and antibiotics in a 5% CO2 humidified incubator at 37° C.

MTT assay. The procedure for MTT assay followed the method described in (Carmichael et al., 1987) with only minor modifications. Cells were seeded into a 96-wells plate at concentrations of 10,000/well (HTB-9, HeLa, H460, HCT116, T98G, OVCAR-3), 15,000/well (DU145, MCF-7, HepG2, U2OS), or 40,000/well (K562), for 24 hours before drug-treatment. Cells were then exposed to drugs for 48 hours (72 hours for HepG2, U2OS, and 96 hours for MCF-7). After the drug-treatment, MTT (0.5 mg/ml) was added to cultures for an hour. The formation of formazan (product of the reduction of tetrazolium by viable cells) was dissolved with DMSO and the O.D. at 490 nm was measured by an ELISA reader [Dynatech. Model MR700]. The MTT level of cells before drug-treatment was also measured (T0). The % cell-growth (% G) is calculated as:

$$\% G = (TD - T0 / TC - T0) \times 100 \quad (1)$$

where TC or TD represent O.D. readings of control or drug-treated cells. When T0>TD, then the cytotoxicity (LC) expressed as % of the control is calculated as:

$$\% LC = (TD - T0/T0) \times 100. \qquad (2)$$

Results

Among the 11 cell lines studies, inhibition of cell-grwoth after exposure of plant extract was observed. However, their sensitivity toward the extract is different. The response of the cell lines to the tested extract can be categorized into four groups: Most sensitive, Sensitive; Semi-sensitive; and least sensitive.

To investigate the inhibition components of the plant extract, the plant extract was fractionated.

Experiment 4

Purification of the Inhibition Components in Plant Extract (A) Fractionation of Plant Extracts with FPLC Methods Column. Octadecyl functionalized silica gel. Column dimension: 2 cm×28 cm; equilibrated with 10% acetonitrile—0.005% TFA before use.

Sample loading: 1-2 ml, concentration: 100 mg/ml in 10% acetonitrile/TFA.

Gradient elution condition: 10-80% acetonitrile in a total volume of 500 ml.

Monitor absorption wavelength: at 254 nm.

Fraction Collector: 5 ml/fractions (collect from 10% to 72% acetonitrile)

Instrument: AKTA-FPLC, P920 pump; Monitor UPC-900; Frac-900.

(B) Isolation of Component Ys with Preparative HPLC

Methods

Column: A preparative HPLC column (Waters Delta Pak C18-300A);

Elution conditions: 45% acetonitrile isocratic elution with flow rate of 1 ml/min.

Fractions are monitored at 207 nm and were collected and lyophilized.

Experiment 5

Determination of the Chemical Structure

Methods

NMR analysis. The pure compound Y of Xanthoceras sorbifolia was dissolved in pyridine-D5 with 0.05% v/v TMS. All NMR spectra were acquired using a Bruker Avance 600 MHz NMR spectrometer with a QXI probe (1H/13C/15N/31P) at 298 K. The numbers of scans for 1D 1H spectra were 16 to 128, depending on the sample concentration. 2D HMQC spectra were recorded with spectral widths of 6000× 24,000 Hz and data points of 2024×256 for t2 and t1 dimensions, respectively. The number of scans was 4 to 128. 2D HMBC were acquired with spectral widths of 6000×30,000 Hz and data points of 2024×512 for t2 and t1 dimensions, respectively. The number of scans was 64. The 2D data were zero-filled in t1 dimension to double the data points, multiplied by cosine-square-bell window functions in both t1 and t2 dimensions, and Fourier-transformed using software XWIN-NMR. The final real matrix sizes of these 2D spectra are 2048×256 and 2048×512 data points (F2×F1) for HMQC and HMBC, respectively.

Mass spectral analysis. The mass of samples was analyzed by (A) MALDI-TOF Mass Spectrometry and by (B) ESI-MS Mass spectrometry. (A) Samples for MALDI-TOF were first dissolved in acetonitrile, and then mixed with the matrix CHCA, i.e., Alpha-cyano-4-hydroxycinnamic acid, 10 mg CHCA/mL in 50:50 water/acetonitrile and 0.1% TFA in final concentration. The molecular weight was determined by the high resolution mass spectroscope analysis with standards. (B) For ESI, the sample was analyzed with LCQ DECA XP Plus machine made by Thermo Finnigan. It is ionized with ESI source and the solvent for the compound is acetonitrile.

Experiment 6

Determination the Anti Virus Activities of Compound of this Invention

The major procedures for the determination of antivirus activity are:

A. Determine the production of HIV virus after a non-lethal dosage of compound is added to the viral culture system.

B. Determine the growth activity of HIV virus after contact to compound. The steps for these experiments are:

1. Pre-treat HIV virus with different dosages of test compound for variable length of time.

2. Mix treated virus with cells.

3. Measure Virus production.

4. Negative control:—no virus in cell.

5. Positive control—untreated virus mixed with cell.

Result: The virus growth is inhibited after treatments of compound of this invention.

Experiment 7

Determination the Treatment of Venous Insufficiency Particularly Hemorrhoids by Compound (Y) of this Invention 1) 5 groups of rats:

2) 3 dose groups (low, mid, high), 1 positive control(no drug, with croton oil), 1 negative control(no drug, no croton Oil)

3) Give drug (Compound Y) for 7 days in 3 dose groups (low, mid, high) of rats.

4) On day 7, apply croton oil to the Give-Drug-groups after giving drug.

5) At the $24^{th}$ hour after applying croton oil, isolate the recto-anus tissue(10 mm) of rats.

6) Apply croton oil to control group. At the $24^{th}$ hour after applying croton oil, isolate the recto-anus tissue (10 mm) of rats.

7) Compare the swelling of give-drug-groups with positive control (no drug, with croton oil) and negative control (no drug, no croton oil).

8) The result shows that Compound Y inhibiting the swelling of recto-annus induced by corton oil.

Experiment 8

Determination the Treatment of Leg Swelling by Compound (Y) of this Invention 1) 5 groups of rats:
2) 3 dose groups (low, mid, high), 1 positive control(no drug, with Carrageenin), 1 negative control(no drug, no Carrageenin)
3) Give drug (Compound Y) for 7 days in 3 dose groups (low, mid, high) of rats.
4) On day 7, apply Carrageenin to the Give-Drug-groups after giving drug 10 min.
5) Measure the swell volume of the paw of rats at 0.5, 1, 2, 4, 6 hours after applying the Carrageenin.
6) Compare the swelling of give-drug-groups with positive control (no drug, with Carrageenin) and negative control (no drug, no Carrageenin).
7) The result shows that Compound Y inhibiting the leg swelling.

What is claimed is:

1. A method for inhibiting ovarian or skin cancer cell growth in a subject, comprising administering to the subject an effective amount of a compound, or its salt or ester thereof of wherein the compound is (ACH-Y) having the following structure:

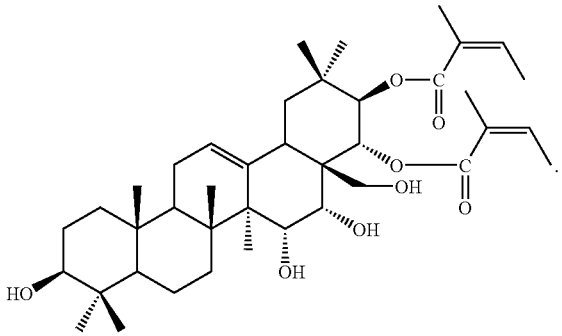

* * * * *

UNITED STATES PATENT AND TRADEMARK OFFICE
CERTIFICATE OF CORRECTION

PATENT NO. : 7,488,753 B2
APPLICATION NO. : 11/289142
DATED : February 10, 2009
INVENTOR(S) : Chan et al.

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 86 days.

Delete the phrase "by 86 days" and insert -- by 129 days --

Signed and Sealed this

Third Day of November, 2009

David J. Kappos
*Director of the United States Patent and Trademark Office*